United States Patent
Spelling

(10) Patent No.: US 7,416,866 B2
(45) Date of Patent: Aug. 26, 2008

(54) PROCESS FOR THE OVEREXPRESSION OF DEHYDROGENASES

(75) Inventor: Tillmann Spelling, Dortmund (DE)

(73) Assignee: Schering AG, Berlin (DE)

( * ) Notice: Subject to any disclaimer, the term of this patent is extended or adjusted under 35 U.S.C. 154(b) by 102 days.

(21) Appl. No.: 10/355,238

(22) Filed: Jan. 31, 2003

(65) Prior Publication Data

US 2004/0091987 A1    May 13, 2004

Related U.S. Application Data

(60) Provisional application No. 60/382,569, filed on May 24, 2002.

(30) Foreign Application Priority Data

Feb. 1, 2002    (DE)    ................ 102 04 798

(51) Int. Cl.
| | | |
|---|---|---|
| C12P 7/00 | (2006.01) |
| C12P 21/04 | (2006.01) |
| C12N 9/04 | (2006.01) |
| C12N 15/00 | (2006.01) |
| C12N 1/20 | (2006.01) |
| C12Q 1/32 | (2006.01) |
| C07H 21/04 | (2006.01) |
| C12Q 1/00 | (2006.01) |
| C12Q 1/68 | (2006.01) |

(52) U.S. Cl. ............. 435/132; 435/190; 435/4; 435/6; 435/26; 435/69.1; 435/71.1; 435/252.3; 435/320.1; 435/440; 536/23.1; 536/23.2

(58) Field of Classification Search ........... 435/190, 435/252.3, 320.1, 440, 4, 6, 26, 252.5, 69.1, 435/71.1, 232, 711; 536/23.2, 23.7
See application file for complete search history.

(56) References Cited

OTHER PUBLICATIONS

Branden et al. Introduction to Protein Structure, Garland Publishing Inc., New York, p. 247, 1991.*
Wang et al. Heterologous gene expression in *Bacillus subtilis*. Biotechnology. 1992;22:63-104.*
Molnar et al. Molecular cloning, expression in *Streptomyces lividans*, and analysis of a gene cluster from Arthrobacter simplex encoding 3-ketosteroid-delta 1-dehydrogenase, 3-ketosteroid-delta 5-isomerase and a hypothetical regulatory protein. Mol Microb., (1995) 15(5), 895-905.*
Molnar et al. NCBI database D37969. 1999.*

* cited by examiner

*Primary Examiner*—Yong D Pak
(74) *Attorney, Agent, or Firm*—Millen, White, Zelano, Branigan, P.C.

(57) ABSTRACT

A process for the overexpression of dehydrogenases, especially for the overexpression of $\Delta^1$-dehydrogenases, in particular for the overexpression of 3-keto steroid-$\Delta^1$-dehydrogenases, as well as for the bacteria, plasmids and DNA sequences that can be used for the overexpression, is described.

6 Claims, 10 Drawing Sheets

```
                       10        20        30        40        50        60
                        |         |         |         |         |         |
Bm3os-delta1-DH   MVNWNEECDVLVAGSGAGGVTGAYTAAREGLDVILVEATDKFGGTTAYSGGGGFWFPANP
Rr3OS-delta1-DH   MAEWAEECDVLVVGSGAGGCCGAYTPAREGLSVILVEASEYFGGTTAYSGGGGVWFPTNA
As3os-delta1-DH   -MDWAEEYDVLVAGSGAGGMAGTYTAAREGLSVCLVEAGDKFGGTTAYSGGGGAWFPANP
Bs3os-delta1-DH   -MKWDASYDVVVVGSGAAGLTAGLTAKLQGLKSLVIEKTDRYGGASA-ISGGALWIPNNH
Mt3os-delta1-DH   --MTVQEFDVVVVGSGAAGMVAALVAAHRGLSTVVVEKAPHYGGSTA-RSGGGVWIPNNE
No3os-delta1-DH   MQDWTSECDLLVVGSGGGALTGAYTAAAQGLTTIVLEKTDRFGGTSA-YSGASIWLPGTQ
Ct3os-delta1-DH   --MAEQEYDLIVVGSGAGACWAPIRAQEQGLKTLVVEKTELFGGTSA-LSGGGIWIPLNY
                       *::*.***...         .**   ::*   :**::*  .*.. *:*  .

70        80        90       100       110       120
                        |         |         |         |         |         |
Bm3os-delta1-DH   VLKRAGTDDTIEDALEYYHAVVGDRTPRELQDTYVKGGAPLVEYLEQDE-NLKFEMLP-W
Rr3OS-delta1-DH   VLQRAGDDDTIEDALTYYPRVVGDRTPHELQEAYVRGGAPLIDYLESDD-DLEFMVYP-W
As3os-delta1-DH   VLLRAGTDDTIEDALEYYRAVVGDRTPADLQETYVRGGAGLVAYLEEDD-HFSFESYP-W
Bs3os-delta1-DH   VIKGAGVPDTHELARQYLDSTVGDRVPEALKEAYITRGPEMLRFLYNKTKHMRFQYAKGY
Mt3os-delta1-DH   VLKRRGVRDTPEAARTYLHGIVGEIVEPERIDAYLDRGPEMLSFVLKHT-PLKMCWVPGY
No3os-delta1-DH   VQERAGLPDSTENARSYLRALLGD-AESERQDAYVETAPAVVALLEQNP-NIEFEFRA-F
Ct3os-delta1-DH   DQKTAGIKDDLETAFGYMKRCVRGMATDDRVLAYVETASKMAEYLRQIG--IPYRAMAKY
                   * * * * *              :*:                :         :

130       140       150       160       170       180
                        |         |         |         |         |         |
Bm3os-delta1-DH   PDYYGKMPKARNDGQRHTMPTPLPISEVGDLHKLVRGPLDFDR----------------
Rr3os-delta1-DH   PDYFGKAPKARAQG-RHIVPSPLPIAGDPELNESIRGPLGRER----------------
As3os-delta1-DH   PDYFGDAPKARRDGQRHIIPTPLPVPSAPELREVVRGPLDNDR----------------
Bs3os-delta1-DH   SDYPEKPGGLSQG-RSIEPLIFDLTKMGSLANTMRRATLSTK-GFTMNSYEFHKVNMIT
Mt3os-delta1-DH   SDYYPEAPGGRPGG-RSIEPKPFNARKLGADMAGLEPAYGKVPLNVVVMQQDYVRLNQLK
No3os-delta1-DH   PDYYKAEGRMDTGR--SINPLDLDPADIGDLAGRCVRNCTKTD----------------
Ct3os-delta1-DH   ADYYPHIEGSRPGG-RTMDPVDFNAARLRVTALETMRPGPPGNQLFGRMSISAFEAHSML
                   .**:             *

190       200       210       220       230       240
                        |         |         |         |         |         |
Bm3os-delta1-DH   ---------------------LGADLPEMLIGG-RALVGRFLKAIGNYPNAKLNLNTP
Rr3os-delta1-DH   ---------------------IGEPLPDMLIGGGRALVGRFLIALRKYPNVDLYRNTP
As3os-delta1-DH   ---------------------LGTPQPDDLFIGGRALVARFLTALATYPHATLVRETA
Bs30s-delta1-DH   RTLKGKTTALKLGMRLV-----KSKVTKSEPVALGEALVARLRLSLAE-ANGELWLSTA
Mt3os-delta1-DH   RHPRGVLRSMKVGARTM-----WAKATGKNLVGMGRALIGPLRIGLQR-AGVPVELNTA
No3os-delta1-DH   ---------------------RMDHAPGRMIGG-RALIAVSAAVQST-ARQNFAPESV
Ct3os-delta1-DH   SRELKSRFTILGIMLKYFLDYPWRNKTRRDRRMTGGQALVAGLLTAANK-ARVEMWCNSP
                                             . **:.       .   .:

250       260       270       280       290       300
                        |         |         |         |         |         |
Bm3os-delta1-DH   LVELVVEDGAVVGALV-----ERDGEQVAIRARKGVIL-AAGGFEGNDELRQKYGVPGVA
Rr3os-delta1-DH   LEELIVEDGVVVGAVV-----GNEVERRAIRARKGVVL-AAGGFDQNDEMRGKYGVPGAA
As3os-delta1-DH   LAELVVEDGVVVGAIV-----ETDGVRRAIRARRGVLL-AAGGFEANDELRQKYGVPGVA
Bs3os-delta1-DH   FKDFMMDKGRVMGIIV-----ERDGQELRIEAKKGVVL-SSGGFSHNQALREQYLPSPTN
Mt3os-delta1-DH   FTDLFVENGVVSGVYVRDSHEAESAEPQLIRARRGVIL-ACGGFEHNEQMRIKYQRAPIT
No3os-delta1-DH   LTSLIVEDGRVVGGLR-----SNPRYRQRIKANRGVLMHAGGGFEGNAEMREQAGTPGKA
Ct3os-delta1-DH   LKELVQDASGRVTGVI---V-ERNGQRQQINARRGVLL-GAGGFERNQEMRDQYLNKPTR
                   *.*.:**::.  ***. *   :*  :
```

FIG. 1a

```
                        310       320       330       340       350       360
                         |         |         |         |         |         |
Bm3os-delta1-DH    RD-TMGPWGNVGQAHQAGIAVGADTDLMDQAWWSPGLTHPDGRSAFALC---FTGGIFVN
Rr3os-delta1-DH    RD-SMGPWSNLGKAHEAGIAVGADVDLMDQAWWSPGLTHPDGRSAFALC---FTGGIFVD
As3os-delta1-DH    RD-TMGPPTNVGAAHQAAIAVGADTDLMGEAWWSPGLTHPDGRSAFALW---FTGGIFVD
Bs3os-delta1-DH    AAWTSSPEGQTGDVIEPGVKIGATLDLMDKVWGAPSVIDPQGQPFFLVADRGVPNMIVVD
Mt3os-delta1-DH    TEWTVGASANTGDGILAAEKLGAALDLMDDAWWGPTVP-LVGKPWFALSERNSPGSIIVN
No3os-delta1-DH    IW-SMGPSGPTPATRSPPELAGRRRNSLARSGVVLPRGRAARRRLHGR---VRGGLVVD
Ct3os-delta1-DH    LVDGNPCGRQYGDAHRAGQAWAHTGADGLVLGRAHHGCSQGAGLSRHFRGTLAAGVHGGQ 370       380       390       400       410       420
                         |         |         |         |         |         |
Bm3os-delta1-DH    DDGKRFVNEYAPYDRLGRDIIA----GMEDGSVTLPYWMIYDDKQGQRPPIAATNVSMVE
Rr3os-delta1-DH    QDGARFTNEYAPYDRLGRDVIA----RMERGEMTLPFWMIYDDRNGEAPPVGATNVPLVE
As3os-delta1-DH    GAGRRFVNESAPYDRLGRAVID----HLTEGGVTPRYWMVYDHKEGSIPPVRATNVSMVD
Bs3os-delta1-DH    SAGQRFENEAAPYHEFVDTMYE----HQKTTQQAVPSWIVIDASTKSRYIFTGLFPGQAF
Mt3os-delta1-DH    MSGKRFMNESMPYVEACHHMYGGEHGQGPGPGENIPAWLVFDQRYRDRYIFAGLQPGQRI
No3os-delta1-DH    SPGSVPQRVASVRPVRTSHGCS-----PDDNGSAVPSFMIFDSREVTDCPPSASRTRPPP
Ct3os-delta1-DH    RQGAALPQRVRPVSGIPAAMLA----ENAKGNGGVPAWIVFDASFRAQNPMGPLMPGSAV
                        *                                         ::: *

430       440       450       460       470       480
                         |         |         |         |         |         |
Bm3os-delta1-DH    TEKYVDAGLWHTADTLE---ELAGKIGVPAENLLATVERFNAMAANDVDEDFGRGDEAYD
Rr3os-delta1-DH    TEKYVDAGLWKTADTLE---ELAGQIGVPAESLKATVARWNELAAKGVDEDFGRGDEPYD
As3os-delta1-DH    EEQYVAAGLWHTADTLP---ELAALIGVPADALVATVARFNELVADGYDADFGRGGEAYD
Bs3os-delta1-DH    PKSWFDHGIVKSAESIE---ELARQMDVLLESLIETVNRFNDFARNGHDDDFYRGDSVYD
Mt3os-delta1-DH    PSRWLDSGVIVQADTLA---ELAGKAGLPADELTATVQRFNAFARSGVDEDYHRGESAYD
No3os-delta1-DH    STSKPEPGSVPTLSK-----NSLPRPDYRPERIAQHCRKVQRCRKLGVDEEFHRGEDPYD
Ct3os-delta1-DH    PDSKVRKSWLNNVYWKGRRWKIWRADRRGRAGLQVSARRMTEYARAGKDLDFDRGGNVFD
                     .         :         :      :         .  *  :: **  . :*

490       500       510       520       530       540
                         |         |         |         |         |         |
Bm3os-delta1-DH    RAFTGGGP----ALIPIEQGPFHAAAFGISDLGTKGGLRTDTAARVLDTSGNPIPGLYAA
Rr3os-delta1-DH    LAFTGGGS----ALVPIEQGPFHAAQFGISDLGTKGGLRTDTVGRVLDSEGAPIPGLYAA
As3os-delta1-DH    RFFSGGEP----PLVSIDEGPFHAAAFGISDLGTKGGLRTDTSARVLTADGTPIGGLYAA
Bs3os-delta1-DH    NYYGDPTL-PNPNLAEIKKAPFYALRIYPGDIGTKGGL-VDEHARVIKADGEPIEGLYAS
Mt3os-delta1-DH    RYYGDPSNKPNPNLGEVGHPPYYGAKMVPGDLGTKGGIRTDVNGRALRDDGSIIDGLYAA
No3os-delta1-DH    AFFCPPNGGANAALTAIENGPFYAARDRLSDLGTKGGLVTDVNGRVLRADGSAIDGLYAA
Ct3os-delta1-DH    RYYGDPRL-KNPNLGPIEKGPFYAMRLWPGEIGTKGGLLTDREGRVLDTQGRIIEGLYCV
                    :          *  :  *::.     .::*****: .*  .*.:  .*  *  ***.

550       560       570       580
                         |         |         |         |
Bm3os-delta1-DH    GNTMAAPSGTTYPGGGNPIGTSMLFSHIAAMNIAGK------------
Rr3os-delta1-DH    GNTMAAPSGTVYPGGGNPIGASALFAHLSVMDAA--------------
As3os-delta1-DH    GNTMAAPSGTTYPGGGNPIGTSMLFSHLAVRHMGTEDAR---------
Bs3os-delta1-DH    GNCSASIMGETYPGPGATIGPGMTLSFVAATTHMANTVKKEEVPLVKI--
Mt3os-delta1-DH    GNVSAPVMGHTYPGPGGTIGPAMTFGYLAALHIADQAGKR--------
No3os-delta1-DH    GNTSASV-APFYPGPGVPLGTAMVFSYRAAQDMAK-------------
Ct3os-delta1-DH    GNNSASVMAPAYAGAGSTLGPAMTFAFRAVADMVGKPLPLENPHLLGKTV
                   **  *.   . *.* *  ::*..   ::. . :.
```

FIG. 1b

PROCESS FOR THE OVEREXPRESSION OF DEHYDROGENASES

This application claims the benefit of the filing date of U.S. Provisional Application Ser. No. 60/382,569 filed May 24, 2002.

This invention relates to a process for the overexpression of dehydrogenases, especially $\Delta^1$-dehydrogenases, in particular 3-keto steroid-$\Delta^1$-dehydrogenases as well as the bacteria, plasmids and DNA sequences that are used for the overexpression.

The 3-keto steroid-$\Delta^1$-dehydrogenase is an enzyme that fulfills an important function in steroid metabolism. With the aid of this enzyme, the selective introduction of a double bond at 1-position in the steroid skeleton is made possible. This reaction is of great importance for the synthesis of a wide variety of pharmaceutical active ingredients [e.g., betamethasone, deflazacort, fluocortolone, hydroxy acid, prednisolone, etc.]. It would be desirable to make available large amounts of this enzyme for a microbiological reaction.

For processes for microbial materials conversion, such as, e.g., steroid transformations, wild strains of yeasts, fungi and bacteria are generally used [see, i.a., Kieslich, K. (1980), *Steroid Conversions*, In: *Economic Microbiology—Microbial Enzymes and Transformation*, Rose, A. H. (ed.), Academic Press, London, Vol. V, pp. 370-453; Kieslich, K. and Sebek, O. K. (1980) *Microbal Transformations of Steroids*, In: *Annual Reports on Fermentation Processes*, Perlman, D. (ed.), Academic Press, New York, Vol. 3, pp. 275-304; Kieslich, K. (ed.) (1984) *Biotransformation, Biotechnology*, Vol. 6a, Rehm, H. J. and Reed, G. (eds.), Verlag Chemie, Weinheim]. In isolated cases, mutants that are also derived from wild strains and that are obtained by standard mutagenesis and selection processes are used [see, i.a., U.S. Pat. No. 3,102,080; Seidel, L. and Hörhold, C. (1992) J Basic Microbiol 32:49-55; EP 0322081 B1; U.S. Pat. No. 5,298,398]. Thus, e.g., in biotechnological processes for selective dehydrogenation, the endogenic catalytic activity of different microorganisms, i.a., *Arthrobacter simplex* and *Bacillus sphaericus*, is used [Sedlaczek (1988) Crit Rev Biotechnol. 7:187-236; U.S. Pat. No. 2,837,464; U.S. Pat. No. 3,010,876; U.S. Pat. No. 3,102,080].

It is also known that $\Delta^1$-dehydrogenase genes of *Arthrobacter simplex* [Choi, K. P. et al. (1995) *J Biochem* 117:1043-1049; Molnar, I. et al. (1995) *Mol Microbiol* 15:895-905], *Comamonas testosteroni* [Plesiat, P. et al. (1991) *J Bacteriol* 173:7219-7227] and *Nocardia opaca* [Drobnic, K. et al. (1993) *Biochem Biophys Res Com* 190:509-515; SUISS-PROT AC: Q04616] were cloned, sequenced and functionally characterized. Also, DNA sequences were published from *Mycobacterium tuberculosis* and *Rhodococcus rhodochrous*, and because of their similarity to the above-mentioned $\Delta^1$-dehydrogenase genes, said sequences can be considered as presumable dehydrogenase genes [world wide web at sanger.ac.uk/Projects/M_*tuberculosis*; GenBank AC: 007847].

Limitation of the known biotransformation processes lies in the fact that the latter are in general process optimizations that are concentrated predominantly in the improvement of reaction conditions and process parameters, such as, e.g., type and composition of nutrients, execution of the process, substrate administration, etc. In particular, the processes for selective dehydrogenation have a number of drawbacks, such as, e.g., i) complete reaction of the educt only at very low substrate concentrations [U.S. Pat. No. 3,102,080], ii) long operating times, and iii) the formation of secondary zones— such as, e.g., 11$\alpha$-hydroxyandrosta-1,4-diene-3,17-dione in the reaction of hydrocortisone to form prednisolone, which must be separated by expensive purification processes. These drawbacks result in the fact that the production process is very expensive.

It has now been found that by directed alteration of the microorganisms that catalyze the materials conversion with molecular-biological methods, better, more efficient and purposeful biotransformations of steroid molecules can be achieved. The biotransformation reactions are performed with bacteria that contain plasmids for overexpression of 3-keto steroid-$\Delta^1$-dehydrogenase genes.

The bacteria that are used include in particular representatives of the gram-positive genus *Bacillus*, such as *Bacillus subtilis*, *Bacillus sphaericus*, *Bacillus licheniformis*, *Bacillus lentus* and *Bacillus megaterium*, but also gram-negative representatives, such as *Escherichia coli* and *Pseudomonas* species.

By directed strain development with molecular-biological methods, microorganisms are designed that accelerate and simplify the syntheses of active ingredients, by i) the use of very high substrate concentrations with ii) unaltered operating times being possible, without iii) disruptive secondary zones being developed.

In particular, selective dehydrogenation at 1-position of the steroid skeleton is described here, whereby 3-keto steroid-$\Delta^1$-dehydrogenase genes that are isolated from microorganisms are used.

According to the invention, a process for selective introduction of a double bond into a steroid skeleton by overexpression of dehydrogenases is now described, which is characterized in that a) a dehydrogenase gene is isolated from a bacterium, cloned and amplified, b) promoter and terminator elements of the dehydrogenase gene or other promoter and terminator elements are isolated from the same or another bacterium, cloned and amplified, c) expression plasmids are designed in which the dehydrogenase gene from a), flanked by promoter and terminator sequences of the dehydrogenase gene or by other promoter and terminator elements from b), is contained, d) bacteria are transformed with the expression plasmid that is produced under c), and e) the thus produced bacteria are cultivated, and the selective dehydrogenation in the steroid skeleton is performed with these cultures, whereby i) a high substrate concentration at unaltered operating times is used, and ii) no disruptive secondary zones are produced.

This invention relates in particular to a process for selective introduction of a double bond into a steroid skeleton by overexpression of $\Delta^1$-dehydrogenases, which is characterized in that a) a $\Delta^1$-dehydrogenase gene is isolated from a bacterium, cloned and amplified, b) promoter and terminator elements of the $\Delta^1$-dehydrogenase gene or other promoter and terminator elements are isolated from the same or another bacterium, cloned and amplified, c) expression plasmids are designed, in which the $\Delta^1$-dehydrogenase gene from a), flanked by promoter and terminator sequences of the $\Delta^1$-dehydrogenase gene or by other promoter and terminator elements from b), is contained, d) bacteria are transformed with the expression plasmid that is produced under c), and e) the thus produced bacteria are cultivated, and the selective dehydrogenation in the steroid skeleton is performed with these cultures, whereby
   i) a high substrate concentration at unaltered operating times is used, and
   ii) no disruptive secondary zones are produced.

This invention relates in particular to a process for selective introduction of a double bond in a steroid skeleton by overexpression of 3-keto steroid-$\Delta^1$-dehydrogenases, which is characterized in that
   a) the 3-keto steroid-$\Delta^1$-dehydrogenase gene is isolated from a bacterium, cloned and amplified,
   b) promoter and terminator elements of the 3-keto steroid-$\Delta^1$-dehydrogenase gene or other promoter and terminator elements are isolated from the same or another bacterium, cloned and amplified,
   c) expression plasmids are designed, in which the 3-keto steroid-$\Delta^1$-dehydrogenase gene from a), flanked by promoter and terminator sequences of the 3-keto steroid-$\Delta^1$-dehydrogenase gene or by other promoter and terminator elements from b), is contained,
   d) bacteria are transformed with the expression plasmid that is produced under c), and
   e) the thus produced bacteria are cultivated, and the selective dehydrogenation at 1-position in the steroid skeleton is performed with these cultures, whereby
      i) a high substrate concentration at unaltered operating times is used, and
      ii) no disruptive secondary zones are produced.

The bacteria that are mentioned in process steps a), b) and d) can be among the gram-positive genus *Bacillus*, such as *Bacillus* spec., *Bacillus subtilis*, *Bacillus sphaericus*, *Bacillus megaterium*, *Bacillus licheniformis*, *Bacillus lentus* as well as the gram-positive representatives *Arthrobacter* simplex and *Brevibacterium maris* or the gram-negative representatives *Escherichia coli* and *Pseudomonas* species.

This invention relates in particular to the 3-keto steroid-$\Delta^1$-dehydrogenase gene from *Arthrobacter* simplex according to Seq. ID No. 1, the 3-keto steroid-$\Delta^1$-dehydrogenase gene from *Bacillus sphaericus* with promoter and terminator elements according to Seq. ID No. 9 or Seq. ID No. 10, and the 3-keto steroid-$\Delta^1$-dehydrogenase gene from *Brevibacterium maris* according to Seq. ID No. 12 as well as the correspondingly expressed proteins, such as 3-keto steroid-$\Delta^1$-dehydrogenase from *Bacillus sphaericus* according to Seq. ID No. 11, 3-keto steroid-$\Delta^1$-dehydrogenase from *Brevibacterium maris* according to Seq. ID No. 13 and 3-keto steroid-$\Delta^1$-dehydrogenase from *Arthrobacter* simplex according to Seq. ID. No. 14.

The above-mentioned DNA sequences can be introduced into host cells with suitable plasmids. Suitable host cells or recipients are, e.g., gram-positive bacteria of the genus *Bacillus* that can be used for the overexpression of $\Delta^1$-dehydrogenases with the purpose of dehydrogenating steroid molecules selectively in a biotransformation reaction. In particular, species such as *Bacillus sphaericus* and *Bacillus subtilis* are suitable for this purpose.

The bacteria are also subjects of this invention.

To introduce the inventive DNA sequences into the host cells, plasmids are used that contain at least one of the above-mentioned DNA sequences. In the plasmids, the $\Delta^1$-dehydrogenase genes are provided with suitable promoters and terminators, which are necessary for overexpression in bacteria. Suitable promoter and terminators are, e.g., promoters and terminators of the 3-keto steroid-$\Delta^1$-dehydrogenase gene of *Bacillus sphaericus* according to Seq. ID No. 9, constitutive promoters such as p(veg) or promoters of bacteriophages Φ29 and SPO1, inducible promoters such as p(aprE) or p(sacB) from *Bacillus subtilis*, hybrid promoters such as, e.g., a lacI-controlled SPO1-promoter, terminators of *Escherichia coli* such as t(rrnB) or of *Bacillus subtilis* such as t(senS) or t(senN) [see, i.a., Doi, R. H. (1984) In: Biotechnology and Genetic Engineering Reviews, Vol. 2, Russell, G. E. (ed.), Intercept, Newcastle Upon Tyne, UK, pp. 121-153; Le Grice, S. F. J. et al. (1986) In: *Bacillus Molecular Genetics and Biotechnology Applications*, Ganesan, A. T. and Hoch, J. A. (eds.), Academic Press, New York, 433-445; Mountain, A. (1989) In: *Bacillus*, Harwood, C. R. (ed.), Plenum Press, New York, pp. 73-114; Le Grice, S. F. J. (1990) *Meth Enzymol* 185:210-214; Wang and Doi (1992) In: *Biology of Bacilli: Applications to Industry*, Doi et al. (eds.), Massachusetts, Butterworth-Heinemann, pp. 143-188].

The plasmids are also subjects of this invention.

The plasmids can be used for transformation of bacteria that are capable of overexpression of $\Delta^1$-dehydrogenases.

The invention also relates to DNA sequences with 3-keto steroid-$\Delta^1$-dehydrogenase activity, whose DNA sequences have a homology of more than 80%, especially a homology of more than 90%, and preferably a homology of more than 95%.

The invention also relates to protein sequences with 3-keto steroid-$\Delta^1$-dehydrogenase activity that have a homology of at least 90%, especially a homology of at least 95%.

The invention also relates to promoters, especially the 3-keto steroid-$\Delta^1$-dehydrogenase promoter from *Bacillus sphaericus* with the DNA sequence Seq. ID. No. 9, as well as homologous promoters that have a homology with Seq. ID No. 9 of more than 80%, preferably more than 90%, and especially preferably more than 95%.

The invention also relates to the *Bacillus shaericus* 3-keto steroid-$\Delta^1$-dehydrogenase oligonucleotides according to sequences Seq. ID No. 15, Seq. ID No. 16, Seq. ID No. 17 and Seq. ID No. 18, and the parS oligonucleotides according to sequences Seq. ID No. 19 and Seq. ID No. 20 and use thereof in processes for selective introduction of double bonds into a steroid skeleton.

The DNA sequences and proteins according to the invention can be used for selective dehydrogenation of steroids. The DNA sequences and protein sequences are also subjects of this invention.

Dehydrogenated steroids are, e.g., betamethasone, clobetasone, clocortolone, $\Delta^1$-11β,17α-dihydroxy-6α,9α-difluoro-16α-methylprogesterone, deflazacort, dexamethasone, diflocortolone, fluocinolone acetonide, fluocortolone, hydroxy acid and prednisolone and derivatives of the above-mentioned compounds.

Filings

The bacteria strains that are mentioned in the application can be ordered from the respective filing sites, e.g., from DSM⇒Deutsche Sammlung von Mikroorganismen und Zellkulturen [German Collection of Microorganisms and Cell Cultures] GmbH, Mascheroder Weg 1b, D-38124 Brunswick; ATCC⇒American Type Culture Collection, Rockville, Md., USA; NRRL⇒Northern Utilization Research and Development Division, Peoria, Ill., USA; etc.

To better understand the invention that is based on this invention, first the methods that are used are described.

1. Restrictions

Restrictions of plasmid DNA and genomic DNA were performed in volumes of 15 to 100 μl based on the amount of DNA that was used [1 to 20 μg]. The enzyme concentration was 1 to 5 units of restriction enzyme per μg of DNA. The reaction was performed in a buffer, incubated for one to three hours and subsequently analyzed on an agarose gel [Sambrook et al. (1989) *Molecular Cloning: A Laboratory Manual*, Cold Spring Harbor Laboratory Press, Cold Spring Harbor, N.Y.].

2. Agarose-Gel Electrophoresis

Gel electrophoreses were performed in Minigel-[BioRad], Midi-Widegel-[Biometra] and Maxigel devices [Biometra]. Depending on the separating problem, agarose gels with 0.8% to 4% [w/v] agarose in 0.5×TBE buffer were used. The electrophoresis was carried out with 0.5×TBE as a running buffer. DNA fragments were stained with ethidium bromide and made visible in a transilluminator [Sambrook et al. (1989) *Molecular Cloning: A Laboratory Manual*, Cold Spring Harbor Laboratory Press, Cold Spring Harbor, N.Y.].

3. Elution of DNA from an Agarose Gel

Preparative restriction preparations were separated in agarose gel according to size. The desired volumes were cut out with a scalpel. The DNA fragment to be isolated was recovered with the aid of the "Jetsorb Kit" [Genomed] taking into consideration the instructions of the manufacturer and taken up in TE buffer.

4. Phosphorylation of Oligonucleotides 50 pmol of oligonucleotide was incubated in buffer recommended by the manufacturer in the presence of 0.1 mmol of ATP and 20 units of T4 polynucleotide kinase for 45 minutes at 37° C. An enzyme inactivation was carried out at 68° C. [Sambrook et al. (1989) *Molecular Cloning: A Laboratory Manual*, Cold Spring Harbor Laboratory Press, Cold Spring Harbor, N.Y.].

5. Ligation

For ligation, suitable amounts of dephosphorylated, linearized vector-DNA and fragment-DNA were used in a molar ratio of 1:5. The reaction was carried out in a volume of 10 µl with 1 unit of T4-DNA-ligase in buffer recommended by the manufacturer at 16° C. overnight in a water bath [Sambrook et al. (1989) *Molecular Cloning: A Laboratory Manual*, Cold Spring Harbor Laboratory Press, Cold Spring Harbor, N.Y.].

6. Transformation of *Escherichia coli*

Competent *E. coli* cells were obtained by $CaCl_2$ treatment and stored at −80° C. In general, a 10 µl ligation stock was incubated with 200 µl of competent cells. The transformation stocks were plated on LB agar with the addition of antibiotic necessary in each case and incubated for 16 hours at 37° C. Production of competent cells and a transformation were carried out according to Sambrook et al. (1989) *Molecular Cloning: A Laboratory Manual*, Cold Spring Harbor Laboratory Press, Cold Spring Harbor, N.Y.

7. Transformation of *Bacillus subtilis*

The transformation of *Bacillus subtilis* was carried out according to the two-stage process described by Cutting, S. M. and Vander Horn, P. B. [In: *Molecular Biological Methods for Bacillus* (1990), Harwood, C. R. and Cutting, S. M. (eds.), John Wiley & Sons, Chichester].

8. Transformation of *Bacillus sphaericus*

*Bacillus sphaericus* was transformed by electroporation in a way similar to a process published by Taylor and Burke (1990) [FEMS Microbiol Lett 66:125-128]. The cells were cultured overnight in MM2G medium [0.3% (w/v) meat extract, 0.8% (w/v) yeast extract, 1% (w/v) peptone, 0.2% (w/v) glucose, 0.7% (w/v) NaCl, 7.36 g/l of $K_2HPO_4$, 2.65 g/l of $KH_2PO_4$, 5 ml/l of 100% glycerol, pH 7], 1:20 was transferred into fresh MM2G medium, and it was cultivated for 90 minutes at 37° C. and 250 rpm. The cells were pelletized, washed 3× with 10% glycerol and then taken up in 750 µl of glycerol. 50 µl of cell suspension was mixed in an electroporation cell with plasmid-DNA, incubated on ice, and placed in the electroporation device [Biorad Gene Pulser™] [2.5 kV, 25 µF, 600Ω]. The cells were incubated for regeneration for 90 minutes at 30° C. in MM2G medium and subsequently plated on TBAB agar/5 µg of neomycin [tryptose blood agar base (Difco)] and incubated for 24 hours at 30° C.

9. Plasmid Mini-Preparation from *Escherichia coli*

Mini-preparations were made according to the principle of alkaline cell lysis [Sambrook et al. (1989) *Molecular Cloning: A Laboratory Manual*, Cold Spring Harbor Laboratory Press, Cold Spring Harbor, N.Y.]. Individual colonies were cultured overnight in reagent glasses with 4 ml of LB medium and selection. 2 ml thereof was used for preparation.

10. Plasmid Mini-Preparation from *Bacillus subtilis* and *Bacillus sphaericus*

The preparation of plasmids from *Bacillus subtilis* and *Bacillus sphaericus* was carried out on columns of the Genomed Company ["Jetstar Kit Mini"] according to the protocol specified by the manufacturer. To ensure a complete cell lysis of the cells, the cell pellet that was taken up in buffer E1 was mixed with 5 mg/ml of lysozyme, and the cells were incubated for one hour at 37° C.

11. Plasmid Maxi-Preparation from *Escherichia coli*, *Bacillus subtilis* and *Bacillus sphaericus*

Plasmid maxi-preparation was made with the "Jetstar Kit Maxi" of the Genomed Company. The strains were cultivated overnight in 200 ml of LB medium in the presence of an antibiotic. The preparation of the plasmids was carried out according to the protocol specified by the manufacturer. To ensure a complete cell lysis of *Bacillus subtilis* and *Bacillus sphaericus*, the cell pellets that were taken up in buffer E1 were mixed in addition with 5 mg/ml of lysozyme, and the cells were incubated for one hour at 37° C.

12. Preparation of Genomic DNA from *Arthrobacter* simplex, *Bacillus* species and *Rhodococcus maris*

200 ml of a densely-grown bacteria culture was pelletized and suspended in 11 ml of solution I [50 mmol of Tris-HCl, pH 8; 50 mmol of EDTA; 1% (v/v) Triton x-100, 200 µg/ml of Rnase]. The suspension was mixed with lysozyme [5 mg/ml→*A. simplex*, *B.sp.*/15 mg/ml→*R. maris*] and 500 µl of proteinase K [20 mg/ml] and incubated for >30 minutes at 37° C. 4 ml of solution II [3 M guanidinium-hydrochloride, 20% (v/v) Tween] was subsequently added thereto, and the stock was incubated for 30 minutes at 50° C. Undissolved particles were pelletized and discarded. The chromosomal DNA that was dissolved in the lysate was purified by anionic exchange chromatography ["Jetstar Kit Maxi" of the Genomed Company, see the protocol specified by the manufacturer].

13. Polymerase Chain Reaktion

The reaction conditions for the PCR were optimized for each individual case. In general, 0.1 to 0.5 µg of template-DNA, 10 mmol of dNTPs, 50 pmol each of 5'- and 3'-primer as well as 2.5 units of Pwo-polymerase [Boehringer Mannheim] were combined in the buffer recommended by the manufacturer in 100 µl of total volume. Depending on the template-DNA, the stock was added up to 10% DMSO. The PCR was performed in a "Biometra Trio Thermoblock." The temperature profile was newly modified for each requirement. The annealing temperature varied between 50° C. [less stringent conditions] and 65° C. [See *PCR 1: A Practical Approach*, McPherson et al. (eds.), Oxford University Press (1991)]

14. Southern Analyses

In agarose gel, DNA that was separated according to size was transferred by the capillary-blot process [Sambrook et al. (1989) *Molecular Cloning: A Laboratory Manual*, Cold Spring Harbor Laboratory Press, Cold Spring Harbor, N.Y.] to positively-charged nylon membranes and linked covalently with the membrane by UV-irradiation.

Hybridizations were performed with digoxigenin-labeled probes. The labeling of the probes was carried out with the "DIG-High-Prime" or the "PCR DIG Probe Synthesis Kit" of Boehringer Mannheim according to the protocol recommended by the manufacturer.

For hybridization, an SDS-phosphate buffer was used [7% SDS (w/v); 0.5 M Na phosphate, pH 7.0]. Depending on the requirements, stringent or less stringent hybridization conditions were selected [Sambrook et al. (1989) *Molecular Cloning: A Laboratory Manual*, Cold Spring Harbor Laboratory Press, Cold Spring Harbor, N.Y.].

The detection of bonded DNA was carried out with a chemiluminescence reagent [CSPD®] of Boehringer Mannheim according to instructions recommended by the manufacturer.

14. Colony Hybridization

The transfer of colonies to Pall BIODYNE® A membranes [1.2 μm and 0.2 μm pore size] was performed according to the process recommended by the manufacturer.

The hybridization was carried out with digoxigenin-labeled probes in the above-indicated SDS-phosphate buffer, and the detection was carried out with a chemiluminescence reagent CSPD® of Boehringer Mannheim ["Pall Bio Support" application information SD1359G].

15. DNA-Sequence Analysis

DNA-sequence analyses were carried out with the GATC® 1500 system. The sequence reactions were performed with the GATC®-BioCycle Sequencing Kit according to the protocol recommended by the manufacturer and analyzed on a 4% polyacrylamide-urea gel [GATC® 1500-system protocol]. The detection was carried out with CSPD® [GATC®-BioCycle Sequencing Kit Protocol].

16. Hydrocortisone/Hydrocortisone-17-acetate→Prednisolone: Working-up and Analysis The culture broth was diluted with the 3× volume of methanol/1% acetic acid, ultrasound-treated and centrifuged off. The supernatant was chromatographed on an ODS-Hypersil column [250×4.6 mm] with an acetonitrile-water gradient at a flow rate of 1 ml/minute.

Sequence of eluants: hydrocortisone, prednisolone, 11β-hydroxyandrosta-1,4-diene-3,17-dione, hydrocortisone-17-acetate, hydrocortisone-21-acetate, prednisolone-21-acetate.

17. 4-Androstene-3,17-dione→Androsta-1,4-diene-3,17-dione: Working-Up and Analysis Isobutyl methyl ketone extracts of the culture broth were analyzed by gas chromatography:

Column 1: 50 m×0.25 mm, Chrompack WCOT CP5 CB, film thickness 0.4 μm

Column 2: 30 m×0.25 mm, hp 1701, film thickness 0.4 μm

Detector: FID

Carrier gas: hydrogen

Preliminary column pressure: 175 kPa

Sequence of the eluants: 4-androstene-3,17-dione, androsta-1,4-diene-3,17-dione

18. Fluocortolone A Acetate→Fluocortolone: Working-Up and Analysis

The culture broth was set at pH 4-6 with acetic acid and then extracted with the 4× volume of isobutyl methyl ketone. The extract was concentrated by evaporation, taken up in chloroform and chromatographed on a Kromasil 100 column [250×4 mm] with an isocratic gradient of chloroform:isooctane: 1,4-dioxane:ethanol:water 1000:100:50:10:2 at a flow rate of 1.2 ml/minute.

Sequence of eluants: fluocortolone A acetate, fluocortolone A, fluocortolone

19. 11β,17α-Dihydroxy-6α,9α-difluoro-16α-methylprogesterone→$\Delta^1$-11β,17α-Dihydroxy-6α,9α-difluoro-16α-methylprogesterone: Workin-Up and Analysis The culture broth was diluted with the 3× volume of methanol/1% acetic acid, ultrasound-treated and centrifuged off. The supernatant was chromatographed on an ODS-Hypersil column [250×4.6 mm] with an acetonitrile-water gradient at a flow rate of 1 ml/minute.

Sequence of eluants: 11β,17α-Dihydroxy-6α,9α-difluoro-16α-methylprogesterone, $\Delta^1$-11β,17α-Dihydroxy-6α, 9α-difluoro-16α-methylprogesterone

20. 11β,21-Dihydroxy-2'-methyl-5'βH-pregn-4-eno[17,16-d]oxazole-3,20-dione→11β,21-Dihydroxy-2'-methyl-5'βH-pregna-1,4-dieno[17,16-d]oxazole-3,20-dione (Deflazacort Alcohol): Working-up and Analysis The culture broth was turraxed and then extracted with the 4× volume of methyl isobutyl ketone. The extract was evaporated to the dry state and taken up in the same volume of chloroform. The sample was applied on a Kromasil-100 column [250×4.6 mm] and chromatographed with diisopropyl ether:dichloroethane:1,4-dioxane:$H_2O$ (250:150:75:4) at a flow rate of 2 ml/minute. Sequence of the eluants: 11β,21-dihydroxy-2'-methyl-5'βH-pregn-4-eno[17,16-d]oxazole-3,20-dione, 11β,21-dihydroxy-2'-methyl-5'βH-pregna-1,4-dieno[17,16-d]oxazole-3,20-dione (deflazacort alcohol)

DESCRIPTION OF THE FIGURES

FIGS. 1*a*/1*b* shows the alignment of all known 3-keto steroid-$\Delta^1$-dehydrogenases [CLUSTAL, W. Algorithmus, Thompson, J. D. et al. (1994) *Nucleic Acids Res* 22:4673-4680].

In the figure:

Bm3os-delta1-DH means *Brevibacterium maris* 3-oxo steroid-$\Delta^1$-dehydrogenase (SEQ ID NO: 23)

Rr3os-delta1-DH means *Rhodococcus rhodochrous* 3-oxo steroid-$\Delta^1$-dehydrogenase (SEQ ID NO: 24)

As3os-delta1-DH means *Arthrobacter* simplex 3-oxo steroid-$\Delta^1$-dehydrogenase (SEQ ID NO: 25)

Bs3os-delta1-DH means *Bacillus sphaericus* 3-oxo steroid-$\Delta^1$-dehydrogenase (SEQ ID NO: 26)

Mt3os-delta1-DH means *Mycobacterium tuberculosis* 3-oxo steroid-$\Delta^1$-dehydrogenase (SEQ ID NO: 27)

No3os-delta1-DH means *Nocardia opaca* 3-oxo steroid-$\Delta^1$-dehydrogenase (SEQ ID NO: 28)

Ct3os-delta1-DH means *Comamonas testosteroni* 3-oxo steroid-$\Delta^1$-dehydrogenase (SEQ ID NO: 29)

Number of perfect matches * 61⇒10.34%

Number of high similarity : 48⇒8.14%

Number of low similarity . 54⇒9.15%

Bm3os-delta1-DH [this work]; Rr3os-delta1-DH [GenBank AC: AB007847]; As3os-delta1-DH [Molnar, I. et al. (1995) *Mol Microbiol* 15:895-905; GenBank AC: D37969]; Bs3os-delta1-DH [this work]; Mt3os-delta1-DH [cosmid Z82098, complement 16520 . . . 18211;

http://www.sanger.ac.uk/M_tuberculosis]; No3os-delta1-DH [Drobnic, K. et al. (1993) *Biochem Biophys Res Comm* 190:509-515; SUISS-PROT AC: Q04616]; Ct3os-delta1-DH [Plesiat, P. et. (1991) *J Bacteriol* 173: 7219-7227; SUISS-PROT AC: Q06401].

Figure 2:
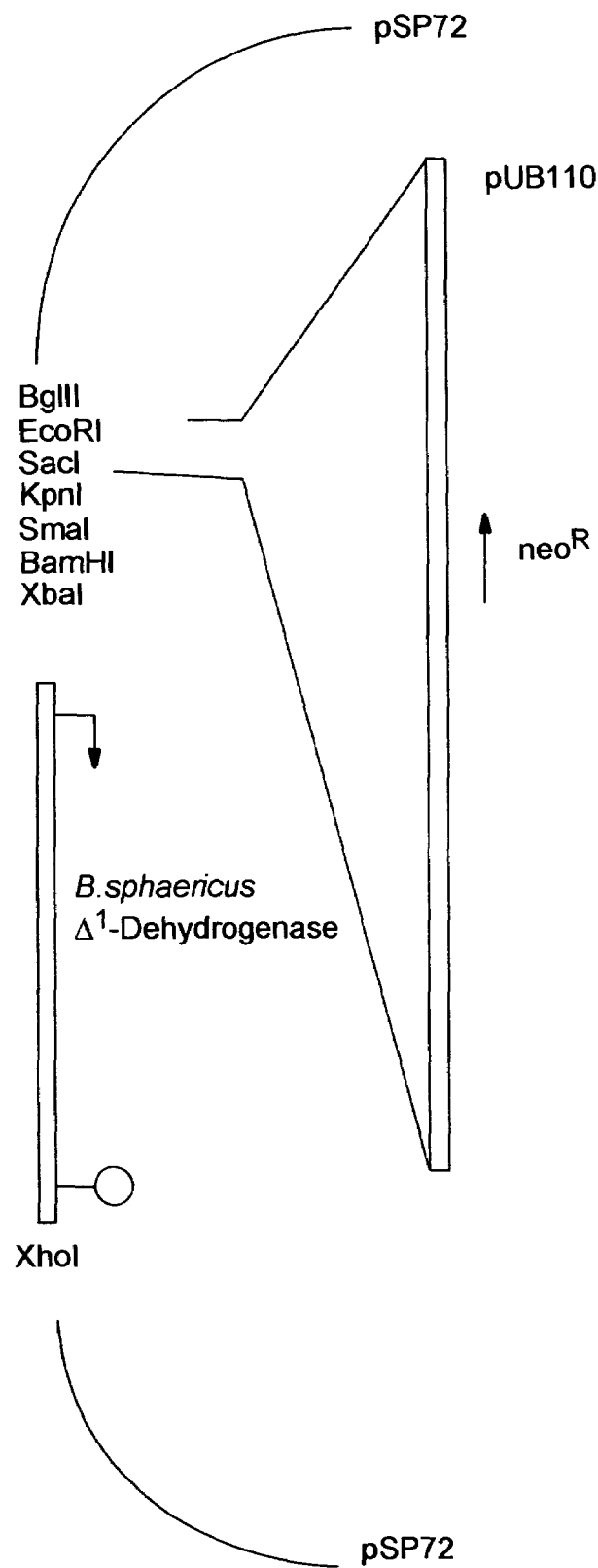

FIG. 2 shows expression plasmid TS#196

Figure 3:
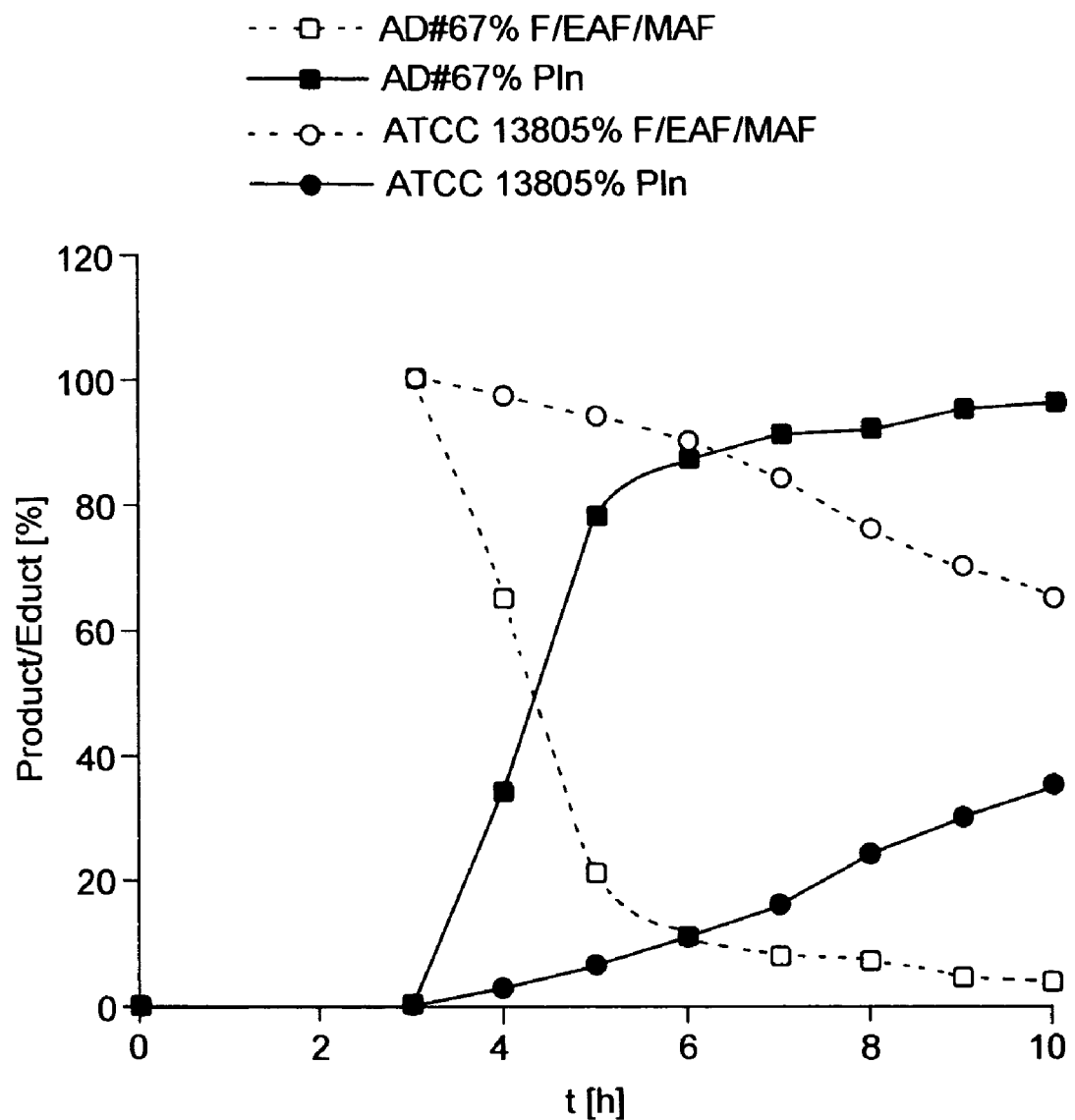
Figure 4:
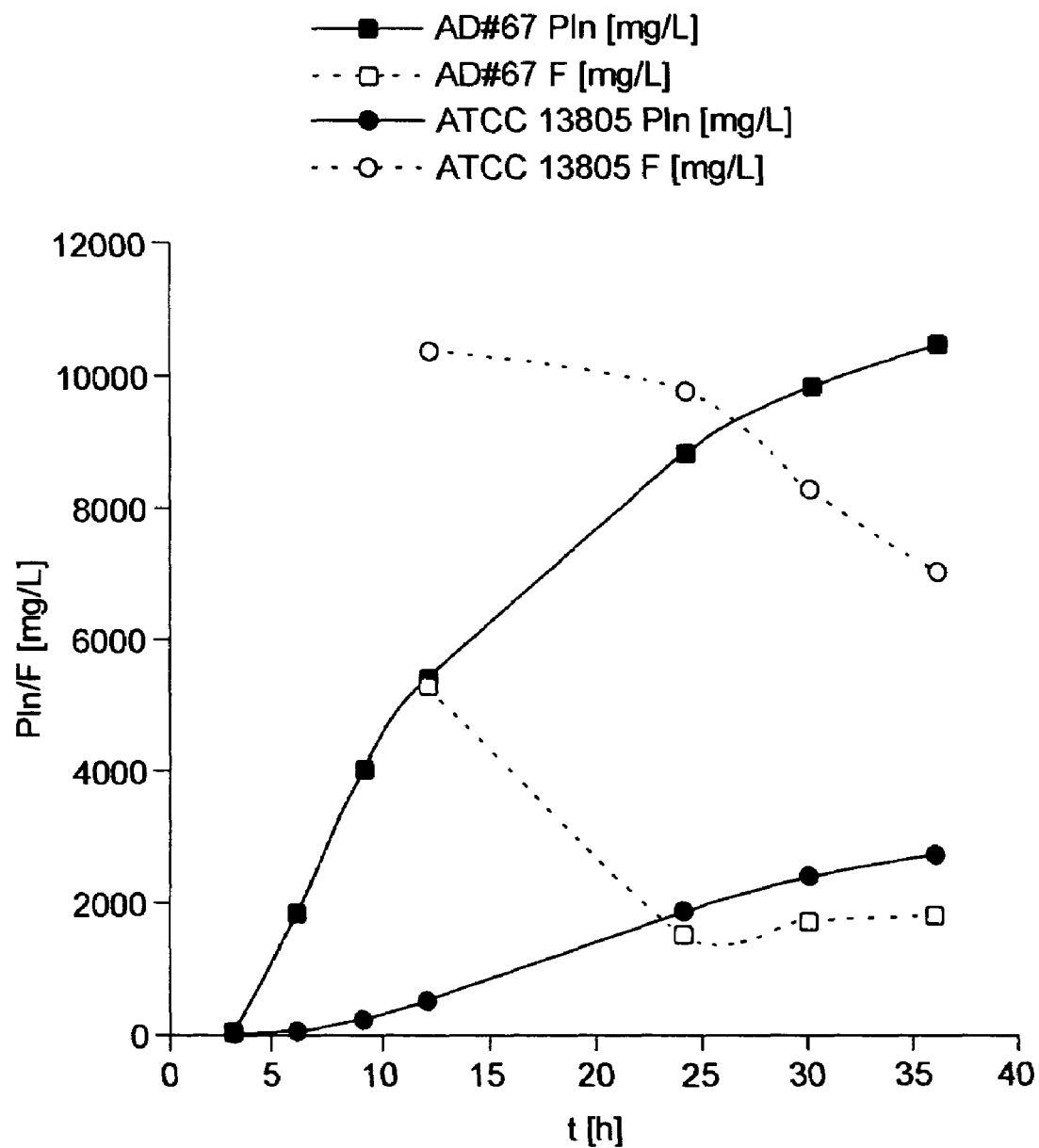
Figure 5:
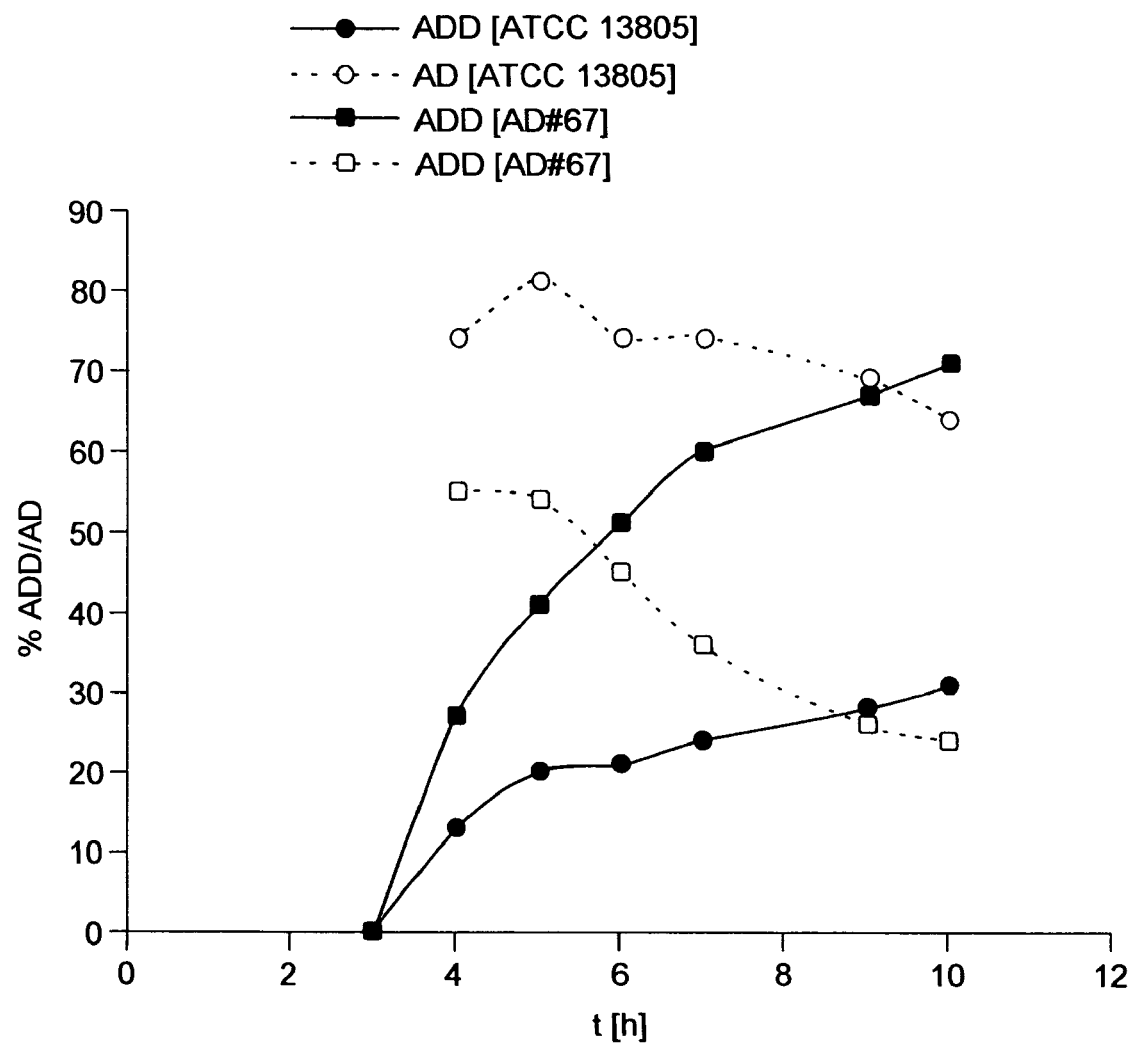
Figure 6:
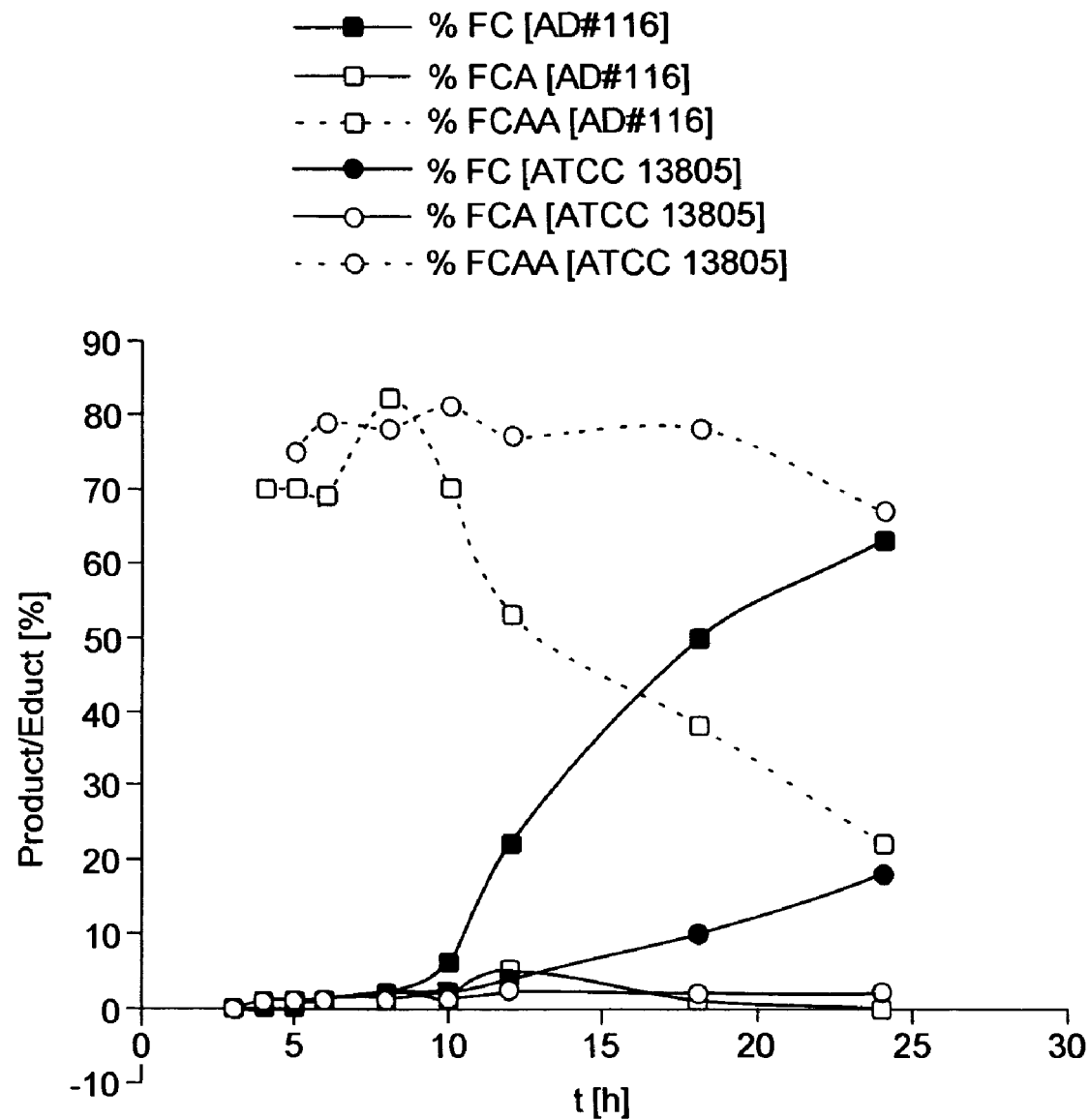
Figure 7:
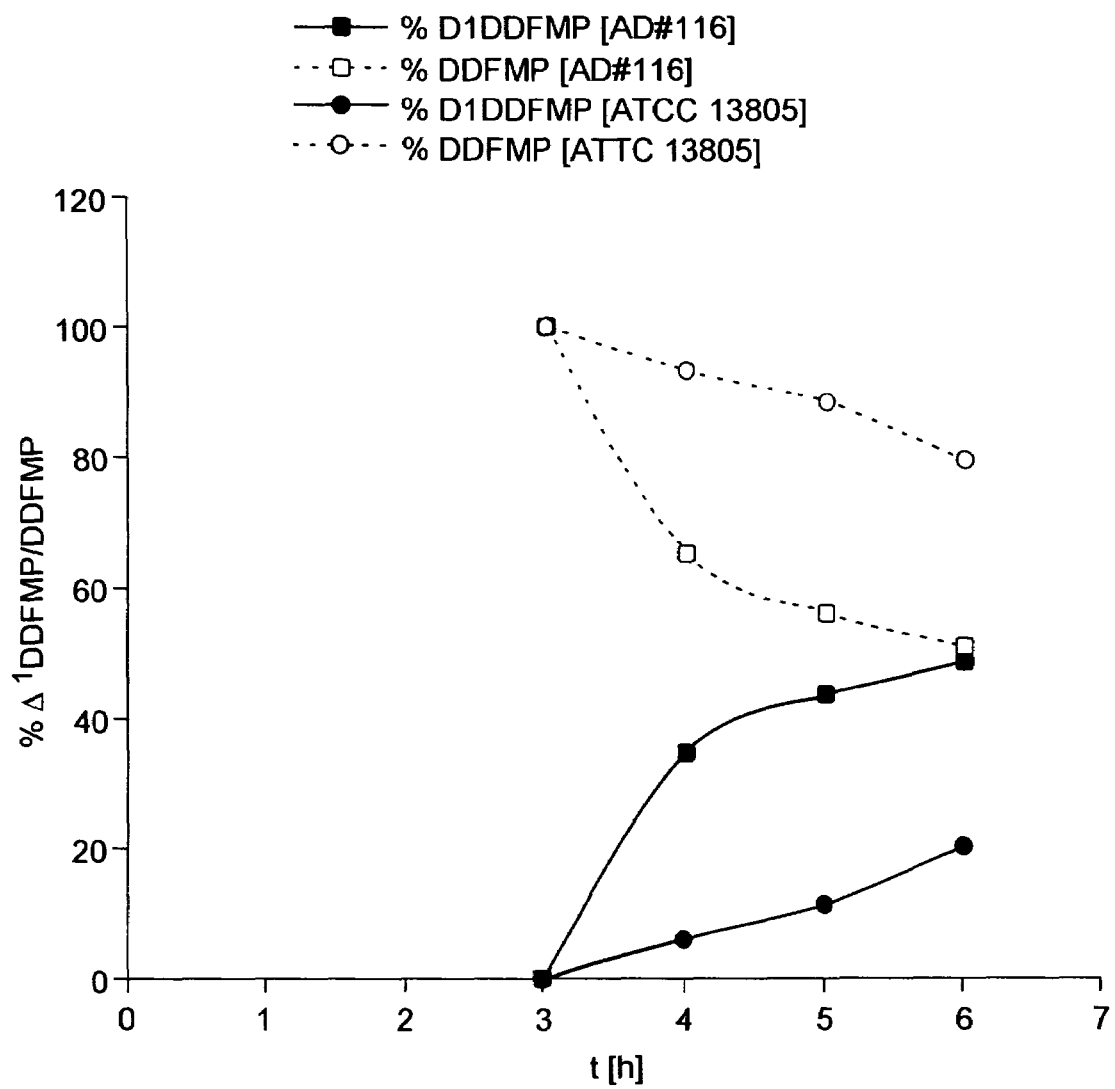
Figure 8:
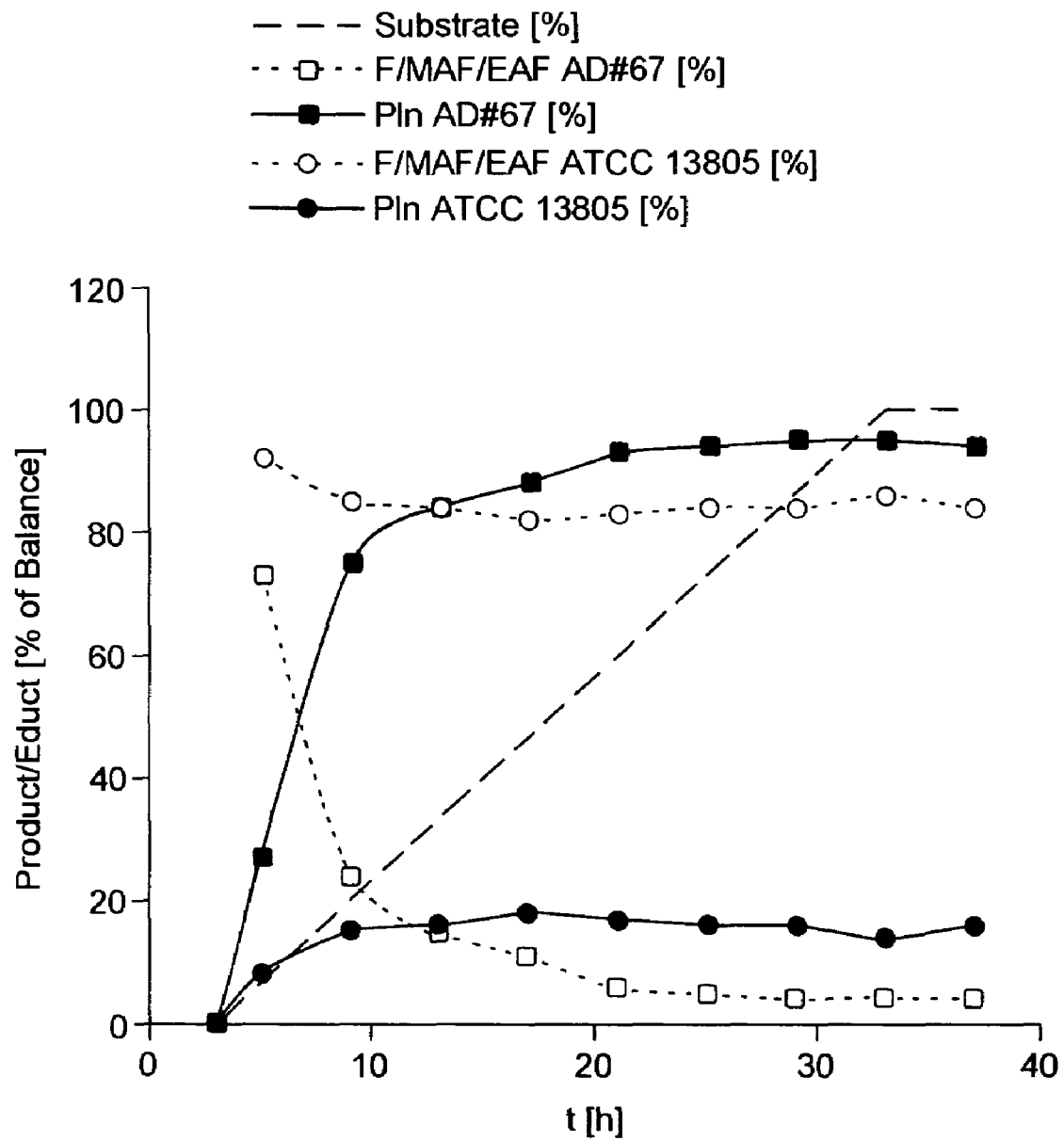

FIG. 3 shows the reaction of EAF/MAF/F to form Pln [1 g/l]: cf. strain AD#67 with *Bacillus sphaericus* ATCC 13805
In the figure:
EAF⇒Hydrocortisone-21-acetate
MAF⇒Hydrocortisone-17-acetate
F⇒Hydrocortisone
Pln⇒Prednisolone FIG. 4 shows the reaction of EAF/MAF/F to form Pln [10 g/l]: cf. strain AD#67 with *Bacillus sphaericus* ATCC 13805
In the figure:
EAF⇒Hydrocortisone-21-acetate
MAF⇒Hydrocortisone-17-acetate
F⇒Hydrocortisone
Pln⇒Prednisolone FIG. 5 shows the reaction of AD to form ADD [1 g/l]: cf. strain AD#67 with *Bacillus sphaericus* ATCC 13805
In the figure:
AD⇒4-Androstene-3,17-dione
ADD⇒Androsta-1,4-diene-3,17-dione FIG. 6 shows the reaction of FCAA to form FC [1 g/l]: cf. strain AD#116 with *Bacillus sphaericus* ATCC 13805
In the figure:
FCAA⇒Fluocortolone A acetate
FCA⇒Fluocortolone A
FC⇒Fluocortolone FIG. 7 shows the reaction of DDFMP to form $\Delta^1$-DDFMP [0.2 g/l]: cf. strain AD#116 with *Bacillus sphaericus* ATCC 13805
In the figure:
DDFMP⇒11β,17α-Dihydroxy-6α,9α-difluoro-16α-methylprogesterone
$\Delta^1$-DDFMP⇒$\Delta^1$-11β,17α-Dihydroxy-6α,9α-difluoro-16α-methylprogesterone FIG. 8 shows the conversion of EAF/MAF/F to Pln in 10 l of fermenter [20 g/l] Cf. strain AD#67/*Bacillus sphaericus* ATCC 13805 For the meaning of the abbreviations, see above.

Figure 9:
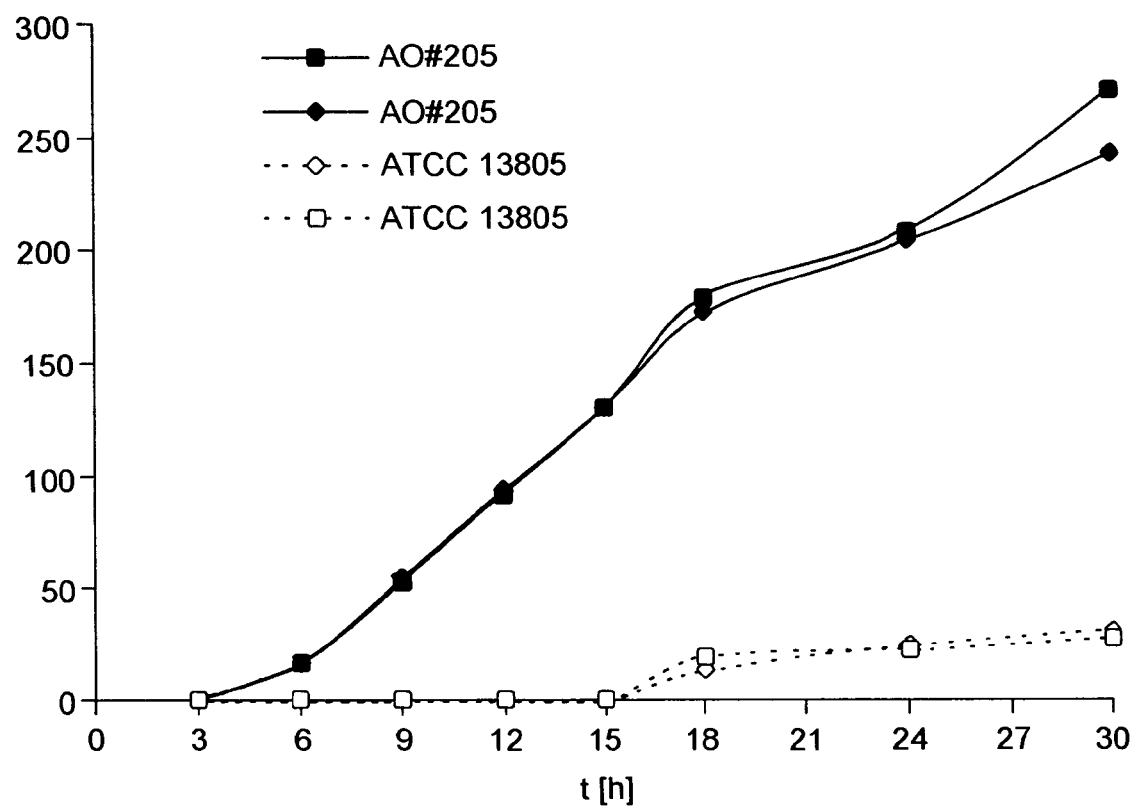

FIG. 9 shows the reaction of 11β,21-dihydroxy-2'-methyl-5'βH-pregn-4-eno[17,16-d]oxazole-3,20-dione to form 11β, 21-dihydroxy-2'-methyl-5'βH-pregna-1,4-dieno[17,16-d] oxazole-3,20-dione (deflazacort alcohol) [1 g/L]: cf. strain AO#205 with *Bacillus sphaericus* ATCC 13805

The cloning, isolation and construction examples below describe the biological feasibility of the invention, without limiting the latter to the examples.

EXAMPLE 1

Cloning of the 3-Keto Steroid-$\Delta^1$-Dehydrogenase Genes from Various Species 1.1 From *Arthrobacter* simplex ATCC 6946

To isolate the 3-keto steroid-$\Delta^1$-dehydrogenase gene from *Arthrobacter* simplex ATCC 6946, the open reader frame was amplified in a PCR reaction with the primer pair 2026

[5' CGG GAT CCA TGG ACT GGG CAG AGG AGT ACG ACG TAC TGG TGG$_{1435-1468}$] (SEQ ID NO: 4) and 2027 [5' CGG AAT TCT CAT CGC GCG TCC TCG GTG CCC ATG TGC CGC ACG$_{2982-2949}$] (SEQ ID NO: 5) from genomic DNA of *Arthrobacter* simplex. The amplified gene was cloned as an NcoI-EcoRI fragment in the corresponding interfaces of vector pTrc99A [Pharmacia] or as a BamHI-EcoRI fragment in the corresponding interfaces of plasmid pSP72 [Promega]. The gene sequence was verified with a GATC® 1500 Sequencer [GATC].

1.2 From *Bacillus sphaericus* ATCC 13805

To isolate the 3-keto steroid-$\Delta^1$-dehydrogenase gene from *Bacillus sphaericus* ATCC 13805, a homologous probe from genomic DNA of *Bacillus sphaericus* was isolated with use of degenerated primers in a PCR reaction: under less stringent conditions, a 1463 bp fragment was amplified with the primer pair 2048 [5' GAA TRY GAT NTW NTW GTW GYW GGW WSW GG] (SEQ ID NO: 15) and 2054 [5' NAR NCC NCC YTT NGT NCC] (SEQ ID NO: 16) and cloned in pCR-Script™ Amp SK(+) [Stratagene]. With the insert as a DNA probe, overlapping genomic clones from a DNA library, which had been produced with the use of Zero Background™/Kan Cloning Kits [Invitrogen], were isolated. The sequence of the *Bacillus sphaericus* 3-keto steroid-$\Delta^1$-dehydrogenase gene was determined with a GATC® 1500 sequencer [GATC]. The protein sequence derived from the gene sequence is 34% identical to the sequence of the 3-keto steroid-$\Delta^1$-dehydrogenase from *Comamonas testosteroni*. The similarity is 54%. A 34% identity and a 54% similarity exist in the 3-keto steroid-$\Delta^1$-dehydrogenase from *Arthrobacter* simplex.

1.3 From *Brevibacterium maris* ATCC 21111

To isolate the 3-keto steroid-$\Delta^1$-dehydrogenase gene from *Brevibacterium maris* ATCC 2111, first heterologous DNA probes were isolated from the 3-keto steroid-$\Delta^1$-dehydrogenase gene of *Arthrobacter* simplex and DIG-labeled: a 109 bp fragment [2066-2175] was amplified with the primer pair 2017 [GAC GCC GTA CTT CTG GCG GAG CTC GTC ATT GGC C$_{2175-2142}$] (SEQ ID NO: 3) and 2032 [CGA TCG TCG AGA CCG ACG G$_{2066-2084}$] (SEQ ID NO: 6), a 190 bp fragment [1428-1618] was amplified with the primer pair 2016 [GAT CAC GAT GGA CTG GGC AGA GGA GTA CGA CG$_{1428-1459}$] (SEQ ID NO: 2) and 2055 [GCA GCA CCG GGT TCG CGG GGA ACC AGG$_{1618-1592}$] (SEQ ID NO: 7), and a 747 bp fragment [1428-2175] was amplified with the primer pair 2016 and 2017. In Southern analyses, subsequent specific binding of the above-mentioned probes to *Brevibacterium maris* DNA was detected. The conditions were used to identify clones with 3-keto steroid-$\Delta^1$-dehydrogenase gene sequences in a DNA library of *Brevibacterium maris*, which had been produced with use of Zero Background™/Kan Cloning Kits [Invitrogen]. In this connection, two overlapping clones were identified. The sequence of the *Brevibacterium maris* 3-keto steroid-$\Delta^1$-dehydrogenase gene was determined. The protein sequence derived from the gene sequence is 28% identical to the sequence of the 3-keto steroid-$\Delta^1$-dehydrogenase from *Comamonas testosteroni*. The similarity is 44%. A 72% identity and an 83% similarity exist in the 3-keto steroid-$\Delta^1$-dehydrogenase from *Arthrobacter* simplex.

A comparison of all known 3-keto steroid-$\Delta^1$-dehydrogenases, including new sequences that are described here, yields—relative to the length of the consensus, an identity of only 10% and a similarity of only 18% [FIG. 1].

1.4 From *Mycobacterium* species NRRL B-3683

For cloning the 3-keto steroid-$\Delta^1$-dehydrogenase gene from *Mycobacterium* species NRRLB-3683, first, analogously to the above, binding to *Mycobacterium* sp. DNA was detected with the described DNA probes, and the gene was then isolated from a genomic DNA library.

1.5 From *Mycobacterium* species NRRL B-3805

For cloning the 3-keto steroid-$\Delta^1$-dehydrogenase gene from *Mycobacterium* species NRRLB-3805, first binding to *Mycobacterium* sp. DNA was detected analogously to the above with the described DNA probes, and the gene was then isolated from a genomic DNA library.

EXAMPLE 2

Isolating and Characterizing the Promoter and Terminator Sequences

As regulatory sequences for the overexpression of the 3-keto steroid-$\Delta^1$-dehydrogenase genes, promoter and terminator elements of the 3-keto steroid-$\Delta^1$-dehydrogenase gene from *Bacillus sphaericus* were used. Both elements were isolated and characterized in line with the cloning of the gene.

The promoter at position 84 bp or 61 bp above the startcodon contains two hexanucleotides [TTGACT$_{-84\ to\ -79}$/TATACT$_{-61\ to\ -56}$], which correspond, with a deviation in each case, to the consensus of bacterial promoters [-10/-35 Box]. The distance from 17 nucleotides of the two elements to one another corresponds exactly to the bacterial consensus [see Record, M. T. et al. (1996) In: *Escherichia coli and Salmonella*, Neidhardt, F. C. (ed.), 2$^{nd}$ Edition, ASM Press, Washington D.C., Vol. 1, pp. 792-821].

16 bp above the startcodon lies a ribosome-binding site that is typical of *Bacillus* [AGGGAGG$_{-16\ to\ -10}$; Band, L. and Henner, D. J. (1984) *DNA* 3: 17-21].

Promoter activity was detected for fragments from position -126 [SalI] to position -28 [ClaI] and from position -258 [PstI] to position -28 [ClaI] in lacZ assays.

9 bp behind the stopcodon is a palindrome [AAGCCCT-TCCT$_{1698-1708}$ (SEQ ID NO: 21)/AGGAAGGGCT$_{1731-1741}$ (SEQ ID NO: 22)], which acts as a ρ-independent terminator [see Richardson, J. P. and Greenblatt, J. (1996) In: *Escherichia coli and Salmonella*, Neidhardt, F. C. (ed.), 2$^{nd}$ Edition, ASM Press, Washington D.C., Vol. 1, pp. 822-848].

In principle, other promoters and terminators can also be used [see, i.a., Doi, R. H. (1984) In: Biotechnology and Genetic Engineering Reviews, Vol. 2, Russell, G. E. (ed.), Intercept, Newcastle Upon Tyne, UK, pp. 121-153; Le Grice, S. F. J. et al. (1986) In: *Bacillus Molecular Genetics and Biotechnology Applications*, Ganesan, A. T. and Hoch, J. A. (eds.), Academic Press, New York, 433-445; Mountain, A. (1989) In: *Bacillus*, Harwood, C. R. (ed.), Plenum Press, New York, pp. 73-114; Le Grice, S. F. J. (1990) *Meth Enzymol* 185:210-214; Wang and Doi (1992) In: *Biology of Bacilli: Applications to Industry*, Doi et al. (eds.), Massachusetts, Butterworth-Heinemann, pp. 143-188].

EXAMPLE 3

Construction of Expression Plasmids

For the production of an expression plasmid, first a "shuttle" plasmid that consists of pSP72 [Promega] and portions of pUB110 [McKenzie et al. (1986) *Plasmid* 15:93-103] was designed. To this end, pUB110 was cleaved with EcoRI and PvuII, and the resulting 3.6 kb fragment was inserted in the EcoRI and EcoRV interfaces of pSP72. The 3-keto steroid-$\Delta^1$-dehydrogenase gene of *Bacillus sphaericus*, flanked by promoter and termination sequences [Position -126 (SalI) to Position 1861 (ScaI)], was ligated as anXbaI-ScaI fragment in the XbaI and PvuII interfaces of the above-described "shuttle" vector [→TS#196, see FIG. 2].

A second expression plasmid carries a modified $\Delta^1$-dehydrogenase gene promoter p($\Delta^1$)$_{mut}$: By PCR-mutagenesis, in each case a base was exchanged in the -35 [TTGACT→TTGACA] and in the -10 Box [TATACT→TATAAT] to achieve an exact correspondence to the consensus of bacterial promoters. For this purpose, the promoter was first amplified with the mutagenesis primer 2089$_{mut}$ [CCA TCG ATG AAT CTG GTC TTC CTA TTA AAA ATT ATA GAA TTA AAC TAA TAT TCT GTC AAT TTT TCC$_{-29\ to\ -91}$] (SEQ ID NO: 17) and primer 2090 [CAT GAC AAA ATT ATT TGA TTT AAT CAC$_{-258\ to\ -284}$] (SEQ ID NO: 18) and inserted as a PstI-ClaI fragment into the corresponding interfaces of pBluescript II KS(+). The mutations were verified by sequence analysis. p($\Delta^1$)$_{mut}$ was cut out as an XbaI-ClaI fragment and ligated in the corresponding interfaces of TS#196. In this connection, the wt promoter was exchanged for p($\Delta^1$)$_{mut}$ [→TS#251].

In addition, two other plasmids carry a plasmid-stabilizing signal, parS [Lin, D. C. and Grossman, A. D. (1998) *Cell* 92:675-685]. The latter was cloned via two oligonucleotides that are complementary to one another, 2091$_{parS}$ [GAT CCT GTT CCA CGT GAA ACA G] (SEQ ID NO: 19) and 2092$_{parS}$ [GAT CCT GTT TCA CGT GGA ACA G] (SEQ ID NO: 20), in the BamHI interface of TS#196 [→AD#82] and TS#251 [→TS#255].

For expression in *Escherichia coli* DH5α [=DSM 6897], the 3-keto steroid-$\Delta^1$-dehydrogenase gene of *Bacillus sphaericus*, flanked by promoter and termination sequences, was cloned as a 2865 bp SalI-partial Sau3A fragment [position -126 to position 2739] in the plasmid pZErO™-2 that is cut with BamHI and XhoI and transformed into *Escherichia coli* DH5α [→plasmid MS#46 or strain MS#46$_{MS\#46}$].

EXAMPLE 4

Production of Recombinant Strains of the Genus *Bacillus* for the Introduction of a $\Delta^1$-Dehydrogenation on the Steroid Expression plasmids TS#196, TS#251, AD#82 and TS#255 were transformed into *Bacillus subtilis* DSM 402 [Deutsche Stammsammlung für Mikroorganismen [German Strain Collection for Microorganisms], Brunswick] and *Bacillus sphaericus* ATCC 13805. *Bacillus subtilis* and *Bacillus sphaericus* are gram-positive, apathogenic organisms. They are simple to cultivate. In contrast to *Bacillus sphaericus*, *Bacillus subtilis* is well characterized in molecular-genetic terms. There are a number of examples for the heterologous expression and secretion of proteins for the production of recombinant gene products [Wang and Doi (1992) In: *Biology of Bacilli: Applications to Industry*, Doi et al. (eds.), Massachusetts, Butterworth-Heinemann, pp. 143-188]. Suitable promoters and terminators are also described here.

With some of the recombinant strains, reactions of a mixture of hydrocortisone [F], hydrocortisone-17-acetate [MAF] and hydrocortisone-21-acetate [EAF] to form prednisolone [Pln] were performed by way of example in a shaking flask. In addition to starting substances F, MAF and EAF as well as the desired product Pln, the formation of prednisolone-21-acetate [Pln-21-acetate] and the undesirable secondary zone 11β-hydroxyandrosta-1,4-diene-3,17-dione [11β-OH-ADD] was also tracked. To demonstrate the reaction potential of the recombinant strains, the process was performed at substrate concentrations in which *Bacillus sphaericus* ATCC 13085 forms no more than 20% Pln.

The strains AD#67$_{TS\#196}$, AD#94$_{TS\#251}$, AD#95$_{TS\#255}$, AD#96$_{TS\#255}$, AD#116$_{TS\#251}$, and AO#205$_{TS\#196}$ are produced from *Bacillus sphaericus* ATCC 13085 and in each case contain the indicated expression plasmid. Strains AD#89$_{TS\#196}$ and AD#90$_{TS\#196}$ are produced from *Bacillus subtilis* DSM 402 and in each case contain the indicated expression plasmid.

The following reaction examples describe the microbiological feasibility of the invention, without the latter being limited to the examples.

EXAMPLE 1

Reaction of EAF/MAF/F to Form Pln

*Bacillus sphaericus* ATCC 13805, AD#67$_{TS\#196}$, AD#94$_{TS\#251}$, AD#95$_{TS\#255}$, AD#96$_{TS\#255}$, AD#116$_{TS\#251}$, *Bacillus subtilis* DSM 402, AD#89$_{TS\#196}$, AD#90$_{TS\#196}$, *Escherichia coli* DH5α DSM 6897 and MS#46$_{MS\#46}$ were cultivated in LB medium [Sambrook et al. (1989) *Molecular Cloning: A Laboratory Manual*, Cold Spring Harbor Laboratory Press, Cold Spring Harbor, N.Y.] in the presence of 5 μg/ml of neomycin [*Bacillus sphaericus* derivatives], 50 μg/ml or 100 μg/ml of kanamycin [*Escherichia coli* or *Bacillus subtilis* derivatives] or without the addition of an antibiotic [wt-strains] at 37° C. and 220 rpm. In the reaction of EAF/MAF/F to form Pln, the inoculation material 1:10 in fresh LB medium was converted without the addition of antibiotic, and the culture was shaken as above. In principle, any other medium in which the organism can grow can also be used. Substrate was added after 3 hours. After 24 hours, the flasks were removed, and educts and product(s) were extracted and HPLC-analyzed [see Table 1; reaction diagram, see below]. *Bacillus subtilis* DSM 402 and *Escherichia coli* DH5α, as expected, do not show any reaction, *Bacillus sphaericus* ATCC 13805 forms less than 20% product after 24 hours, while all recombinant strains of the genus *Bacillus* [AD#67$_{TS\#196}$, AD#94$_{TS\#251}$, AD#95$_{TS\#255}$, AD#96$_{TS\#255}$, AD#89$_{TS\#196}$ and AD#90$_{TS\#196}$] produce more than 80% Pln in the same period. A degradation of substrate or product over 48 hours could not be observed.

All tests that are described below were performed by way of example with AD#67$_{TS\#196}$ or AD#116$_{TS\#251}$. As a standard, *Bacillus sphaericus* ATCC 13805 was used. The tests show the reaction activity, increased by a multiple, of the above-mentioned recombinant strains with respect to $\Delta^1$-dehydrogenations on the steroid molecule.

EXAMPLE 2

Kinetics of the Reaction of EAF/MAF/F to Form Pln [1 g/l]

First, a $\Delta^1$-dehydrogenation in the example of a reaction of EAF/MAF/F to form Pln was performed analogously to the above at a substrate concentration of 1 g/l in a shaking flask [LB medium, 37° C., 220 rpm]. The addition of substrate was carried out after 3 hours. To be able to track the course of the reaction, samples were taken after 4, 5, 6, 7, 8, 9, 10, 11, 12 and 24 hours, and educts and products were extracted and HPLC-analyzed. While the strain ATCC 13805 requires 24 hours to convert the substrate completely into Pln, strain AD#67 has already formed the corresponding amount of Pln after <10 hours [FIG. 3; reaction diagram, see below].

EXAMPLE 3

Kinetics of the Reaction of EAF/MAF/F to Form Pln [10 g/l]

The same test was performed at a substrate loading of 10 g/l. The substrate was added after 3 hours, samples were taken after 6, 9, 12, 24, 30 and 36 hours, and the steroids were extracted and analyzed. After 6 hours, the ATCC 13085 culture has only 1% Pln, while the strain AD#67 has already formed >15% product. After 12 hours, strain AD#67 has already converted more than 50% of the substrate into Pln; strain TCC 13805, however, has converted only 5% [FIG. 4; reaction diagram, see below].

The high reaction activity of strain AD#67 is not limited to the process for the production of prednisolone from EAF/MAF/F but rather applies in general to the introduction of $\Delta^1$ into a steroid molecule.

EXAMPLE 4

Conversion of 4-Androstene-3,17-dione [AD] into Androsta-1,2-diene-3,17-dione [ADD]

The conversion of AD into ADD by strain AD#67 or strain ATCC 13805 was studied analogously to the above in a shaking flask [LB medium, 37° C., 220 rpm]. The substrate was added after 3 hours, and samples were taken after 4, 5, 6, 7, 9 and 10 hours. As in the conversion of MAF/F into Pln, the product formation is carried out considerably faster in the case of fermentation with strain AD#67 than with use of strain ATCC 13805. After 10 hours, *Bacillus sphaericus* ATCC 13805 has converted less than 30% of the substrate to ADD, while in strain AD#67 at this time, already more than 70% of product could be isolated [FIG. 5].

EXAMPLE 5

Reaction of Fluocortolone A Acetate [FCAA] to Form Fluocortolone [FC]

Fluorinated steroids are also dehydrogenated by recombinant strains considerably more efficiently in 1-position than was heretofore possible with the available bio-catalysts. This shows the conversion of FCAA to FC analogously to the above in a shaking flask by AD#116 in comparison to *Bacillus sphaericus* ATCC 13805 [FIG. 6; reaction diagram, see below].

EXAMPLE 6

Reaction of 11β,17α-Dihydroxy-6α,9α-difluoro-16α-methylprogesterone [DDFMP] to Form $\Delta^1$-11β,17α-Dihydroxy-6α,9α-difluoro-16α-methylprogesterone [$\Delta^1$DDFMP]

The conversion of DDFMP to $\Delta^1$DDFMP analogously to the above-mentioned examples is also carried out considerably more efficiently with AD#116 than with *Bacillus sphaericus* ATCC 13805 [FIG. 7, reaction diagram, see below].

EXAMPLE 7

Conversion of EAF/MAF/F to Form Pln in a 10 l Fermenter [20 g/l] Cf. Strain AD#67/*Bacillus sphaericus* ATCC 13805

The $\Delta^1$-dehydrogenation capacity of strain AD#67 was tested in comparison to *Bacillus sphaericus* ATCC 13805 in the example of EAF/MAF/F→Pln in 10 l of fermenter. The reaction was performed in a 20× higher substrate loading. The culture of the inoculation material was carried out in a first step overnight at 37° C. and 220 rpm in LB medium in the presence of 5 µg/ml of neomycin [AD#67] or without the addition of an antibiotic [ATCC 13805]. Subsequently, the overnight culture 1:100 was converted into a 1000 ml intermediate culture and shaken for 9 hours at 37° C. and 220 rpm to an optical density of 2.4. The fermentation was carried out in LB medium without the addition of an antibiotic. In principle, however, any other medium in which the organism can grow can be used. After 3 hours, the substrate was added continuously for 30 hours. The pH was kept at 8. In the course of the fermentation, samples were taken and tested for the content of product and educt. The fermentation profile shows that *Bacillus sphaericus* ATCC 13805 cannot surmount substrate concentrations of this order of magnitude: the reaction stops when more than 80% substrate remains. The conversion capacity of strain AD#67, however, is considerable: Shortly after the substrate application phase has ended, the reaction is almost fully [>98%] completed [FIG. 8]. The conversion activity of strain AD#67 is approximately 0.6 g/l per hour. Strain ATCC 13805 shows, however, an activity of 0.1 g/l per hour. In any case, disruptive secondary zones such as, e.g., 11-β-OH-ADD, were observed in traces. The crystal yield of Pln was approximately over 80% of theory and corresponds to the value that is achieved in conventional processes [reaction diagram, see below].

EXAMPLE 8

Reaction of 11β,21-Dihydroxy-2'-methyl-5'βH-pregn-4-eno[17,16-d]oxazole-3,20-dione to Form 11β,21-dihydroxy-2'-methyl-5'βPH-pregna-1,4-dieno[17,16-d]oxazole-3,20-dione (deflazacort alcohol)

The conversion of 1 g/l of 11β,21-dihydroxy-2'-methyl-5'βH-pregn-4-eno[17,16-d]oxazole-3,20-dione to deflazacort alcohol in a shaking flask analogously to the above-mentioned examples is carried out significantly more efficiently with AO#205 than with *Bacillus sphaericus* ATCC 13805 [FIG. 9; reaction diagram, see below]. Unlike in the above, a medium that consists of 12 g/l of 67% yeast extract, 27 g/l of corn steep liquor and 9.2 g/l of NaCl was used.

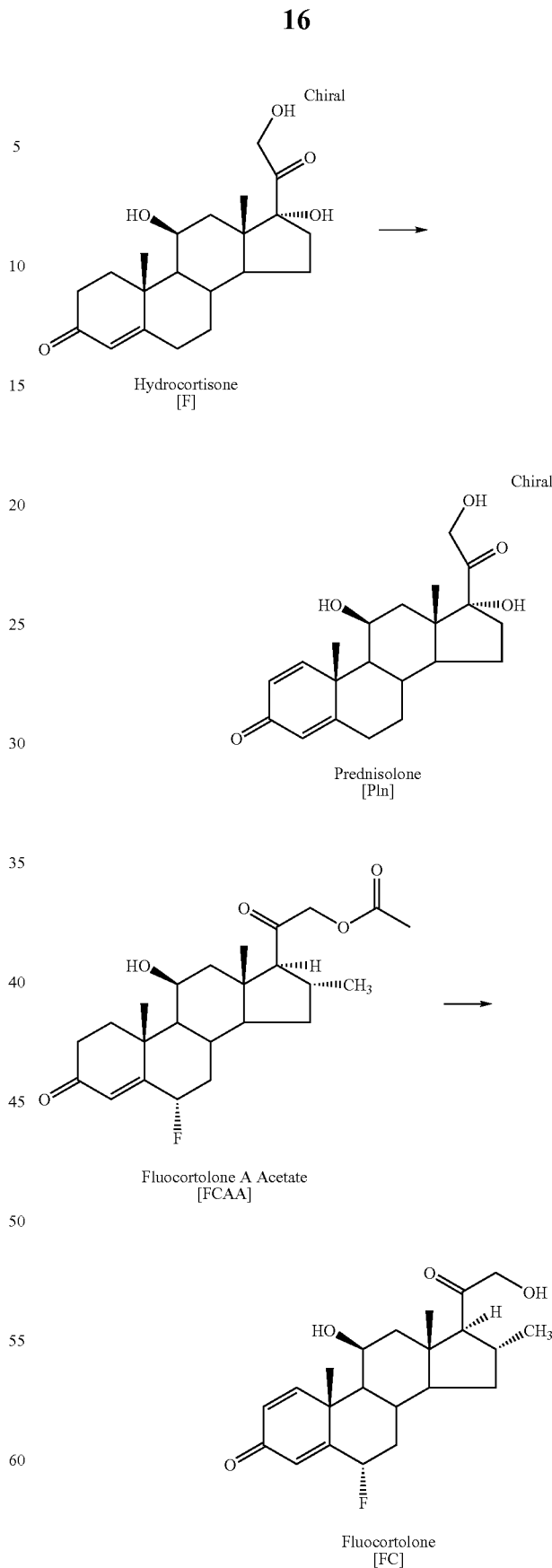

[Key:]
11β,21-Dihydroxy-2'-methyl-5'βH-pregn-4-eno[17,16-d]
  oxazol-3,20-dion=11β,21-Dihydroxy-2'-methyl-5'βH-
  pregn-4-eno[17,16-d]oxazole-3,20-dione
Deflazacortalkohol=Deflazacort alcohol

TABLE 1

| Strain | F [mg/l] | EAF/ MAF [mg/l] | Pln [mg/l] | 11β-OH-ADD [mg/l] | Substrate Loading |
|---|---|---|---|---|---|
| *Bacillus sphaericus* | | | | | |
| ATCC 13805[a] | 7720 | 39 | 1730 | <10 | 9 g/l |
| AD#67$_{TS\#196}$[a] | 1570 | 22 | 7790 | <10 | 9 g/l |
| AD#94$_{TS\#251}$[a] | 1650 | 30 | 7480 | 13 | 9 g/l |
| AD#95$_{TS\#255}$[a] | 1460 | 18 | 7500 | 13 | 9 g/l |
| AD#96$_{TS\#255}$[a] | 1530 | 19 | 7130 | 13 | 9 g/l |
| AD#116$_{TS\#251}$ | 2150 | n.d.[b] | 9330 | <10 | 12 g/l |
| *Bacillus subtilis* | | | | | |
| DSM 402[a] | 9030 | 510 | <1 | <10 | 9 g/l |
| AD#89$_{TS\#196}$ | 1820 | 500 | 8280 | 14 | 10 g/l |
| AD#90$_{TS\#196}$ | 1680 | 580 | 8120 | <10 | 10 g/l |
| *Escherichia coli* | | | | | |
| DH5α | 11110 | 1020 | <1 | n.d.[b] | 12 g/l |
| MS#46$_{MS\#46}$ | 9510 | 1080 | 1910 | n.d.[b] | 12 g/l |

[a] Double determination
[b] Not determined

SEQUENCE LISTING (1) GENERAL INFORMATION:
  (i) APPLICANT:
    (A) NAME: Schering Aktiengesellschaft
    (B) STREET: Müllerstrasse 178
    (C) CITY: Berlin
    (E) COUNTRY: Germany
    (F) POSTAL CODE (ZIP): D-13342
    (G) TELEPHONE: (030)-4681-2085
    (H) TELEFAX: (030)-4681-2058
  (ii) TITLE OF INVENTION:
    Process for the Overexpression of Dehydrogenases
  (iii) NUMBER OF SEQUENCES: 20
  (iv) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25 (EPO)
  (v) CURRENT APPLICATION DATA:
    APPLICATION NUMBER:
  (vi) PRIOR APPLICATION DATA:
    (A) APPLICATION NUMBER:
    (B) FILING DATE:
(2) INFORMATION FOR SEQ ID NO: 1:
  (i) SEQUENCE CHARACTERISTICS:
    (A) LENGTH: 1506 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM: *Arthrobacter* simplex ATCC 6946
    (C) INDIVIDUAL ISOLATE: 3-Keto steroid-$\Delta^1$-dehydrogenase gene ksdD
  (vii) IMMEDIATE SOURCE:
    (A) LIBRARY: EMBL Datenbank D37969
      (Molnar I et al., 1995, Mol Microbiol 15:895-905)
  (viii) POSITION IN GENOME:
    (B) MAP POSITION: from 1435 to 2982 coding region
    (C) UNITS:
  (xi) SEQUENCE DESCRIPTION: SEQ ID NO. 1:

```
                                                    atggac  1440 tgggcagagg agtacgacgt actggtggcg ggctccggcg ccggcggcat ggccgggacc  1500
tacaccgcgg cccgcgaggg gctcagcgtg tgcctggtcg aggccgggga caagttcggc  1560
gggacgaccg cctactccgg cggcggtggg gcctggttcc ccgcgaaccc ggtgctgctg  1620
cggccgggca ccgacgacac gatcgaggac gctctcgagt actaccgagc ggtcgtcggc  1680
gaccgcaccc ccgcggacct gcaggagacc tacgtccgcg gcggcgccgg cctggtcgcc  1740
tacctcgagg aggacgacca cttctccttc gagtcctacc cgtggccgga ctacttcggc  1800
gacgccccca aggcccgtcg cgacggccag cggcacatca tcccgacgcc gctgccggtg  1860
ccctccgcac ccgagctgcg cgaggtggtc cgcgggccgc tcgacaacga ccggctcggc  1920
acgccgcagc ccgacgacct gttcatcggc ggacgggcgc tcgtcgcccg cttcctgacc  1980
gcgctcgcga cctaccccca cgccacgctc gtgcgcgaga ccgcactggc cgagctcgtc  2040
gtcgaggacg gcgtcgtggt cggcgcgatc gtcgagaccg acggcgtccg ccgcgcgatc  2100
cgggcccgcc gcggcgtcct cctggccgcg ggcggcttcg aggccaatga cgagctccgc  2160
cagaagtacg gcgtcccgg cgtcgcgcgc gacacgatgg gcccgccgac caacgtcggc  2220
gccgcgcacc aggccgcgat cgcggtcggc ccgacaccg acctgatggg cgaggcctgc  2280
tggtcccccg ggctgaccca ccccgacgga cgatcggcgt tcgcgctctg gttcaccggc  2340
```

-continued

```
ggcatcttcg tcgacggcgc cggccggcgc ttcgtcaacg agtcggcgcc gtacgaccgg 2400
ctcggccgcg ccgtcatcga ccacctcacc gagggcggcg tcaccccgcg gtactggatg 2460
gtctacgacc acaaggaggg ctcgatcccc ccggtgcgcg ccaccaacgt ctcgatggtc 2520
gacgaggagc agtacgtcgc cgcgggcctg tggcacaccg ccgacacgct gcccgagctg 2580
gccgcgctga tcggcgtccc cgccgacgcg ctggtcgcca cggtcgcgcg cttcaacgag 2640
ctcgtcgccg acgggtacga cgcggacttc ggccgcggcg gcgaggccta cgaccggttc 2700
ttctccggcg gcgagccgcc gctggtgagc atcgacgagg ggccgttcca cgcggccgcc 2760
ttcggcatct ccgacctcgg caccaagggc gggctgcgca ccgacacgtc cgcgcgcgtg 2820
ctgaccgcgg acggcacgcc gatcgggggc ctctacgcag ccggcaatac gatggcggcg 2880
ccgagcggca ccacctaccc gggcggtggc aacccgatcg ggacaagcat gctcttcagc 2940
cacctcgccg tgcggcacat gggcaccgag gacgcgcgat ga              2982
```

(2) INFORMATION FOR SEQ ID NO: 2:
  (i) SEQUENCE CHARACTERISTICS:
    (A) LENGTH: 32 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE
    (A) ORGANISM:
    (C) INDIVIDUAL ISOLATE: Primer 2026
  (vii) IMMEDIATE SOURCE:
    (A) LIBRARY: EMBL/GenBank, AC:D37969
  (viii) POSITION IN GENOME:
    (B) MAP POSITION: from 8 to 32 coding region (Primer)
    (C) UNITS:
  (xi) SEQUENCE DESCRIPTION: SEQ ID NO: 2:
GAT CAC GAT GGA CTG GGC AGA GGA GTA CGA CG $_{1428-1459}$ (2) INFORMATION FOR SEQ ID NO: 3:
  (i) SEQUENCE CHARACTERISTICS:
    (A) LENGTH: 34 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM:
    (C) INDIVIDUAL ISOLATE: Primer 2017
  (vii) IMMEDIATE SOURCE:
    (A) LIBRARY: EMBL/GenBank, AC:D37969
  (viii) POSITION IN GENOME:
    (B) MAP POSITION: from 1 to 34 coding region (Primer)
    (C) UNITS:
  (xi) SEQUENCE DESCRIPTION: SEQ ID NO: 3:
GAC GCC GTA CTT CTG GCG GAG CTC GTC ATT GGC C $_{2175-2142}$ (2) INFORMATION FOR SEQ ID NO: 4:
  (i) SEQUENCE CHARACTERISTICS:
    (A) LENGTH: 42 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM:
    (C) INDIVIDUAL ISOLATE: Primer 2026
  (vii) IMMEDIATE SOURCE:
    (A) LIBRARY: EMBL/GenBank, AC:D37969
  (viii) POSITION IN GENOME:
    (B) MAP POSITION: from 9 to 42 coding region (Primer)
    (C) UNITS:
  (xi) SEQUENCE DESCRIPTION: SEQ ID NO. 4:

CGG GAT CCA TGG ACT GGG CAG AGG AGT ACG ACG TAC TGG TGG $_{1435-1468}$

BamHI NcoI (2) INFORMATION FOR SEQ ID NO: 5:
  (i) SEQUENCE CHARACTERISTICS:
    (A) LENGTH: 42 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM:
    (C) INDIVIDUAL ISOLATE: Primer
  (vii) IMMEDIATE SOURCE:
    (A) LIBRARY: EMBL/GenBank, AC:D37969
  (viii) POSITION IN GENOME:
    (B) MAP POSITION: from 9 to 42 coding region (Primer)
    (C) UNITS:
  (xi) SEQUENCE DESCRIPTION: SEQ ID NO: 5:

CGG AAT TCT CAT CGC GCG TCC TCG GTG CCC ATG TGC CGC ACG $_{2982-2949}$

EcoRI (2) INFORMATION FOR SEQ ID NO: 6:
(i) SEQUENCE CHARACTERISTICS:
    (A) LENGTH: 19 base pairs
    (B) TYPE: nucleic acid
    (C) STRANDEDNESS: single
    (D) TOPOLOGY: linear
(ii) MOLECULE TYPE: nucleic acid
(iii) HYPOTHETICAL: No
(iii) ANTI-SENSE: No
(vi) ORIGINAL SOURCE:
    (A) ORGANISM:
    (C) INDIVIDUAL ISOLATE: Primer 2032
(vii) IMMEDIATE SOURCE:
    (A) LIBRARY: EMBL/GenBank, AC:D37969
(viii) POSITION IN GENOME:
    (B) MAP POSITION: from 1 to 19 coding region (Primer)
    (C) UNITS:
(xi) SEQUENCE DESCRIPTION: SEQ ID NO: 6:

CGA TCG TCG AGA CCG ACG G  $_{2066-2084}$ (2) INFORMATION FOR SEQ ID NO: 7:
(i) SEQUENCE CHARACTERISTICS:
    (A) LENGTH: 27 base pairs
    (B) TYPE: nucleic acid
    (C) STRANDEDNESS: single
    (D) TOPOLOGY: linear
(ii) MOLECULE TYPE: nucleic acid
(iii) HYPOTHETICAL: No
(iii) ANTI-SENSE: No
(vi) ORIGINAL SOURCE:
    (A) ORGANISM:
    (C) INDIVIDUAL ISOLATE: Primer 2055
(vii) IMMEDIATE SOURCE:
    (A) LIBRARY: EMBL/GenBank, AC:D37969
(viii) POSITION IN GENOME:
    (B) MAP POSITION: from 1 to 27 coding region (Primer)
    (C) UNITS:
(xi) SEQUENCE DESCRIPTION: SEQ ID NO: 7:

GCA GCA CCG GGT TCG CGG GGA ACC AGG  $_{1618-1592}$ (2) INFORMATION FOR SEQ ID NO: 8:
(i) SEQUENCE CHARACTERISTICS:
    (A) LENGTH: 3630 base pairs
    (B) TYPE: nucleic acid
    (C) STRANDEDNESS: single
    (D) TOPOLOGY: linear
(ii) MOLECULE TYPE: nucleic acid
(iii) HYPOTHETICAL: No
(iii) ANTI-SENSE: No
(vi) ORIGINAL SOURCE:
    (A) ORGANISM: *Arthrobacter* simplex ATCC 6946
    (C) INDIVIDUAL ISOLATE:
        3-Keto steroid-$\Delta^1$-dehydrogenase gene ksdD
        3-Keto steroid-$\Delta^5$-isomerase gene ksdI
(vii) IMMEDIATE SOURCE:
    (A) LIBRARY: EMBL/GenBank, AC:D37969
(viii) POSITION IN GENOME:
    (B) MAP POSITION:
        from 1435 to 2982 ksdD coding region
        from 2979 to 3350 ksdI coding region
    (C) UNITS:
(xi) SEQUENCE DESCRIPTION: SEQ ID NO: 8:

```
ctgcaggagc tcggcctggt cgagcgggcc gcggacacct tcgaccggcg caccacgctg   60
gtccgctgct cgcgccgcgg cgtcgcccag gtacgccggc tcgcggccgc ccagcgcgcc  120
gacctagccg ccgcgctcgg tccggtcgac ccggccgacc gggaccgctg gacggtgctc  180
gtggagcgct acgtgcgggc tctcgaggcc cgcggctca  tctccgagct gtgactcgcc  240
ggtaagttca gagaacatta tgtgcaaacg gtccagtaaa actagccgtt cggcaagtag  300
attggtgacc catcgcattc tgtgtttccg caggtcagag gcacagtttc ggaggtgacc  360
gcagtcccgg tgaccgggag tgccgattca cggcggaaac ctcaccgaaa aatatgtgcg  420
ttcgatccac ttgatttgcc ctgtgtcagt gctcacactc gacgggaggc cgcactcccg  480
aggagcaccc gcatgaccgt caccgcactg cccacgacca cgcccgccgg ctccggcgca  540
cccgccctgg accccgacga ccgccgcacg cccctgggcg tcgtgggccg ggtgaccccgg  600
atcctcaacg ccttcagcga gtcccccgac cgcctcatgc tcgaggacgt gatggcgctg  660
accggcctgc cccggtcgac cgccttccgg atcctcggcc agctcatcga cgaggggtgg  720
gtcgagcacg acacccgcgg ctaccggctc gggccgcacg cgcccacgct caccggccgg  780
```

-continued

```
cccggcgagc accaggaggt gcgggtcgcc gcgtcgccgt acctcaacga gctgcacgcc    840
ctcaccggcg cggtcgccca cctctcggtg ctcgagggcg accgggtcca ctacctcgac    900
aagatcggcg gctccgcggc tcgcgccgtc ccctcgcggg tcggcgcccg gctgctcgcc    960
tccgacaccg tcagcggccg cgcgctgctc gcctgccgct cccccgagta cgtcgacgac   1020
gtcctcggcc cgcggctgcc cgcgccccgg ctcgccctgc tccaccgcga cctcgccgcc   1080
gcccgccagc gccgcggcgt cgtgcacgcc ccggccgacc cgaccaccgg catcgcctcg   1140
atcgccgcac ccgtcctcgg cccgcacgga gccgtcgccg cgatctcgct ggccctgccc   1200
ggcgagctgc cgcccgcccg gctcgcaccc ctgctgctca accaggccca ccggatcgcc   1260
ggcgtcctgt tcccccagcg ccgcctgcac ggacgatcct ggctgcgctg atcccgcccc   1320 cgccccggaga ctcccgcagg acgggagaac ccaccggggc acccgggggcc gctgcctagc   1380 gtcgccgcca cgacgccgga ggtcggcgtc ggtcaacccg gcgagaggat cacgatggac   1440
tgggcagagg agtacgacgt actggtggcg ggctccggcg ccggcggcat ggccgggacc   1500
tacaccgcgg cccgcgaggg gctcagcgtg tgcctggtcg aggccgggga caagttcggc   1560
gggacgaccg cctactccgg cggcggtggg gcctggttcc ccgcgaaccc ggtgctgctg   1620
cgggcgggca ccgacgacac gatcgaggac gctctcgagt actaccgagc ggtcgtcggc   1680
gaccgcaccc ccgcggacct gcaggagacc tacgtccgcg gcggcgccgg cctggtcgcc   1740
tacctcgagg aggacgacca cttctccttc gagtcctacc cgtggccgga ctacttcggc   1800
gacgccccca aggcccgtcg cgacggccag cggcacatca tcccgacgcc gctgccggtg   1860
ccctccgcac ccgagctgcg cgaggtggtc cgcgggccgc tcgacaacga ccggctcggc   1920
acgccgcagc ccgacgacct gttcatcggc ggacgggcgc tcgtcgcccg cttcctgacc   1980
gcgctcgcga cctaccccca cgccacgctc gtgcgcgaga ccgcactggc cgagctcgtc   2040
gtcgaggacg gcgtcgtggt cggcgcgatc gtcgagaccg acggcgtccg ccgcgcgatc   2100
cgggcccgcc gcggcgtcct cctggccgcg ggcggcttcg aggccaatga cgagctccgc   2160
cagaagtacg gcgtcccccgg cgtcgcgcgc gacacgatgg gcccgccgac caacgtcggc   2220
gccgcgcacc aggccgcgat cgcggtcggc gccgacaccg acctgatggg cgaggcctgg   2280
tggtcccccg gctgacccca ccccgacgga cgatcggcgt tcgcgctctg gttcaccggc   2340
ggcatcttcg tcgacggcgc cggccggcgc ttcgtcaacg agtcggcgcc gtacgaccgg   2400
ctcggccgcg ccgtcatcga ccacctcacc gagggcggcg tcaccccgcg gtactggatg   2460
gtctacgacc acaaggaggg ctcgatcccc ccggtgcgcg ccaccaacgt ctcgatggtc   2520
gacgaggagc agtacgtcgc cgcgggcctg tggcacaccg ccgacacgct gcccgagctg   2580
gccgcgctga tcggcgtccc cgccgacgcg ctggtcgcca ggtcgcgcg cttcaacgag   2640 ctcgtcgccg acgggtacga cgcggacttc ggccgcggcg gcgaggccta cgaccggttc   2700
ttctccggcg gcgagccgcc gctggtgagc atcgacgagg ggccgttcca cgcggccgcc   2760
ttcggcatct ccgacctcgg caccaagggc gggctgcgca ccgacacgtc cgcgcgcgtg   2820
```

```
ctgaccgcgg acggcacgcc gatcgggggc ctctacgcag ccggcaatac gatggcggcg 2880
ccgagcggca ccacctaccc gggcggtggc aacccgatcg ggacaagcat gctcttcagc 2940
cacctcgccg tgcggcacat gggcaccgag gacgcgcgat gagcgccgag gtgaaggccg 3000
ccgtggcgcg ctacctcgat gctgtcgccg gcggctcgcc ggccgcgatc gccgcgctct 3060
acgcccccga cgccacgctc gaggaccccg tcggcgccga cctcgtccgc ggccgcgcgg 3120
cgatcgaaga gttctacggc gccctcgccg gcgcgaaggt cagcaccgag ctgctcgccg 3180
tccgcgccgt cgcgggccac gccgcgttct cgttccgggt caccaccgac gccggcgacc 3240
agcagtacgt cgtcgagccg atcgacgtga tgacgttcga cgcggacggc cagatcacgt 3300
ccatgcgggc gttctgggcg cccggggaca tggtcgtcac gccggcctga cggtcccgct 3360
gtaacacgct gtccaccgcg cttcccggcg gttgtcgacg cgctctcggc gtgtcgcacg 3420
gcgtgtcgcg ccgtggacag cgtgttacag cggcggggc cgtcaggcgg tggccgcgtg 3480
ggtggcgacg atgtggccga agaccagacc ctggccgatg gtcgcgccgg cccccgggta 3540
gctgcgcccg aagacgttgc ccgcggtgtt gccgatcgcg tagagcccct cgatcgggct 3600
gccgtcggcg cgcagcggac ggccgagctc                                  3630
```

(2) INFORMATION FOR SEQ ID NO: 9:
  (i) SEQUENCE CHARACTERISTICS:
    (A) LENGTH: 241 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM: *Bacillus sphaericus* ATCC 13805
    (C) INDIVIDUAL ISOLATE: promoter of 3-keto steroid-$\Delta^1$-dehydrogenase ksdD (ksd⇒keto-steroid-degradation)
(vii) IMMEDIATE SOURCE:
(A) LIBRARY:
(viii) POSITION IN GENOME:
(B) MAP POSITION: from −258 to −28 promoter region
(C) UNITS:
(xi) SEQUENCE DESCRIPTION: SEQ ID NO. 9:

```
     catg acaaaattat ttgatttaat cactgcagga aagtttgatc       -241 cgactgacat aattacacat aagctaccat tagaagaagc aagtaaagcc tatcaactat -181 ttagtaaccg tgaagataac tgtattaaag tgattttaaa accttaaagg gagcgtcgac -121 gctccttttt ttgtgtgtaa tgttgggatg gaaaaattga ctgaatatta gtttaattct  -61 atacttttta ataggaagac cagattcatc gatttagctc attaagggag gaatggttga   -1
```

(2) INFORMATION FOR SEQ ID NO: 10:
(i) SEQUENCE CHARACTERISTICS:
(A) LENGTH: 1884 base pairs
(B) TYPE: nucleic acid
(C) STRANDEDNESS: single
(D) TOPOLOGY: linear
(ii) MOLECULE TYPE: nucleic acid
(iii) HYPOTHETICAL: No
(iii) ANTI-SENSE: No
(vi) ORIGINAL SOURCE:
(A) ORGANISM: *Bacillus sphaericus* ATCC 13805
(C) INDIVIDUAL ISOLATE: 3-Keto steroid-$\Delta^1$-dehydrogenase ksdD (ksd⇒keto-steroid-degradation)
(vii) IMMEDIATE SOURCE:
(A) LIBRARY:
(viii) POSITION IN GENOME:
(B) MAP POSITION: from 1 to 1689 coding region
(C) UNITS:
(xi) SEQUENCE DESCRIPTION: SEQ ID NO. 10:

```
atgaaatggg atgcaagtta tgatgtagtt gtagtaggct ctggagctgc gggattgaca   60
gcaggtttaa cagcaaagtt acaaggtttg aaatcattag taattgaaaa aacggatcgc  120
tatggtggtg cctctgctat ttcaggcggt gccttatgga ttccgaataa tcatgttatt  180
aaaggtgcag gtgttccaga tacacatgaa cttgcacgcc aatatttaga ttcaacagtt  240
ggtgatcgag tgcctgaagc tttaaaggaa gcctatatta caagaggccc agaaatgttg  300
cggttttat acaataaaac taagcatatg cgtttccaat atgcaaaagg ttactcggac  360
tactatccag aaaaaccagg gggcttgtct cagggacgtt ccattgaacc actaattttc  420
gatttaacga aatgggctc tttagcaaat actatgcgtc gagcaactct atcaactaag  480
ggctttacaa tgaatagcta tgagtttcat aaagttaata tgataacacg gacgttaaaa  540
ggtaaaacaa ctgcactgaa attaggcatg cgcctagtaa atcaaaggt gacaaaaagt  600
gagccagttg cgttaggtga agctttagta gcacgtttac gactatcgct agcggaggca  660
aatggtgagc tttggctatc aacggccttt aaagatttta tgatggataa gggtcgagtg  720
atggggatca ttgtggaacg agatggacaa gagctgcgaa ttgaggcaaa gaaaggtgtt  780
gttctttcat caggcggctt tcacacaac caagcacttc gagaacaata tttaccaagc  840
ccaacgaacg ctgcatggac ttcttcacca gagggacaaa caggtgacgt tatagaacca  900
ggtgtaaaaa ttggcgctac attagattta atggataaag tgtggggagc gccttctgtt  960
attgatccac aaggacaacc cttcttccta gtagcggaca ggggcgtacc aaatatgatt 1020
gttgtagata gcgcaggaca gcgttttgtg aatgaagcgg ctccttatca tgaatttgta 1080
gataccatgt acgagcatca aaagaccacg caacaggctg ttccttcatg atagtcatt 1140
gatgcctcta ctaaaagccg ttatatttt acaggtctgt tcccaggaca agccttccca 1200
aaaagctggt ttgatcatgg catcgtgaaa agtgcagagt ccattgaaga acttgctaga 1260
caaatggatg tgctgcctga aagtctaata gagacagtaa atcgttttaa tgactttgcc 1320
cgaaatggtc atgatgatga ttttttatcgt ggtgatagtg cctatgataa ttactatggg 1380
gacccaacat tgccaaatcc aaatttagca gagatcaaaa aagctccttt ctatgcatta 1440
cgtatatatc caggcgatat tggcacaaag ggaggcttgg tagtggatga acatgctcgg 1500
gttattaagg cagatggcga accaatcgaa ggattatatg cttcaggtaa ttgttcagcg 1560
tcgatcatgg gagaaacgta tcctggtccg ggtgctacga ttgggcctgg tatgacatta 1620
agctttgtgg cgactacaca tatggctaac accgtaaaaa aagaagaagt accacttgta 1680
aaaatataa                                                         1689
     a gttgactaag cccttcctat gactgtgata aggaagggct ttcatgtgga      1740
tgaaatgttc taatattttt ttgctaagaa tatagtggct acaacatgta tggcgatgat 1800
aatggaaaaa aggagcgata tagtaaattg cttacgtata aacttatcac gactattgaa 1860
gcattagagc cctatcgaag tact                                        1884
```

(2) INFORMATION FOR SEQ ID NO: 11:
  (i) SEQUENCE CHARACTERISTICS:
    (A) LENGTH: 562 amino acids
    (B) TYPE: peptide
    (C) STRANDEDNESS: single
    (D) TOPOLOGY: linear
  (ii) MOLECULE TYPE: peptide
  (vi) ORIGINAL SOURCE:
    (A) ORGANISM: *Bacillus sphaericus* ATCC 13805
    (C) INDIVIDUAL ISOLATE: 3-Keto steroid-$\Delta^1$-dehydrogenase KsdD
      (Ksd⇒<u>K</u>eto-<u>s</u>teroid-<u>d</u>egradation)
  (xi) SEQUENCE DESCRIPTION: SEQ ID NO. 11:

```
MKWDASYDVV VVGSGAAGLT AGLTAKLQGL KSLVIEKTDR   40
YGGASAISGG ALWIPNNHVI KGAGVPDTHE LARQYLDSTV   80
GDRVPEALKE AYITRGPEML RFLYNKTKHM RFQYAKGYSD  120
YYPEKPGGLS QGRSIEPLIF DLTKMGSLAN TMRRATLSTK  160
GFTMNSYEFH KVNMITRTLK GKTTALKLGM RLVKSKVTKS  200
EPVALGEALV ARLRLSLAEA NGELWLSTAF KDFMMDKGRV  240
MGIIVERDGQ ELRIEAKKGV VLSSGGFSHN QALREQYLPS  280
PTNAAWTSSP EGQTGDVIEP GVKIGATLDL MDKVWGAPSV  320
IDPQGQPFFL VADRGVPNMI VVDSAGQRFE NEAAPYHEFV  360
DTMYEHQKTT QQAVPSWIVI DASTKSRYIF TGLFPGQAFP  400
KSWFDHGIVK SAESIEELAR QMDVLLESLI ETVNRFNDFA  440
RNGHDDDFYR GDSVYDNYYG DPTLPNPNLA EIKKAPFYAL  480
RIYPGDIGTK GGLVDEHARV IKADGEPIEG LYASGNCSAS  520
IMGETYPGPG ATIGPGMTLS FVAATTHMAN TVKKEEVPLV  560
KI*                                         562
```

(2) INFORMATION FOR SEQ ID NO: 12:
  (i) SEQUENCE CHARACTERISTICS:
    (A) LENGTH: 1539 base pairs
    (B) TYPE: nucleic acid
    (C) STRANDEDNESS: single
    (D) TOPOLOGY: linear
  (ii) MOLECULE TYPE: nucleic acid
  (iii) HYPOTHETICAL: No
  (iii) ANTI-SENSE: No
  (vi) ORIGINAL SOURCE:
    (A) ORGANISM: *Brevibacterium maris* ATCC 2111
    (C) INDIVIDUAL ISOLATE: 3-Keto steroid-$\Delta^1$-dehydrogenase gene ksdD
      (ksd⇒<u>k</u>eto-<u>s</u>teroid-<u>d</u>egradation)
  (vii) IMMEDIATE SOURCE:
    (A) LIBRARY:
  (viii) POSITION IN GENOME:
    (B) MAP POSITION: from 1 to 1539 coding region
    (C) UNITS:
  (xi) SEQUENCE DESCRIPTION: SEQ ID NO. 12:

```
atggtcaact ggaacgaaga atgtgacgtg ttggtggccg ggtcgggcgc cggtggcgtc    60
accggcgcgt acaccgcggc tcgcgagggc ctcgacgtga tcctggtcga ggcgacggac   120
aagttcggcg gcaccaccgc gtactccggt ggcggcgggt tctggttccc ggccaacccg   180
gtgctcaagc gcgccggcac cgacgacacg atcgaggacg cgctcgagta ctaccacgcc   240
gtcgtcggcg accggacccc gcgcgagctg caggacacct acgtcaaggg cggcgctccg   300
ctggtcgagt acctcgagca ggacgagaac ctcaagttcg agatgctgcc gtggcccgac   360
tactacggca agatgccgaa ggcccgcaac gacggccagc gccacacgat gccgacgccg   420
ctgccgatct ccgaggtcgg tgacctgcac aagctcgtcc gcggaccgct cgacttcgac   480
cggctcggcg ccgacctgcc cgagatgctg atcggcggcc gcgcgctcgt cggtcgcttc   540
ctcaaggcga tcggcaacta cccgaacgcg aagctgaacc tcaacacccc gctcgtcgag   600
ctggtggtcg aggacggcgc cgtcgtcggc gcgctcgtcg agcgtgacgg cgagcaggtc   660
gcgatccgcg cccgcaaggg cgtcatcctg gcggccggcg gcttcgaggg caacgacgag   720
ctgcgccaga agtacgccgt ccccggtgtc gcgcgcgaca cgatgggtcc gtgggcaac   780
gtcggccagg cgcaccaggc cggcatcgcc gtcggtgccg acaccgacct gatggaccag   840
gcgtggtggt cgcgcggcct gacccacccg gacgacgtt ccgcgttcgc gctgtgcttc   900
accggcggca tcttcgtcaa cgacgacggc aagcgcttcg tcaacgagta cgcgccgtac   960
gaccgcctcg gccgcgacat catcgcgggc atggaggacg gtcggtcac gctgccgtac  1020
tggatgatct acgacgacaa gcagggccag cggccgccga tcgcggccac caacgtctcg  1080
atggtcgaga ccgagaagta cgtcgacgcc ggcctgtggc acaccgccga cacgctcgag  1140
gagctggccg gaaagatcgg tgtcccggcg gagaacctgc tggcaacggt ggagcggttc  1200
```

```
aacgcgatgg ccgccaacga cgtcgacgag gacttcggtc gcggcgacga ggcgtacgac  1260
cgggcgttca ccggcggcgg cccggcgctg atcccgatcg agcagggtcc gttccacgct  1320
gccgcgttcg gcatctccga cctcggcacc aagggcggtc tgcgtaccga caccgcggcg  1380
cgggtgctcg acacctcggg caacccgatc cccggtctgt acgcggccgg caacaccatg  1440
gcggccccga gcggcaccac ctaccccggt ggcggtaacc cgatcggcac ctccatgctg  1500
ttcagccaca tcgccgcgat gaacatcgcc ggcaagtag                          1539
```

(2) INFORMATION FOR SEQ ID NO: 13:
(i) SEQUENCE CHARACTERISTICS:
(A) LENGTH: 512 amino acids
(B) TYPE: peptide
(C) STRANDEDNESS: single
(D) TOPOLOGY: linear
(ii) MOLECULE TYPE: peptide
(vi) ORIGINAL SOURCE:
(A) ORGANISM: *Brevibacterium maris* ATCC 2111
(C) INDIVIDUAL ISOLATE: 3-Keto steroid-$\Delta^1$-dehydrogenase KsdD
(Ksd⇒Keto-steroid-degradation)
(xi) SEQUENCE DESCRIPTION: SEQ ID NO. 13:

```
MVNWNEECDV LVAGSGAGGV TGAYTAAREG LDVILVEATD   40
KFGGTTAYSG GGGFWFPANP VLKRAGTDDT IEDALEYYHA   80
VVGDRTPREL QDTYVKGGAP LVEYLEQDEN LKFEMLPWPD  120
YYGKMPKARN DGQRHTMPTP LPISEVGDLH KLVRGPLDFD  160
RLGADLPEML IGGRALVGRF LKAIGNYPNA KLNLNTPLVE  200
LVVEDGAVVG ALVERDGEQV AIRARKGVIL AAGGFEGNDE  240
LRQKYGVPGV ARDTMGPWGN VGQAHQAGIA VGADTDLMDQ  280
AWWSPGLTHP DGRSAFALCF TGGIFVNDDG KRFVNEYAPY  320
DRLGRDIIAG MEDGSVTLPY WMIYDDKQGQ RPPIAATNVS  360
MVETEKYVDA GLWHTADTLE ELAGKIGVPA ENLLATVERF  400
NAMAANDVDE DFGRGDEAYD RAFTGGGPAL IPIEQGPFHA  440
AAFGISDLGT KGGLRTDTAA RVLDTSGNPI PGLYAAGNTM  480
AAPSGTTYPG GGNPIGTSML FSHIAAMNIA GK          512
```

(2) INFORMATION FOR SEQ ID NO: 14:
(i) SEQUENCE CHARACTERISTICS:
(A) LENGTH: 515 amino acids
(B) TYPE: peptide
(C) STRANDEDNESS: single
(D) TOPOLOGY: linear
(ii) MOLECULE TYPE: peptide
(vi) ORIGINAL SOURCE:
(A) ORGANISM: *Arthrobacter* simplex
(C) INDIVIDUAL ISOLATE: 3-Keto steroid-$\Delta^1$-dehydrogenase KsdD
(Ksd⇒Keto-steroid-degradation)
(vii) IMMEDIATE SOURCE:
(A) LIBRARY: EMBL/GenBank, AC:D37969
(xi) SEQUENCE DESCRIPTION: SEQ ID NO. 14:

```
MDWAEEYDVL VAGSGAGGMA GTYTAAREGL SVCLVEAGDK   40
FGGTTAYSGG GGAWFPANPV LLRAGTDDTI EDALEYYRAV   80
VGDRTPADLQ ETYVRGGAGL VAYLEEDDHF SFESYPWPDY  120
FGDAPKARRD GQRHIIPTPL PVPSAPELRE VVRGPLDNDR  160
LGTPQPDDLF IGGRALVARF LTALATYPHA TLVRETALAE  200
LVVEDGVVVG AIVETDGVRR AIRARRGVLL AAGGFEANDE  240
LRQKYGVPGV ARDTMGPPTN VGAAHQAAIA VGADTDLMGE  280
AWWSPGLTHP DGRSAFALWF TGGIFVDGAG RRFVNESAPY  320
DRLGRAVIDH LTEGGVTPRY WMVYDHKEGS IPPVRATNVS  360
MVDEEQYVAA GLWHTADTLP ELAALIGVPA DALVATVARF  400
NELVADGYDA DFGRGGEAYD RFFSGGEPPL VSIDEGPFHA  440
AAFGISDLGT KGGLRTDTSA RVLTADGTPI GGLYAAGNTM  480
AAPSGTTYPG GGNPIGTSML FSHLAVRHMG TEDAR*      515
```

(2) INFORMATION FOR SEQ ID NO: 15:
(i) SEQUENCE CHARACTERISTICS:
(A) LENGTH: 29 base pairs
(B) TYPE: nucleic acid
(C) STRANDEDNESS: single
(D) TOPOLOGY: linear
(ii) MOLECULE TYPE: nucleic acid
(iii) HYPOTHETICAL: No
(iii) ANTI-SENSE: No
(vi) ORIGINAL SOURCE:
(C) INDIVIDUAL ISOLATE: Primer 2048
(vii) IMMEDIATE SOURCE:
(A) LIBRARY:
(xi) SEQUENCE DESCRIPTION: SEQ ID NO. 15:

```
GAA TRY GAT NTW NTW GTW GYW GGW WSW GG
``` with N≡GATC, R≡GA, S≡GC, W≡AT, Y≡TC (2) INFORMATION FOR SEQ ID NO: 16:
(i) SEQUENCE CHARACTERISTICS:
(A) LENGTH: 18 base pairs
(B) TYPE: nucleic acid
(C) STRANDEDNESS: single
(D) TOPOLOGY: linear
(ii) MOLECULE TYPE: nucleic acid
(iii) HYPOTHETICAL: No
(iii) ANTI-SENSE: No
(vi) ORIGINAL SOURCE:
(C) INDIVIDUAL ISOLATE: Primer 2054

(vii) IMMEDIATE SOURCE:
  (A) LIBRARY:
(xi) SEQUENCE DESCRIPTION: SEQ ID NO. 16:
  NAR NCC NCC YTT NGT NCC
  with N=GATC, R=GA, S=GC, W=AT, Y=TC
(2) INFORMATION FOR SEQ ID NO: 17:
(i) SEQUENCE CHARACTERISTICS:
  (A) LENGTH: 66 base pairs
  (B) TYPE: nucleic acid
  (C) STRANDEDNESS: single
  (D) TOPOLOGY: linear
(ii) MOLECULE TYPE: nucleic acid
(iii) HYPOTHETICAL: No
(iii) ANTI-SENSE: No
(vi) ORIGINAL SOURCE:
  (C) INDIVIDUAL ISOLATE: Primer $2089_{mut}$
(vii) IMMEDIATE SOURCE:
  (A) LIBRARY: Seq. ID No. 9
(viii) POSITION IN GENOME:
  (B) MAP POSITION: from –29 to –91 promoter region
  (C) UNITS:
(xi) SEQUENCE DESCRIPTION: SEQ ID NO. 17:

CCA TCG ATG AAT CTG GTC TTC CTA TTA AAA ATT ATA
GAA TTA AAC TAA TAT TCT GTC AAT TTT $TCC_{-29\ to\ -91}$ with N=GATC, R=GA, S=GC, W=AT, Y=TC
(2) INFORMATION FOR SEQ ID NO: 18:
(i) SEQUENCE CHARACTERISTICS:
  (A) LENGTH: 27 base pairs
  (B) TYPE: nucleic acid
  (C) STRANDEDNESS: single
  (D) TOPOLOGY: linear
(ii) MOLECULE TYPE: nucleic acid
(iii) HYPOTHETICAL: No
(iii) ANTI-SENSE: No
(vi) ORIGINAL SOURCE:
  (C) INDIVIDUAL ISOLATE: Primer 2090
(vii) IMMEDIATE SOURCE:
  (A) LIBRARY: Seq. ID No. 9
(viii) POSITION IN GENOME:
  (B) MAP POSITION: from –258 to –284
  (C) UNITS:
(xi) SEQUENCE DESCRIPTION: SEQ ID NO. 18:

CAT GAC AAA ATT ATT TGA TTT AAT $CAC_{-258\ to\ -284}$ with N=GATC, R=GA, S=GC, W=AT, Y=TC
(2) INFORMATION FOR SEQ ID NO: 19:
(i) SEQUENCE CHARACTERISTICS:
  (A) LENGTH: 22 base pairs
  (B) TYPE: nucleic acid
  (C) STRANDEDNESS: single
  (D) TOPOLOGY: linear
(ii) MOLECULE TYPE: nucleic acid
(iii) HYPOTHETICAL: No
(iii) ANTI-SENSE: No
(vi) ORIGINAL SOURCE:
  (C) INDIVIDUAL ISOLATE: Oligonucleotide $2091_{parS}$
(vii) IMMEDIATE SOURCE:
  (A) LIBRARY: Lin, D. C. and Grossman, A. D. (1998, Cell 92: 675-685)
(xi) SEQUENCE DESCRIPTION: SEQ ID NO. 19:

GAT CCT GTT CCA CGT GAA ACA G (2) INFORMATION FOR SEQ ID NO: 20:
(i) SEQUENCE CHARACTERISTICS:
  (A) LENGTH: 22 base pairs
  (B) TYPE: nucleic acid
  (C) STRANDEDNESS: single
  (D) TOPOLOGY: linear
(ii) MOLECULE TYPE: nucleic acid
(iii) HYPOTHETICAL: No
(iii) ANTI-SENSE: No
(vi) ORIGINAL SOURCE:
  (C) INDIVIDUAL ISOLATE: Oligonucleotide $2092_{parS}$
(vii) IMMEDIATE SOURCE:
  (A) LIBRARY: Lin, D. C. and Grossman, A. D. (1998, Cell 92: 675-685)
(xi) SEQUENCE DESCRIPTION: SEQ ID NO. 20:

GAT CCT GTT TCA CGT GGA ACA G

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding Germany Application No. 102 04 798.1, filed Feb. 1, 2002, and U.S. Provisional Application Ser. No. 60/382,569, filed May 24, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

SEQUENCE LISTING

<160> NUMBER OF SEQ ID NOS: 29

<210> SEQ ID NO 1
<211> LENGTH: 1548

```
<212> TYPE: DNA
<213> ORGANISM: Arthrobacter simplex

<400> SEQUENCE: 1
atggactggg cagaggagta cgacgtactg gtggcgggct ccggcgccgg cggcatggcc    60
gggacctaca ccgcggcccg cgaggggctc agcgtgtgcc tggtcgaggc cggggacaag   120
ttcggcggga cgaccgccta ctccggcggc ggtggggcct ggttccccgc gaacccggtg   180
ctgctgcggg cgggcaccga cgacacgatc gaggacgctc tcgagtacta ccgagcggtc   240
gtcgccgacc gcaccccgc ggacctgcag gagacctacg tccgcggcgg cgccggcctg   300
gtcgcctacc tcgaggagga cgaccacttc tccttcgagt cctacccgtg gccggactac   360
ttcggcgacg cccccaaggc ccgtcgcgac ggccagcggc acatcatccc gacgccgctg   420
ccggtgccct ccgcacccga gctgcgcgag gtggtccgcg gccgctcga caacgaccgg   480
ctcggcacgc cgcagcccga cgacctgttc atcggcggac gggcgctcgt cgcccgcttc   540
ctgaccgcgc tcgcgaccta ccccacgcc acgctcgtgc gcgagaccgc actggccgag   600
ctcgtcgtcg aggacggcgt cgtggtcggc gcgatcgtcg agaccgacgg cgtccgccgc   660
gcgatccggg cccgccgcgg cgtcctcctg gccgcgggcg gcttcgaggc caatgacgag   720
ctccgccaga agtacggcgt ccccggcgtc gcgcgcgaca cgatgggccc gccgaccaac   780
gtcggcgccg cgcaccaggc cgcgatcgcg gtcgcgccg acaccgacct gatgggcgag   840
gcctggtggt cccccgggct gacccacccc gacggacgat cggcgttcgc gctctggttc   900
accggcggca tcttcgtcga cggcgccggc cggcgcttcg tcaacgagtc ggcgccgtac   960
gaccggctcg ccgcgccgt catcgaccac ctcaccgagg cggcgtcac cccgcggtac  1020
tggatggtct acgaccacaa ggagggctcg atcccccggg tgcgcgccac caacgtctcg  1080
atggtcgacg aggagcagta cgtcgccgcg ggcctgtggc acaccgccga cacgctgccc  1140
gagctggccc gctgatcgg cgtccccgcc gacgcgctgg tcgccacggt cgcgcgcttc  1200
aacgagctcg tcgccgacgg gtacgacgcg gacttcggcc gcggcggcga ggcctacgac  1260
cggttcttct ccggcggcga gccgccgctg gtgagcatcg acgagggcc gttccacgcg  1320
gccgccttcg gcatctccga cctcggcacc aagggcgggc tgcgcaccga cacgtccgcg  1380
cgcgtgctga ccgcggacgg cacgccgatc ggggcctct acgcagccgg caatacgatg  1440
gcggcgccga gcggcaccac ctacccgggc ggtggcaacc cgatcgggac aagcatgctc  1500
ttcagccacc tcgccgtgcg gcacatgggc accgaggacg cgcgatga                1548

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 2
gatcacgatg gactgggcag aggagtacga cg                                   32

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 3
```

```
gacgccgtac ttctggcgga gctcgtcatt ggcc                                   34

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 4
cgggatccat ggactgggca gaggagtacg acgtactggt gg                          42

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 5
cggaattctc atcgcgcgtc ctcggtgccc atgtgccgca cg                          42

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
cgatcgtcga gaccgacgg                                                    19

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
gcagcaccgg gttcgcgggg aaccagg                                           27

<210> SEQ ID NO 8
<211> LENGTH: 3630
<212> TYPE: DNA
<213> ORGANISM: Arthrobacter simplex

<400> SEQUENCE: 8
ctgcaggagc tcggcctggt cgagcgggcc gcggacacct tcgaccggcg caccacgctg       60
gtccgctgct cgcgccgcgg cgtcgcccag gtacgccggc tcgcggccgc ccagcgcgcc      120
gacctagccg ccgcgctcgg tccggtcgac ccggccgacc gggaccgctg gacggtgctc      180
gtggagcgct acgtgcgggc tctcgaggcc cgcgggctca tctccgagct gtgactcgcc      240
ggtaagttca gagaacatta tgtgcaaacg tccagtaaa actagccgtt cggcaagtag       300
attggtgacc catcgcattc tgtgtttccg caggtcagag gcacagtttc ggaggtgacc      360
gcagtcccgg tgaccgggag tgccgattca cggcggaaac ctcaccgaaa aatatgtgcg      420
ttcgatccac ttgatttgcc ctgtgtcagt gctcacactc gacgggaggc cgcactcccg      480
aggagcaccc gcatgaccgt caccgcactg cccacgacca cgcccgccgg ctccggcgca      540
cccgccctgg accccgacga ccgcgcacg ccctgggcg tcgtgggccg ggtgacccgg        600
atcctcaacg ccttcagcga gtccccccgac cgcctcatgc tcgaggacgt gatggcgctg    660
```

```
accggcctgc cccggtcgac cgccttccgg atcctcggcc agctcatcga cgagggtgg    720
gtcgagcacg acacccgcgg ctaccggctc gggccgcacg cgcccacgct caccggccgg   780
cccggcgagc accaggaggt gcgggtcgcc gcgtcgccgt acctcaacga gctgcacgcc   840
ctcaccggcg cggtcgccca cctctcggtg ctcgagggcg accgggtcca ctacctcgac   900
aagatcggcg gctccgcggc tcgcgccgtc ccctcgcggg tcggcgcccg gctgctcgcc   960
tccgacaccg tcagcggccg cgcgctgctc gcctgccgct cccccgagta cgtcgacgac  1020
gtcctcggcc cgcggctgcc cgcgcccngg ctcgccctgc tccaccgcga cctcgccgcc  1080
gcccgccagc gccgcggcgt cgtgcacgcc ccggccgacc cgaccaccgg catcgcctcg  1140
atcgccgcac ccgtcctcgg cccgcacgga gccgtcgccg cgatctcgct ggccctgccc  1200
ggcgagctgc cgcccgcccg gctcgcaccc ctgctgctca accaggccca ccggatcgcc  1260
ggcgtcctgt tccccagcg ccgcctgcac ggacgatcct ggctgcgctg atcccgcccc  1320
cgcccggaga ctcccgcagg acgggagaac ccaccggggc accggggcc gctgcctagc  1380
gtcgccgcca cgacgccgga ggtcggcgtc ggtcaacccg gcgagaggat cacgatggac  1440
tgggcagagg agtacgacgt actggtggcg ggctccggcg ccggcggcat ggccgggacc  1500
tacaccgcgg cccgcgaggg gctcagcgtg tgcctggtcg aggccgggga caagttcggc  1560
gggacgaccg cctactccgg cggcggtggg gcctggttcc ccgcgaaccc ggtgctgctg  1620
cgggcgggca ccgacgacac gatcgaggac gctctcgagt actaccgagc ggtcgtcggc  1680
gaccgcaccc ccgcggacct gcaggagacc tacgtccgcg gcggcgccgg cctggtcgcc  1740
tacctcgagg aggacgacca cttctccttc gagtcctacc cgtggccgga ctacttcggc  1800
gacgccccca aggcccgtcg cgacggccag cggcacatca tcccgacgcc gctgccggtg  1860
ccctccgcac ccgagctgcg cgaggtggtc cgcgggccgc tcgacaacga ccggctcggc  1920
acgccgcagc ccgacgacct gttcatcggc ggacgggcgc tcgtcgcccg cttcctgacc  1980
gcgctcgcga cctaccccca cgccacgctc gtgcgcgaga ccgcactggc cgagctcgtc  2040
gtcgaggacg cgtcgtggt cggcgcgatc gtcgagaccg acggcgtccg ccgcgcgatc  2100
cgggcccgcc gcggcgtcct cctggccgcg ggcggcttcg aggccaatga cgagctccgc  2160
cagaagtacg gcgtcccccg gcgtcgcgcg cgacacgatgg gcccgccgac caacgtcggc  2220
gccgcgcacc aggccgcgat cgcggtcggc gccgacaccg acctgatggg cgaggcctgg  2280
tggtcccccg ggctgaccca ccccgacgga cgatcggcgt tcgcgctctg gttcaccggc  2340
ggcatcttcg tcgacggcgc cggccggcgc ttcgtcaacg agtcggcgcc gtacgaccgg  2400
ctcggccgcg ccgtcatcga ccacctcacc gagggcggcg tcaccccgcg gtactggatg  2460
gtctacgacc acaaggaggg ctcgatcccc ccggtgcgcg ccaccaacgt ctcgatggtc  2520
gacgaggagc agtacgtcgc cgcgggcctg tggcacaccg ccgacacgct gcccgagctg  2580
gccgcgctga tcggcgtccc cgccgacgcg ctggtcgcca cggtcgcgcg cttcaacgag  2640
ctcgtcgccg acgggtacga cgcggacttc ggccgcggcg gcgaggccta cgaccggttc  2700
ttctccggcg gcgagccgcc gctggtgagc atcgacgagg ggccgttcca cgcggccgcc  2760
ttcggcatct ccgacctcgg caccaagggc gggctgcgca ccgacacgtc cgcgcgcgtg  2820
ctgaccgcg acggcacgcc gatcgggggc ctctacgcag ccggcaatac gatggcggcg  2880
ccgagcggca ccacctaccc gggcggtggc aacccgatcg gacaagcat gctcttcagc  2940
cacctcgccg tgcggcacat gggcaccgag gacgcgcgat gagcgccgag gtgaaggccg  3000
```

-continued

| | |
|---|---|
| ccgtggcgcg ctacctcgat gctgtcgccg gcggctcgcc ggccgcgatc gccgcgctct | 3060 |
| acgcccccga cgccacgctc gaggaccccg tcggcgccga cctcgtccgc ggccgcgcgg | 3120 |
| cgatcgaaga gttctacggc gccctcgccg gcgcgaaggt cagcaccgag ctgctcgccg | 3180 |
| tccgcgccgt cgcgggccac gccgcgttct cgttccgggt caccaccgac gccggcgacc | 3240 |
| agcagtacgt cgtcgagccg atcgacgtga tgacgttcga cgcggacggc cagatcacgt | 3300 |
| ccatgcgggc gttctgggcg cccggggaca tggtcgtcac gccggcctga cggtcccgct | 3360 |
| gtaacacgct gtccaccgcg cttcccggcg gttgtcgacg cgctctcggc gtgtcgcacg | 3420 |
| gcgtgtcgcg ccgtggacag cgtgttacag cggcggggc cgtcaggcgg tggccgcgtg | 3480 |
| ggtggcgacg atgtggccga agaccagacc ctggccgatg tcgcgccgg ccccgggta | 3540 |
| gctgcgcccg aagacgttgc ccgcggtgtt gccgatcgcg tagagcccct cgatcgggct | 3600 |
| gccgtcggcg cgcagcggac ggccgagctc | 3630 |

<210> SEQ ID NO 9
<211> LENGTH: 284
<212> TYPE: DNA
<213> ORGANISM: Bacillus sphaericus

<400> SEQUENCE: 9

| | |
|---|---|
| catgacaaaa ttatttgatt taatcactgc aggaaagttt gatccgactg acataattac | 60 |
| acataagcta ccattagaag aagcaagtaa agcctatcaa ctatttagta accgtgaaga | 120 |
| taactgtatt aaagtgattt taaaacctta aagggagcgt cgacgctcct ttttttgtgt | 180 |
| gtaatgttgg gatggaaaaa ttgactgaat attagtttaa ttctatactt tttaatagga | 240 |
| agaccagatt catcgattta gctcattaag ggaggaatgg ttga | 284 |

<210> SEQ ID NO 10
<211> LENGTH: 1884
<212> TYPE: DNA
<213> ORGANISM: Bacillus sphaericus

<400> SEQUENCE: 10

| | |
|---|---|
| atgaaatggg atgcaagtta tgatgtagtt gtagtaggct ctggagctgc gggattgaca | 60 |
| gcaggtttaa cagcaaagtt acaaggtttg aaatcattag taattgaaaa aacggatcgc | 120 |
| tatggtggtg cctctgctat ttcaggcggt gccttatgga ttccgaataa tcatgttatt | 180 |
| aaaggtgcag gtgttccaga tacacatgaa cttgcacgcc aatatttaga ttcaacagtt | 240 |
| ggtgatcgag tgcctgaagc tttaaaggaa gcctatatta caagaggccc agaaatgttg | 300 |
| cggtttttat acaataaaac taagcatatg cgtttccaat atgcaaaagg ttactcggac | 360 |
| tactatccag aaaaaccagg gggcttgtct cagggacgtt ccattgaacc actaattttc | 420 |
| gatttaacga aaatgggctc tttagcaaat actatgcgtc gagcaactct atcaactaag | 480 |
| ggctttacaa tgaatagcta tgagtttcat aaagttaata tgataacacg gacgttaaaa | 540 |
| ggtaaaacaa ctgcactgaa attaggcatg cgcctagtaa aatcaaaggt gacaaaaagt | 600 |
| gagccagttg cgttaggtga agctttagta gcacgtttac gactatcgct agcggaggca | 660 |
| aatggtgagc tttggctatc aacggccttt aaagatttta tgatggataa gggtcgagtg | 720 |
| atggggatca ttgtggaacg agatggacaa gagctgcgaa ttgaggcaaa gaaaggtgtt | 780 |
| gttctttcat caggcggctt ttcacacaac caagcacttc gagaacaata tttaccaagc | 840 |
| ccaacgaacg ctgcatggac ttcttccacca gaggacaaa caggtgacgt tatagaacca | 900 |
| ggtgtaaaaa ttggcgctac attagattta atggataaag tgtggggagc gccttctgtt | 960 |

```
attgatccac aaggacaacc cttcttccta gtagcggaca ggggcgtacc aaatatgatt    1020
gttgtagata gcgcaggaca gcgttttgtg aatgaagcgg ctccttatca tgaatttgta    1080
gataccatgt acgagcatca aaagaccacg caacaggctg ttccttcatg atagtcatt     1140 gatgcctcta ctaaaagccg ttatattttt acaggtctgt tcccaggaca agccttccca    1200
aaaagctggt tgatcatgg catcgtgaaa agtgcagagt ccattgaaga acttgctaga     1260
caaatggatg tgctgcctga agtctaata gagacagtaa atcgttttaa tgactttgcc    1320
cgaaatggtc atgatgatga ttttatcgt ggtgatagtg cctatgataa ttactatggg     1380
gacccaacat tgccaaatcc aaatttagca gagatcaaaa aagctccttt ctatgcatta    1440
cgtatatatc caggcgatat tggcacaaag ggaggcttgg tagtggatga acatgctcgg    1500
gttattaagg cagatggcga accaatcgaa ggattatatg cttcaggtaa ttgttcagcg    1560
tcgatcatgg gagaaacgta tcctggtccg ggtgctacga ttgggcctgg tatgacatta    1620
agctttgtgg cgactacaca tatggctaac accgtaaaaa aagaagaagt accacttgta    1680
aaaatataaa gttgactaag cccttcctat gactgtgata aggaagggct tcatgtgga    1740 tgaaatgttc taatattttt ttgctaagaa tatagtggct acaacatgta tggcgatgat    1800
aatggaaaaa aggagcgata tagtaaattg cttacgtata aacttatcac gactattgaa    1860
gcattagagc cctatcgaag tact                                          1884
```

<210> SEQ ID NO 11
<211> LENGTH: 562
<212> TYPE: PRT
<213> ORGANISM: Bacillus sphaericus
<400> SEQUENCE: 11

```
Met Lys Trp Asp Ala Ser Tyr Asp Val Val Val Gly Ser Gly Ala
1               5                   10                  15

Ala Gly Leu Thr Ala Gly Leu Thr Ala Lys Leu Gln Gly Leu Lys Ser
                20                  25                  30

Leu Val Ile Glu Lys Thr Asp Arg Tyr Gly Gly Ala Ser Ala Ile Ser
            35                  40                  45

Gly Gly Ala Leu Trp Ile Pro Asn Asn His Val Ile Lys Gly Ala Gly
        50                  55                  60

Val Pro Asp Thr His Glu Leu Ala Arg Gln Tyr Leu Asp Ser Thr Val
65                  70                  75                  80

Gly Asp Arg Val Pro Glu Ala Leu Lys Glu Ala Tyr Ile Thr Arg Gly
                85                  90                  95

Pro Glu Met Leu Arg Phe Leu Tyr Asn Lys Thr Lys His Met Arg Phe
            100                 105                 110

Gln Tyr Ala Lys Gly Tyr Ser Asp Tyr Tyr Pro Glu Lys Pro Gly Gly
        115                 120                 125

Leu Ser Gln Gly Arg Ser Ile Glu Pro Leu Ile Phe Asp Leu Thr Lys
    130                 135                 140

Met Gly Ser Leu Ala Asn Thr Met Arg Arg Ala Thr Leu Ser Thr Lys
145                 150                 155                 160

Gly Phe Thr Met Asn Ser Tyr Glu Phe His Lys Val Asn Met Ile Thr
                165                 170                 175

Arg Thr Leu Lys Gly Lys Thr Thr Ala Leu Lys Leu Gly Met Arg Leu
            180                 185                 190

Val Lys Ser Lys Val Thr Lys Ser Glu Pro Val Ala Leu Gly Glu Ala
        195                 200                 205
```

```
Leu Val Ala Arg Leu Arg Leu Ser Leu Ala Glu Ala Asn Gly Glu Leu
    210                 215                 220

Trp Leu Ser Thr Ala Phe Lys Asp Phe Met Met Asp Lys Gly Arg Val
225                 230                 235                 240

Met Gly Ile Ile Val Glu Arg Asp Gly Gln Glu Leu Arg Ile Glu Ala
                245                 250                 255

Lys Lys Gly Val Val Leu Ser Ser Gly Phe Ser His Asn Gln Ala
            260                 265                 270

Leu Arg Glu Gln Tyr Leu Pro Ser Pro Thr Asn Ala Ala Trp Thr Ser
        275                 280                 285

Ser Pro Glu Gly Gln Thr Gly Asp Val Ile Glu Pro Gly Val Lys Ile
    290                 295                 300

Gly Ala Thr Leu Asp Leu Met Asp Lys Val Trp Gly Ala Pro Ser Val
305                 310                 315                 320

Ile Asp Pro Gln Gly Gln Pro Phe Phe Leu Val Ala Asp Arg Gly Val
                325                 330                 335

Pro Asn Met Ile Val Val Asp Ser Ala Gly Gln Arg Phe Glu Asn Glu
            340                 345                 350

Ala Ala Pro Tyr His Glu Phe Val Asp Thr Met Tyr Glu His Gln Lys
        355                 360                 365

Thr Thr Gln Gln Ala Val Pro Ser Trp Ile Val Ile Asp Ala Ser Thr
    370                 375                 380

Lys Ser Arg Tyr Ile Phe Thr Gly Leu Phe Pro Gly Gln Ala Phe Pro
385                 390                 395                 400

Lys Ser Trp Phe Asp His Gly Ile Val Lys Ser Ala Glu Ser Ile Glu
                405                 410                 415

Glu Leu Ala Arg Gln Met Asp Val Leu Leu Glu Ser Leu Ile Glu Thr
            420                 425                 430

Val Asn Arg Phe Asn Asp Phe Ala Arg Asn Gly His Asp Asp Asp Phe
        435                 440                 445

Tyr Arg Gly Asp Ser Val Tyr Asp Asn Tyr Tyr Gly Asp Pro Thr Leu
    450                 455                 460

Pro Asn Pro Asn Leu Ala Glu Ile Lys Lys Ala Pro Phe Tyr Ala Leu
465                 470                 475                 480

Arg Ile Tyr Pro Gly Asp Ile Gly Thr Lys Gly Gly Leu Val Asp Glu
                485                 490                 495

His Ala Arg Val Ile Lys Ala Asp Gly Glu Pro Ile Glu Gly Leu Tyr
            500                 505                 510

Ala Ser Gly Asn Cys Ser Ala Ser Ile Met Gly Glu Thr Tyr Pro Gly
        515                 520                 525

Pro Gly Ala Thr Ile Gly Pro Gly Met Thr Leu Ser Phe Val Ala Ala
    530                 535                 540

Thr Thr His Met Ala Asn Thr Val Lys Lys Glu Glu Val Pro Leu Val
545                 550                 555                 560

Lys Ile
```

<210> SEQ ID NO 12
<211> LENGTH: 1539
<212> TYPE: DNA
<213> ORGANISM: Brevibacterium maris

<400> SEQUENCE: 12
atggtcaact ggaacgaaga atgtgacgtg ttggtggccg ggtcgggcgc cggtggcgtc    60

-continued

```
accggcgcgt acaccgcggc tcgcgagggc tcgacgtga tcctggtcga ggcgacggac    120
aagttcggcg gcaccaccgc gtactccggt ggcggcgggt tctggttccc ggccaacccg    180
gtgctcaagc gcgccggcac cgacgacacg atcgaggacg cgctcgagta ctaccacgcc    240
gtcgtcggcg accggacccc gcgcgagctg caggacacct acgtcaaggg cggcgctccg    300
ctggtcgagt acctcgagca ggacgagaac ctcaagttcg agatgctgcc gtggcccgac    360
tactacggca agatgccgaa ggcccgcaac gacggccagc gccacacgat gccgacgccg    420
ctgccgatct ccgaggtcgg tgacctgcac aagctcgtcc gcggaccgct cgacttcgac    480
cggctcggcc ccgacctgcc cgagatgctg atcggcggcc gcgcgctcgt cggtcgcttc    540
ctcaaggcga tcggcaacta cccgaacgcg aagctgaacc tcaacacccc gctcgtcgag    600
ctggtggtcg aggacggcgc cgtcgtcggc gcgctcgtcg agcgtgacgg cgagcaggtc    660
gcgatccgcg cccgcaaggg cgtcatcctg gcggccggcg gcttcgaggg caacgacgag    720
ctgccgccaga agtacggcgt ccccggtgtc gcgcgcgaca cgatgggtcc gtggggcaac    780
gtcggccagg cgcaccaggc cggcatcgcc gtcggtgccg acaccgacct gatggaccag    840
gcgtggtggt cgccgggcct gacccacccg gacggacgtt ccgcgttcgc gctgtgcttc    900
accggcggca tcttcgtcaa cgacgacggc aagcgcttcg tcaacgagta cgcgccgtac    960
gaccgcctcg gccgcgacat catcgcgggc atggaggacg ctcggtcac gctgccgtac   1020
tggatgatct acgacgacaa gcagggccag cggccgccga tcgcggccac caacgtctcg   1080
atggtcgaga ccgagaagta cgtcgacgcc ggcctgtggc acaccgccga cacgctcgag   1140
gagctggccg aaagatcgg tgtcccggcg agaacctgc tggcaacggt ggagcggttc   1200
aacgcgatgg ccgccaacga cgtcgacgag gacttcggtc gcggcgacga ggcgtacgac   1260
cgggcgttca ccggcggcgg cccggcgctg atcccgatcg agcagggtcc gttccacgct   1320
gccgcgttcg gcatctccga cctcggcacc aagggcggtc tgcgtaccga caccgcggcg   1380
cgggtgctcg acacctcggg caacccgatc cccggtctgt acgcggccgg caacaccatg   1440
gcggccccga gcggcaccac ctaccccggt ggcggtaacc cgatcggcac ctccatgctg   1500
ttcagccaca tcgccgcgat gaacatcgcc ggcaagtag                          1539
```

<210> SEQ ID NO 13
<211> LENGTH: 512
<212> TYPE: PRT
<213> ORGANISM: Brevibacterium maris

<400> SEQUENCE: 13

```
Met Val Asn Trp Asn Glu Glu Cys Asp Val Leu Val Ala Gly Ser Gly
1               5                   10                  15

Ala Gly Gly Val Thr Gly Ala Tyr Thr Ala Ala Arg Glu Gly Leu Asp
                20                  25                  30

Val Ile Leu Val Glu Ala Thr Asp Lys Phe Gly Thr Thr Ala Tyr
            35                  40                  45

Ser Gly Gly Gly Phe Trp Phe Pro Ala Asn Pro Val Leu Lys Arg
        50                  55                  60

Ala Gly Thr Asp Asp Thr Ile Glu Asp Ala Leu Glu Tyr Tyr His Ala
65                  70                  75                  80

Val Val Gly Asp Arg Thr Pro Arg Glu Leu Gln Asp Thr Tyr Val Lys
                85                  90                  95

Gly Gly Ala Pro Leu Val Glu Tyr Leu Glu Gln Asp Glu Asn Leu Lys
            100                 105                 110
```

```
Phe Glu Met Leu Pro Trp Pro Asp Tyr Tyr Gly Lys Met Pro Lys Ala
            115                 120                 125

Arg Asn Asp Gly Gln Arg His Thr Met Pro Thr Pro Leu Pro Ile Ser
    130                 135                 140

Glu Val Gly Asp Leu His Lys Leu Val Arg Gly Pro Leu Asp Phe Asp
145                 150                 155                 160

Arg Leu Gly Ala Asp Leu Pro Glu Met Leu Ile Gly Gly Arg Ala Leu
                165                 170                 175

Val Gly Arg Phe Leu Lys Ala Ile Gly Asn Tyr Pro Asn Ala Lys Leu
            180                 185                 190

Asn Leu Asn Thr Pro Leu Val Glu Leu Val Val Glu Asp Gly Ala Val
    195                 200                 205

Val Gly Ala Leu Val Glu Arg Asp Gly Glu Gln Val Ala Ile Arg Ala
210                 215                 220

Arg Lys Gly Val Ile Leu Ala Ala Gly Gly Phe Glu Gly Asn Asp Glu
225                 230                 235                 240

Leu Arg Gln Lys Tyr Gly Val Pro Gly Val Ala Arg Asp Thr Met Gly
                245                 250                 255

Pro Trp Gly Asn Val Gly Gln Ala His Gln Ala Gly Ile Ala Val Gly
            260                 265                 270

Ala Asp Thr Asp Leu Met Asp Gln Ala Trp Trp Ser Pro Gly Leu Thr
    275                 280                 285

His Pro Asp Gly Arg Ser Ala Phe Ala Leu Cys Phe Thr Gly Gly Ile
    290                 295                 300

Phe Val Asn Asp Asp Gly Lys Arg Phe Val Asn Glu Tyr Ala Pro Tyr
305                 310                 315                 320

Asp Arg Leu Gly Arg Asp Ile Ile Ala Gly Met Glu Asp Gly Ser Val
                325                 330                 335

Thr Leu Pro Tyr Trp Met Ile Tyr Asp Asp Lys Gln Gly Gln Arg Pro
            340                 345                 350

Pro Ile Ala Ala Thr Asn Val Ser Met Val Glu Thr Glu Lys Tyr Val
    355                 360                 365

Asp Ala Gly Leu Trp His Thr Ala Asp Thr Leu Glu Glu Leu Ala Gly
    370                 375                 380

Lys Ile Gly Val Pro Ala Glu Asn Leu Leu Ala Thr Val Glu Arg Phe
385                 390                 395                 400

Asn Ala Met Ala Ala Asn Asp Val Asp Glu Asp Phe Gly Arg Gly Asp
                405                 410                 415

Glu Ala Tyr Asp Arg Ala Phe Thr Gly Gly Pro Ala Leu Ile Pro
            420                 425                 430

Ile Glu Gln Gly Pro Phe His Ala Ala Phe Gly Ile Ser Asp Leu
    435                 440                 445

Gly Thr Lys Gly Gly Leu Arg Thr Asp Thr Ala Ala Arg Val Leu Asp
    450                 455                 460

Thr Ser Gly Asn Pro Ile Pro Gly Leu Tyr Ala Ala Gly Asn Thr Met
465                 470                 475                 480

Ala Ala Pro Ser Gly Thr Thr Tyr Pro Gly Gly Gly Asn Pro Ile Gly
                485                 490                 495

Thr Ser Met Leu Phe Ser His Ile Ala Ala Met Asn Ile Ala Gly Lys
            500                 505                 510

<210> SEQ ID NO 14
<211> LENGTH: 515
<212> TYPE: PRT
```

<213> ORGANISM: Arthrobacter simplex

<400> SEQUENCE: 14

```
Met Asp Trp Ala Glu Glu Tyr Asp Val Leu Val Ala Gly Ser Gly Ala
1               5                   10                  15

Gly Gly Met Ala Gly Thr Tyr Thr Ala Ala Arg Glu Gly Leu Ser Val
                20                  25                  30

Cys Leu Val Glu Ala Gly Asp Lys Phe Gly Thr Thr Ala Tyr Ser
            35                  40                  45

Gly Gly Gly Gly Ala Trp Phe Pro Ala Asn Pro Val Leu Leu Arg Ala
            50                  55                  60

Gly Thr Asp Asp Thr Ile Glu Asp Ala Leu Glu Tyr Arg Ala Val
65                  70                  75                  80

Val Gly Asp Arg Thr Pro Ala Asp Leu Gln Glu Thr Tyr Val Arg Gly
                85                  90                  95

Gly Ala Gly Leu Val Ala Tyr Leu Glu Glu Asp Asp His Phe Ser Phe
                100                 105                 110

Glu Ser Tyr Pro Trp Pro Asp Tyr Phe Gly Asp Ala Pro Lys Ala Arg
                115                 120                 125

Arg Asp Gly Gln Arg His Ile Ile Pro Thr Pro Leu Pro Val Pro Ser
130                 135                 140

Ala Pro Glu Leu Arg Glu Val Val Arg Gly Pro Leu Asp Asn Asp Arg
145                 150                 155                 160

Leu Gly Thr Pro Gln Pro Asp Asp Leu Phe Ile Gly Gly Arg Ala Leu
                165                 170                 175

Val Ala Arg Phe Leu Thr Ala Leu Ala Thr Tyr Pro His Ala Thr Leu
                180                 185                 190

Val Arg Glu Thr Ala Leu Ala Glu Leu Val Glu Asp Gly Val Val
                195                 200                 205

Val Gly Ala Ile Val Glu Thr Asp Gly Val Arg Arg Ala Ile Arg Ala
                210                 215                 220

Arg Arg Gly Val Leu Leu Ala Ala Gly Gly Phe Glu Ala Asn Asp Glu
225                 230                 235                 240

Leu Arg Gln Lys Tyr Gly Val Pro Gly Val Ala Arg Asp Thr Met Gly
                245                 250                 255

Pro Pro Thr Asn Val Gly Ala Ala His Gln Ala Ala Ile Ala Val Gly
                260                 265                 270

Ala Asp Thr Asp Leu Met Gly Glu Ala Trp Trp Ser Pro Gly Leu Thr
                275                 280                 285

His Pro Asp Gly Arg Ser Ala Phe Ala Leu Trp Phe Thr Gly Gly Ile
                290                 295                 300

Phe Val Asp Gly Ala Gly Arg Arg Phe Val Asn Glu Ser Ala Pro Tyr
305                 310                 315                 320

Asp Arg Leu Gly Arg Ala Val Ile Asp His Leu Thr Glu Gly Val
                325                 330                 335

Thr Pro Arg Tyr Trp Met Val Tyr Asp His Lys Glu Gly Ser Ile Pro
                340                 345                 350

Pro Val Arg Ala Thr Asn Val Ser Met Val Asp Glu Glu Gln Tyr Val
                355                 360                 365

Ala Ala Gly Leu Trp His Thr Ala Asp Thr Leu Pro Glu Leu Ala Ala
                370                 375                 380

Leu Ile Gly Val Pro Ala Asp Ala Leu Val Ala Thr Val Ala Arg Phe
385                 390                 395                 400
```

-continued

```
Asn Glu Leu Val Ala Asp Gly Tyr Asp Ala Asp Phe Gly Arg Gly
            405                 410                 415
Glu Ala Tyr Asp Arg Phe Phe Ser Gly Glu Pro Pro Leu Val Ser
        420                 425                 430
Ile Asp Glu Gly Pro Phe His Ala Ala Ala Phe Gly Ile Ser Asp Leu
    435                 440                 445
Gly Thr Lys Gly Gly Leu Arg Thr Asp Thr Ser Ala Arg Val Leu Thr
450                 455                 460
Ala Asp Gly Thr Pro Ile Gly Gly Leu Tyr Ala Ala Gly Asn Thr Met
465                 470                 475                 480
Ala Ala Pro Ser Gly Thr Thr Tyr Pro Gly Gly Asn Pro Ile Gly
            485                 490                 495
Thr Ser Met Leu Phe Ser His Leu Ala Val Arg His Met Gly Thr Glu
            500                 505                 510
Asp Ala Arg
        515

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (10)
<223> OTHER INFORMATION: a, t, c or g
<220> FEATURE:
<221> NAME/KEY: modified_base
<222> LOCATION: (13)
<223> OTHER INFORMATION: a, t, c or g

<400> SEQUENCE: 15
gaatrygatn twntwgtwgy wggwwswgg                                    29

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (4)
<223> OTHER INFORMATION: a, t, c or g
<220> FEATURE:
<221> NAME/KEY: modified_base
<222> LOCATION: (7)
<223> OTHER INFORMATION: a, t, c or g
<220> FEATURE:
<221> NAME/KEY: modified_base
<222> LOCATION: (13)
<223> OTHER INFORMATION: a, t, c or g
<220> FEATURE:
<221> NAME/KEY: modified_base
<222> LOCATION: (16)
<223> OTHER INFORMATION: a, t, c or g

<400> SEQUENCE: 16
narnccnccy ttngtncc                                                18

<210> SEQ ID NO 17
<211> LENGTH: 66
```

<210> SEQ ID NO 17
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 17
ccatcgatga atctggtctt cctattaaaa attatagaat taaactaata ttctgtcaat    60
ttttcc    66

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 18
catgacaaaa ttatttgatt taatcac    27

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatcctgttc cacgtgaaac ag    22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatcctgttt cacgtggaac ag    22

<210> SEQ ID NO 21
<211> LENGTH: 11
<212> TYPE: DNA
<213> ORGANISM: Bacillus sphaericus

<400> SEQUENCE: 21
aagcccttcc t    11

<210> SEQ ID NO 22
<211> LENGTH: 10
<212> TYPE: DNA
<213> ORGANISM: Bacillus sphaericus

<400> SEQUENCE: 22
aggaagggct    10

<210> SEQ ID NO 23
<211> LENGTH: 512
<212> TYPE: PRT
<213> ORGANISM: Brevibacterium maris

<400> SEQUENCE: 23

Met Val Asn Trp Asn Glu Glu Cys Asp Val Leu Val Ala Gly Ser Gly
1               5                   10                  15

```
Ala Gly Gly Val Thr Gly Ala Tyr Thr Ala Ala Arg Glu Gly Leu Asp
             20                  25                  30

Val Ile Leu Val Glu Ala Thr Asp Lys Phe Gly Gly Thr Thr Ala Tyr
             35                  40                  45

Ser Gly Gly Gly Phe Trp Phe Pro Ala Asn Pro Val Leu Lys Arg
     50                  55                  60

Ala Gly Thr Asp Thr Ile Glu Asp Ala Leu Glu Tyr Tyr His Ala
65                  70                  75                  80

Val Val Gly Asp Arg Thr Pro Arg Glu Leu Gln Asp Thr Tyr Val Lys
                85                  90                  95

Gly Gly Ala Pro Leu Val Glu Tyr Leu Glu Gln Asp Glu Asn Leu Lys
             100                 105                 110

Phe Glu Met Leu Pro Trp Pro Asp Tyr Tyr Gly Lys Met Pro Lys Ala
             115                 120                 125

Arg Asn Asp Gly Gln Arg His Thr Met Pro Thr Pro Leu Pro Ile Ser
             130                 135                 140

Glu Val Gly Asp Leu His Lys Leu Val Arg Gly Pro Leu Asp Phe Asp
145                 150                 155                 160

Arg Leu Gly Ala Asp Leu Pro Glu Met Leu Ile Gly Arg Ala Leu
                 165                 170                 175

Val Gly Arg Phe Leu Lys Ala Ile Gly Asn Tyr Pro Asn Ala Lys Leu
             180                 185                 190

Asn Leu Asn Thr Pro Leu Val Glu Leu Val Glu Asp Gly Ala Val
             195                 200                 205

Val Gly Ala Leu Val Glu Arg Asp Gly Glu Gln Val Ala Ile Arg Ala
             210                 215                 220

Arg Lys Gly Val Ile Leu Ala Ala Gly Gly Phe Glu Gly Asn Asp Glu
225                 230                 235                 240

Leu Arg Gln Lys Tyr Gly Val Pro Gly Val Ala Arg Asp Thr Met Gly
                 245                 250                 255

Pro Trp Gly Asn Val Gly Gln Ala His Gln Ala Gly Ile Ala Val Gly
             260                 265                 270

Ala Asp Thr Asp Leu Met Asp Gln Ala Trp Trp Ser Pro Gly Leu Thr
             275                 280                 285

His Pro Asp Gly Arg Ser Ala Phe Ala Leu Cys Phe Thr Gly Gly Ile
             290                 295                 300

Phe Val Asn Asp Asp Gly Lys Arg Phe Val Asn Glu Tyr Ala Pro Tyr
305                 310                 315                 320

Asp Arg Leu Gly Arg Asp Ile Ile Ala Gly Met Glu Asp Gly Ser Val
                 325                 330                 335

Thr Leu Pro Tyr Trp Met Ile Tyr Asp Asp Lys Gln Gly Gln Arg Pro
             340                 345                 350

Pro Ile Ala Ala Thr Asn Val Ser Met Val Glu Thr Glu Lys Tyr Val
             355                 360                 365

Asp Ala Gly Leu Trp His Thr Ala Asp Thr Leu Glu Glu Leu Ala Gly
             370                 375                 380

Lys Ile Gly Val Pro Ala Glu Asn Leu Leu Ala Thr Val Glu Arg Phe
385                 390                 395                 400

Asn Ala Met Ala Ala Asn Asp Val Asp Glu Asp Phe Gly Arg Gly Asp
                 405                 410                 415

Glu Ala Tyr Asp Arg Ala Phe Thr Gly Gly Pro Ala Leu Ile Pro
             420                 425                 430
```

```
Ile Glu Gln Gly Pro Phe His Ala Ala Ala Phe Gly Ile Ser Asp Leu
        435                 440                 445

Gly Thr Lys Gly Gly Leu Arg Thr Asp Thr Ala Ala Arg Val Leu Asp
    450                 455                 460

Thr Ser Gly Asn Pro Ile Pro Gly Leu Tyr Ala Ala Gly Asn Thr Met
465                 470                 475                 480

Ala Ala Pro Ser Gly Thr Thr Tyr Pro Gly Gly Asn Pro Ile Gly
            485                 490                 495

Thr Ser Met Leu Phe Ser His Ile Ala Ala Met Asn Ile Ala Gly Lys
            500                 505                 510
```

<210> SEQ ID NO 24
<211> LENGTH: 510
<212> TYPE: PRT
<213> ORGANISM: Rhodococcus rhodochrous

<400> SEQUENCE: 24

```
Met Ala Glu Trp Ala Glu Cys Asp Val Leu Val Val Gly Ser Gly
1               5                  10                  15

Ala Gly Gly Cys Cys Gly Ala Tyr Thr Pro Ala Arg Glu Gly Leu Ser
            20                  25                  30

Val Ile Leu Val Glu Ala Ser Glu Tyr Phe Gly Gly Thr Thr Ala Tyr
        35                  40                  45

Ser Gly Gly Gly Val Trp Phe Pro Thr Asn Ala Val Leu Gln Arg
    50                  55                  60

Ala Gly Asp Asp Thr Ile Glu Asp Ala Leu Thr Tyr Tyr Pro Arg
65              70                  75                  80

Val Val Gly Asp Arg Thr Pro His Glu Leu Gln Glu Ala Tyr Val Arg
                85                  90                  95

Gly Gly Ala Pro Leu Ile Asp Tyr Leu Glu Ser Asp Asp Leu Glu
            100                 105                 110

Phe Met Val Tyr Pro Trp Pro Asp Tyr Phe Gly Lys Ala Pro Lys Ala
            115                 120                 125

Arg Ala Gln Gly Arg His Ile Val Pro Ser Pro Leu Pro Ile Ala Gly
    130                 135                 140

Asp Pro Glu Leu Asn Glu Ser Ile Arg Gly Pro Leu Gly Arg Glu Arg
145                 150                 155                 160

Ile Gly Glu Pro Leu Pro Asp Met Leu Ile Gly Gly Arg Ala Leu
                165                 170                 175

Val Gly Arg Phe Leu Ile Ala Leu Arg Lys Tyr Pro Asn Val Asp Leu
            180                 185                 190

Tyr Arg Asn Thr Pro Leu Glu Glu Leu Ile Val Glu Asp Gly Val Val
        195                 200                 205

Val Gly Ala Val Val Gly Asn Glu Val Glu Arg Arg Ala Ile Arg Ala
    210                 215                 220

Arg Lys Gly Val Val Leu Ala Ala Gly Gly Phe Asp Gln Asn Asp Glu
225                 230                 235                 240

Met Arg Gly Lys Tyr Gly Val Pro Gly Ala Ala Arg Asp Ser Met Gly
                245                 250                 255

Pro Trp Ser Asn Leu Gly Lys Ala His Glu Ala Gly Ile Ala Val Gly
            260                 265                 270

Ala Asp Val Asp Leu Met Asp Gln Ala Trp Trp Ser Pro Gly Leu Thr
        275                 280                 285

His Pro Asp Gly Arg Ser Ala Phe Ala Leu Cys Phe Thr Gly Gly Ile
    290                 295                 300
```

-continued

```
Phe Val Asp Gln Asp Gly Ala Arg Phe Thr Asn Glu Tyr Ala Pro Tyr
305                 310                 315                 320

Asp Arg Leu Gly Arg Asp Val Ile Ala Arg Met Glu Arg Gly Glu Met
            325                 330                 335

Thr Leu Pro Phe Trp Met Ile Tyr Asp Asp Arg Asn Gly Glu Ala Pro
            340                 345                 350

Pro Val Gly Ala Thr Asn Val Pro Leu Val Glu Thr Glu Lys Tyr Val
            355                 360                 365

Asp Ala Gly Leu Trp Lys Thr Ala Asp Thr Leu Glu Glu Leu Ala Gly
370                 375                 380

Gln Ile Gly Val Pro Ala Glu Ser Leu Lys Ala Thr Val Ala Arg Trp
385                 390                 395                 400

Asn Glu Leu Ala Ala Lys Gly Val Asp Glu Asp Phe Gly Arg Gly Asp
            405                 410                 415

Glu Pro Tyr Asp Arg Phe Phe Ser Gly Gly Glu Pro Pro Leu Val Ser
            420                 425                 430

Ile Asp Glu Gly Pro Phe His Ala Ala Ala Phe Gly Ile Ser Asp Leu
435                 440                 445

Gly Thr Lys Gly Gly Leu Arg Thr Asp Thr Ser Ala Arg Val Leu Thr
            450                 455                 460

Ala Asp Gly Thr Pro Ile Gly Gly Leu Tyr Ala Ala Gly Asn Thr Met
465                 470                 475                 480

Ala Ala Pro Ser Gly Thr Val Tyr Pro Gly Gly Asn Pro Ile Gly
            485                 490                 495

Ala Ser Ala Leu Phe Ala His Leu Ser Val Met Asp Ala Ala
            500                 505                 510

<210> SEQ ID NO 25
<211> LENGTH: 515
<212> TYPE: PRT
<213> ORGANISM: Arthrobacter simplex

<400> SEQUENCE: 25

Met Asp Trp Ala Glu Glu Tyr Asp Val Leu Val Ala Gly Ser Gly Ala
1               5                   10                  15

Gly Gly Met Ala Gly Thr Tyr Thr Ala Ala Arg Glu Gly Leu Ser Val
            20                  25                  30

Cys Leu Val Glu Ala Gly Asp Lys Phe Gly Gly Thr Thr Ala Tyr Ser
            35                  40                  45

Gly Gly Gly Gly Ala Trp Phe Pro Ala Asn Pro Val Leu Leu Arg Ala
        50                  55                  60

Gly Thr Asp Asp Thr Ile Glu Asp Ala Leu Glu Tyr Tyr Arg Ala Val
65                  70                  75                  80

Val Gly Asp Arg Thr Pro Ala Asp Leu Gln Glu Thr Tyr Val Arg Gly
            85                  90                  95

Gly Ala Gly Leu Val Ala Tyr Leu Glu Glu Asp His Phe Ser Phe
            100                 105                 110

Glu Ser Tyr Pro Trp Pro Asp Tyr Phe Gly Asp Ala Pro Lys Ala Arg
            115                 120                 125

Arg Asp Gly Gln Arg His Ile Ile Pro Thr Pro Leu Pro Val Pro Ser
130                 135                 140

Ala Pro Glu Leu Arg Glu Val Val Arg Gly Leu Asp Asn Asp Arg
145                 150                 155                 160

Leu Gly Thr Pro Gln Pro Asp Asp Leu Phe Ile Gly Gly Arg Ala Leu
```

```
                165                 170                 175
Val Ala Arg Phe Leu Thr Ala Leu Ala Thr Tyr Pro His Ala Thr Leu
            180                 185                 190

Val Arg Glu Thr Ala Leu Ala Glu Leu Val Val Glu Asp Gly Val Val
        195                 200                 205

Val Gly Ala Ile Val Glu Thr Asp Gly Val Arg Arg Ala Ile Arg Ala
    210                 215                 220

Arg Arg Gly Val Leu Leu Ala Ala Gly Gly Phe Glu Ala Asn Asp Glu
225                 230                 235                 240

Leu Arg Gln Lys Tyr Gly Val Pro Gly Val Ala Arg Asp Thr Met Gly
                245                 250                 255

Pro Pro Thr Asn Val Gly Ala Ala His Gln Ala Ala Ile Ala Val Gly
            260                 265                 270

Ala Asp Thr Asp Leu Met Gly Glu Ala Trp Trp Ser Pro Gly Leu Thr
        275                 280                 285

His Pro Asp Gly Arg Ser Ala Phe Ala Leu Trp Phe Thr Gly Gly Ile
    290                 295                 300

Phe Val Asp Gly Ala Gly Arg Arg Phe Val Asn Glu Ser Ala Pro Tyr
305                 310                 315                 320

Asp Arg Leu Gly Arg Ala Val Ile Asp His Leu Thr Glu Gly Gly Val
                325                 330                 335

Thr Pro Arg Tyr Trp Met Val Tyr Asp His Lys Glu Gly Ser Ile Pro
            340                 345                 350

Pro Val Arg Ala Thr Asn Val Ser Met Val Asp Glu Glu Gln Tyr Val
        355                 360                 365

Ala Ala Gly Leu Trp His Thr Ala Asp Thr Leu Pro Glu Leu Ala Ala
    370                 375                 380

Leu Ile Gly Val Pro Ala Asp Ala Leu Val Ala Thr Val Ala Arg Phe
385                 390                 395                 400

Asn Glu Leu Val Ala Asp Gly Tyr Asp Ala Asp Phe Gly Arg Gly Gly
                405                 410                 415

Glu Ala Tyr Asp Arg Phe Phe Ser Gly Gly Glu Pro Pro Leu Val Ser
            420                 425                 430

Ile Asp Glu Gly Pro Phe His Ala Ala Phe Gly Ile Ser Asp Leu
        435                 440                 445

Gly Thr Lys Gly Gly Leu Arg Thr Asp Thr Ser Ala Arg Val Leu Thr
    450                 455                 460

Ala Asp Gly Thr Pro Ile Gly Gly Leu Tyr Ala Ala Gly Asn Thr Met
465                 470                 475                 480

Ala Ala Pro Ser Gly Thr Thr Tyr Pro Gly Gly Gly Asn Pro Ile Gly
                485                 490                 495

Thr Ser Met Leu Phe Ser His Leu Ala Val Arg His Met Gly Thr Glu
            500                 505                 510

Asp Ala Arg
        515

<210> SEQ ID NO 26
<211> LENGTH: 562
<212> TYPE: PRT
<213> ORGANISM: Bacillus sphaericus

<400> SEQUENCE: 26

Met Lys Trp Asp Ala Ser Tyr Asp Val Val Val Gly Ser Gly Ala
1               5                   10                  15
```

```
Ala Gly Leu Thr Ala Gly Leu Thr Ala Lys Leu Gln Gly Leu Lys Ser
             20                  25                  30

Leu Val Ile Glu Lys Thr Asp Arg Tyr Gly Gly Ala Ser Ala Ile Ser
         35                  40                  45

Gly Gly Ala Leu Trp Ile Pro Asn Asn His Val Ile Lys Gly Ala Gly
     50                  55                  60

Val Pro Asp Thr His Glu Leu Ala Arg Gln Tyr Leu Asp Ser Thr Val
 65                  70                  75                  80

Gly Asp Arg Val Pro Glu Ala Leu Lys Glu Ala Tyr Ile Thr Arg Gly
                 85                  90                  95

Pro Glu Met Leu Arg Phe Leu Tyr Asn Lys Thr Lys His Met Arg Phe
            100                 105                 110

Gln Tyr Ala Lys Gly Tyr Ser Asp Tyr Tyr Pro Glu Lys Pro Gly Gly
        115                 120                 125

Leu Ser Gln Gly Arg Ser Ile Glu Pro Leu Ile Phe Asp Leu Thr Lys
    130                 135                 140

Met Gly Ser Leu Ala Asn Thr Met Arg Arg Ala Thr Leu Ser Thr Lys
145                 150                 155                 160

Gly Phe Thr Met Asn Ser Tyr Glu Phe His Lys Val Asn Met Ile Thr
                165                 170                 175

Arg Thr Leu Lys Gly Lys Thr Thr Ala Leu Lys Leu Gly Met Arg Leu
            180                 185                 190

Val Lys Ser Lys Val Thr Lys Ser Glu Pro Val Ala Leu Gly Glu Ala
        195                 200                 205

Leu Val Ala Arg Leu Arg Leu Ser Leu Ala Glu Ala Asn Gly Glu Leu
    210                 215                 220

Trp Leu Ser Thr Ala Phe Lys Asp Phe Met Met Asp Lys Gly Arg Val
225                 230                 235                 240

Met Gly Ile Ile Val Glu Arg Asp Gly Gln Glu Leu Arg Ile Glu Ala
                245                 250                 255

Lys Lys Gly Val Val Leu Ser Ser Gly Gly Phe Ser His Asn Gln Ala
            260                 265                 270

Leu Arg Glu Gln Tyr Leu Pro Ser Pro Thr Asn Ala Ala Trp Thr Ser
        275                 280                 285

Ser Pro Glu Gly Gln Thr Gly Asp Val Ile Glu Pro Gly Val Lys Ile
    290                 295                 300

Gly Ala Thr Leu Asp Leu Met Asp Lys Val Trp Gly Ala Pro Ser Val
305                 310                 315                 320

Ile Asp Pro Gln Gly Gln Pro Phe Phe Leu Val Ala Asp Arg Gly Val
                325                 330                 335

Pro Asn Met Ile Val Val Asp Ser Ala Gly Gln Arg Phe Glu Asn Glu
            340                 345                 350

Ala Ala Pro Tyr His Glu Phe Val Asp Thr Met Tyr Glu His Gln Lys
        355                 360                 365

Thr Thr Gln Gln Ala Val Pro Ser Trp Ile Val Ile Asp Ala Ser Thr
    370                 375                 380

Lys Ser Arg Tyr Ile Phe Thr Gly Leu Phe Pro Gly Gln Ala Phe Pro
385                 390                 395                 400

Lys Ser Trp Phe Asp His Gly Ile Val Lys Ser Ala Glu Ser Ile Glu
                405                 410                 415

Glu Leu Ala Arg Gln Met Asp Val Leu Leu Glu Ser Leu Ile Glu Thr
            420                 425                 430

Val Asn Arg Phe Asn Asp Phe Ala Arg Asn Gly His Asp Asp Asp Phe
```

```
              435                 440                 445
Tyr Arg Gly Asp Ser Val Tyr Asp Asn Tyr Tyr Gly Asp Pro Thr Leu
            450                 455                 460
Pro Asn Pro Asn Leu Ala Glu Ile Lys Lys Ala Pro Phe Tyr Ala Leu
465                 470                 475                 480
Arg Ile Tyr Pro Gly Asp Ile Gly Thr Lys Gly Leu Val Asp Glu
            485                 490                 495
His Ala Arg Val Ile Lys Ala Asp Gly Glu Pro Ile Glu Gly Leu Tyr
                500                 505                 510
Ala Ser Gly Asn Cys Ser Ala Ser Ile Met Gly Glu Thr Tyr Pro Gly
            515                 520                 525
Pro Gly Ala Thr Ile Gly Pro Gly Met Thr Leu Ser Phe Val Ala Ala
            530                 535                 540
Thr Thr His Met Ala Asn Thr Val Lys Lys Glu Val Pro Leu Val
545                 550                 555                 560
Lys Ile

<210> SEQ ID NO 27
<211> LENGTH: 563
<212> TYPE: PRT
<213> ORGANISM: Mycobacterium tuberculosis

<400> SEQUENCE: 27

Met Thr Val Gln Glu Phe Asp Val Val Val Gly Ser Gly Ala Ala
1               5                   10                  15
Gly Met Val Ala Ala Leu Val Ala Ala His Arg Gly Leu Ser Thr Val
                20                  25                  30
Val Val Glu Lys Ala Pro His Tyr Gly Gly Ser Thr Ala Arg Ser Gly
            35                  40                  45
Gly Gly Val Trp Ile Pro Asn Asn Glu Val Leu Lys Arg Arg Gly Val
        50                  55                  60
Arg Asp Thr Pro Glu Ala Ala Arg Thr Tyr Leu His Gly Ile Val Gly
65                  70                  75                  80
Glu Ile Val Glu Pro Glu Arg Ile Asp Ala Tyr Leu Asp Arg Gly Pro
                85                  90                  95
Glu Met Leu Ser Phe Val Leu Lys His Thr Pro Leu Lys Met Cys Trp
            100                 105                 110
Val Pro Gly Tyr Ser Asp Tyr Tyr Pro Glu Ala Pro Gly Gly Arg Pro
        115                 120                 125
Gly Gly Arg Ser Ile Glu Pro Lys Pro Phe Asn Ala Arg Lys Leu Gly
    130                 135                 140
Ala Asp Met Ala Gly Leu Glu Pro Ala Tyr Gly Lys Val Pro Leu Asn
145                 150                 155                 160
Val Val Met Gln Gln Asp Tyr Val Arg Leu Asn Gln Leu Lys Arg
                165                 170                 175
His Pro Arg Gly Val Leu Arg Ser Met Lys Val Gly Ala Arg Thr Met
            180                 185                 190
Trp Ala Lys Ala Thr Gly Lys Asn Leu Val Gly Met Gly Arg Ala Leu
        195                 200                 205
Ile Gly Pro Leu Arg Ile Gly Leu Gln Arg Ala Gly Val Pro Val Glu
    210                 215                 220
Leu Asn Thr Ala Phe Thr Asp Leu Phe Val Glu Asn Gly Val Val Ser
225                 230                 235                 240
Gly Val Tyr Val Arg Asp Ser His Glu Ala Glu Ser Ala Glu Pro Gln
```

```
                    245                 250                 255
Leu Ile Arg Ala Arg Gly Val Ile Leu Ala Cys Gly Gly Phe Glu
            260                 265                 270

His Asn Glu Gln Met Arg Ile Lys Tyr Gln Arg Ala Pro Ile Thr Thr
            275                 280                 285

Glu Trp Thr Val Gly Ala Ser Ala Asn Thr Gly Asp Gly Ile Leu Ala
            290                 295                 300

Ala Glu Lys Leu Gly Ala Ala Leu Asp Leu Met Asp Asp Ala Trp Trp
305                 310                 315                 320

Gly Pro Thr Val Pro Leu Val Gly Lys Pro Trp Phe Ala Leu Ser Glu
                325                 330                 335

Arg Asn Ser Pro Gly Ser Ile Ile Val Asn Met Ser Gly Lys Arg Phe
                340                 345                 350

Met Asn Glu Ser Met Pro Tyr Val Glu Ala Cys His His Met Tyr Gly
                355                 360                 365

Gly Glu His Gly Gln Gly Pro Gly Pro Gly Glu Asn Ile Pro Ala Trp
            370                 375                 380

Leu Val Phe Asp Gln Arg Tyr Arg Asp Arg Tyr Ile Phe Ala Gly Leu
385                 390                 395                 400

Gln Pro Gly Gln Arg Ile Pro Ser Arg Trp Leu Asp Ser Gly Val Ile
                405                 410                 415

Val Gln Ala Asp Thr Leu Ala Glu Leu Ala Gly Lys Ala Gly Leu Pro
                420                 425                 430

Ala Asp Glu Leu Thr Ala Thr Val Gln Arg Phe Asn Ala Phe Ala Arg
            435                 440                 445

Ser Gly Val Asp Glu Asp Tyr His Arg Gly Glu Ser Ala Tyr Asp Arg
            450                 455                 460

Tyr Tyr Gly Asp Pro Ser Asn Lys Pro Asn Pro Asn Leu Gly Glu Val
465                 470                 475                 480

Gly His Pro Pro Tyr Tyr Gly Ala Lys Met Val Pro Gly Asp Leu Gly
                485                 490                 495

Thr Lys Gly Gly Ile Arg Thr Asp Val Asn Gly Arg Ala Leu Arg Asp
            500                 505                 510

Asp Gly Ser Ile Ile Asp Gly Leu Tyr Ala Ala Gly Asn Val Ser Ala
            515                 520                 525

Pro Val Met Gly His Thr Tyr Pro Gly Pro Gly Thr Ile Gly Pro
            530                 535                 540

Ala Met Thr Phe Gly Tyr Leu Ala Ala Leu His Ile Ala Asp Gln Ala
545                 550                 555                 560

Gly Lys Arg

<210> SEQ ID NO 28
<211> LENGTH: 507
<212> TYPE: PRT
<213> ORGANISM: Nocardia opaca

<400> SEQUENCE: 28

Met Gln Asp Trp Thr Ser Glu Cys Asp Leu Leu Val Val Gly Ser Gly
1               5                   10                  15

Gly Gly Ala Leu Thr Gly Ala Tyr Thr Ala Ala Ala Gln Gly Leu Thr
            20                  25                  30

Thr Ile Val Leu Glu Lys Thr Asp Arg Phe Gly Gly Thr Ser Ala Tyr
            35                  40                  45

Ser Gly Ala Ser Ile Trp Leu Pro Gly Thr Gln Val Gln Glu Arg Ala
```

-continued

```
              50                  55                  60
Gly Leu Pro Asp Ser Thr Glu Asn Ala Arg Ser Tyr Leu Arg Ala Leu
 65                  70                  75                  80

Leu Gly Asp Ala Glu Ser Glu Arg Gln Asp Ala Tyr Val Glu Thr Ala
                     85                  90                  95

Pro Ala Val Val Ala Leu Leu Glu Gln Asn Pro Asn Ile Glu Phe Glu
                100                 105                 110

Phe Arg Ala Phe Pro Asp Tyr Tyr Lys Ala Glu Gly Arg Met Asp Thr
                115                 120                 125

Gly Arg Ser Ile Asn Pro Leu Asp Leu Asp Pro Ala Asp Ile Gly Asp
                130                 135                 140

Leu Ala Gly Arg Cys Val Arg Asn Cys Thr Lys Thr Asp Arg Met Asp
145                 150                 155                 160

His Ala Pro Gly Arg Met Ile Gly Gly Arg Ala Leu Ile Ala Val Ser
                165                 170                 175

Ala Ala Val Gln Ser Thr Ala Arg Gln Asn Phe Ala Pro Glu Ser Val
                180                 185                 190

Leu Thr Ser Leu Ile Val Glu Asp Gly Arg Val Val Gly Gly Leu Arg
                195                 200                 205

Ser Asn Pro Arg Tyr Arg Gln Arg Ile Lys Ala Asn Arg Gly Val Leu
                210                 215                 220

Met His Ala Gly Gly Gly Phe Glu Gly Asn Ala Glu Met Arg Glu Gln
225                 230                 235                 240

Ala Gly Thr Pro Gly Lys Ala Ile Trp Ser Met Gly Pro Ser Gly Pro
                245                 250                 255

Thr Pro Ala Thr Arg Ser Pro Pro Glu Leu Ala Gly Arg Arg Asn
                260                 265                 270

Ser Leu Ala Arg Ser Gly Val Val Leu Pro Arg Gly Arg Ala Ala Arg
                275                 280                 285

Arg Arg Arg Leu His Gly Arg Val Arg Gly Gly Leu Val Val Asp Ser
                290                 295                 300

Pro Gly Ser Val Pro Gln Arg Val Ala Ser Val Arg Pro Val Arg Thr
305                 310                 315                 320

Ser His Gly Cys Ser Pro Asp Asp Asn Gly Ser Ala Val Pro Ser Phe
                325                 330                 335

Met Ile Phe Asp Ser Arg Glu Val Thr Asp Cys Pro Pro Ser Ala Ser
                340                 345                 350

Arg Thr Arg Pro Pro Pro Ser Thr Ser Lys Pro Glu Pro Gly Ser Val
                355                 360                 365

Pro Thr Leu Ser Lys Asn Ser Leu Pro Arg Pro Asp Tyr Arg Pro Glu
                370                 375                 380

Arg Ile Ala Gln His Cys Arg Lys Val Gln Arg Cys Arg Lys Leu Gly
385                 390                 395                 400

Val Asp Glu Glu Phe His Arg Gly Asp Pro Tyr Asp Ala Phe Phe
                405                 410                 415

Cys Pro Pro Asn Gly Gly Ala Asn Ala Ala Leu Thr Ala Ile Glu Asn
                420                 425                 430

Gly Pro Phe Tyr Ala Ala Arg Asp Arg Leu Ser Asp Leu Gly Thr Lys
                435                 440                 445

Gly Gly Leu Val Thr Asp Val Asn Gly Arg Val Leu Arg Ala Asp Gly
                450                 455                 460

Ser Ala Ile Asp Gly Leu Tyr Ala Ala Gly Asn Thr Ser Ala Ser Val
465                 470                 475                 480
```

Ala Pro Phe Tyr Pro Gly Pro Gly Val Pro Leu Gly Thr Ala Met Val
            485                 490                 495

Phe Ser Tyr Arg Ala Ala Gln Asp Met Ala Lys
            500                 505

<210> SEQ ID NO 29
<211> LENGTH: 573
<212> TYPE: PRT
<213> ORGANISM: Comamonas testosteroni

<400> SEQUENCE: 29

Met Ala Glu Gln Glu Tyr Asp Leu Ile Val Val Gly Ser Gly Ala Gly
1               5                   10                  15

Ala Cys Trp Ala Pro Ile Arg Ala Gln Glu Gln Gly Leu Lys Thr Leu
            20                  25                  30

Val Val Glu Lys Thr Glu Leu Phe Gly Gly Thr Ser Ala Leu Ser Gly
        35                  40                  45

Gly Gly Ile Trp Ile Pro Leu Asn Tyr Asp Gln Lys Thr Ala Gly Ile
    50                  55                  60

Lys Asp Asp Leu Glu Thr Ala Phe Gly Tyr Met Lys Arg Cys Val Arg
65                  70                  75                  80

Gly Met Ala Thr Asp Asp Arg Val Leu Ala Tyr Val Glu Thr Ala Ser
            85                  90                  95

Lys Met Ala Glu Tyr Leu Arg Gln Ile Gly Ile Pro Tyr Arg Ala Met
            100                 105                 110

Ala Lys Tyr Ala Asp Tyr Tyr Pro His Ile Glu Gly Ser Arg Pro Gly
        115                 120                 125

Gly Arg Thr Met Asp Pro Val Asp Phe Asn Ala Ala Arg Leu Arg Val
    130                 135                 140

Thr Ala Leu Glu Thr Met Arg Pro Gly Pro Gly Asn Gln Leu Phe
145                 150                 155                 160

Gly Arg Met Ser Ile Ser Ala Phe Glu Ala His Ser Met Leu Ser Arg
            165                 170                 175

Glu Leu Lys Ser Arg Phe Thr Ile Leu Gly Ile Met Leu Lys Tyr Phe
            180                 185                 190

Leu Asp Tyr Pro Trp Arg Asn Lys Thr Arg Arg Asp Arg Arg Met Thr
        195                 200                 205

Gly Gly Gln Ala Leu Val Ala Gly Leu Leu Thr Ala Ala Asn Lys Ala
    210                 215                 220

Arg Val Glu Met Trp Cys Asn Ser Pro Leu Lys Glu Leu Val Gln Asp
225                 230                 235                 240

Ala Ser Gly Arg Val Thr Gly Val Ile Val Glu Arg Asn Gly Gln Arg
            245                 250                 255

Gln Gln Ile Asn Ala Arg Arg Gly Val Leu Leu Gly Ala Gly Gly Phe
            260                 265                 270

Glu Arg Asn Gln Glu Met Arg Asp Gln Tyr Leu Asn Lys Pro Thr Arg
        275                 280                 285

Leu Val Asp Gly Asn Pro Cys Gly Arg Gln Tyr Gly Asp Ala His Arg
    290                 295                 300

Ala Gly Gln Ala Trp Ala His Thr Gly Ala Asp Gly Leu Val Leu Gly
305                 310                 315                 320

Arg Ala His His Gly Cys Ser Gln Gly Ala Gly Leu Ser Arg His Phe
            325                 330                 335

Arg Gly Thr Leu Ala Ala Gly Val His Gly Gly Gln Arg Gln Gly Ala

-continued

```
                    340             345             350
Ala Leu Pro Gln Arg Val Arg Pro Val Ser Gly Ile Pro Ala Ala Met
            355             360             365

Leu Ala Glu Asn Ala Lys Gly Asn Gly Gly Val Pro Ala Trp Ile Val
    370             375             380

Phe Asp Ala Ser Phe Arg Ala Gln Asn Pro Met Gly Pro Leu Met Pro
385             390             395             400

Gly Ser Ala Val Pro Asp Ser Lys Val Arg Lys Ser Trp Leu Asn Asn
                405             410             415

Val Tyr Trp Lys Gly Arg Arg Trp Lys Ile Trp Arg Ala Asp Arg Arg
            420             425             430

Gly Arg Ala Gly Leu Gln Val Ser Ala Arg Arg Met Thr Glu Tyr Ala
        435             440             445

Arg Ala Gly Lys Asp Leu Asp Phe Asp Arg Gly Gly Asn Val Phe Asp
    450             455             460

Arg Tyr Tyr Gly Asp Pro Arg Leu Lys Asn Pro Asn Leu Gly Pro Ile
465             470             475             480

Glu Lys Gly Pro Phe Tyr Ala Met Arg Leu Trp Pro Gly Glu Ile Gly
                485             490             495

Thr Lys Gly Gly Leu Leu Thr Asp Arg Glu Gly Arg Val Leu Asp Thr
            500             505             510

Gln Gly Arg Ile Ile Glu Gly Leu Tyr Cys Val Gly Asn Asn Ser Ala
        515             520             525

Ser Val Met Ala Pro Ala Tyr Ala Gly Ala Gly Ser Thr Leu Gly Pro
    530             535             540

Ala Met Thr Phe Ala Phe Arg Ala Val Ala Asp Met Val Gly Lys Pro
545             550             555             560

Leu Pro Leu Glu Asn Pro His Leu Leu Gly Lys Thr Val
                565             570
```

The invention claimed is:

1. A process for selective introduction of a double bond into ring A of a steroid skeleton by overexpression of 3-keto steroid-$\Delta^1$-dehydrogenases, wherein a) a $\Delta^1$-dehydrogenase gene encoding a polypeptide comprising Seq. ID No. 11 is isolated from *Bacillus sphaericus*, cloned and amplified, b) promoter and terminator elements of the 3-keto steroid-$\Delta^1$-dehydrogenase gene or other promoter and terminator elements are isolated from the same or another bacterium, cloned and amplified, c) expression plasmids are constructed in which the 3-keto steroid-$\Delta^1$-dehydrogenase gene from a), is flanked by promoter and terminator sequences of the 3-keto steroid-$\Delta^1$-dehydrogenase gene or by other promoter and terminator elements from b), is contained, d) *B. sphaericus*, *B. subtilis*, or *E. coli* host bacteria are transformed with the expression plasmid that is produced under c), and e) the thus produced bacteria are cultivated, and the selective dehydrogenation at 1-position in the steroid skeleton of hydrocortisone (F), hydrocortisone-17-acetate (MAF), hydrocortisone-21-acetate (EAF), 4-androstene-3-17-dione(AD), fluocortolone A acetate (FCAA) or 11β,17α-Dihydroxy-6α,9α-difluoro-16α-methylprogesterone (DDFMP) is performed with these cultures, whereby i) a high substrate concentration at unaltered operating times is used, and ii) no disruptive secondary zones are produced.

2. The process according to claim 1, wherein said promoter comprises Seq. ID No. 9 or a sequence having at least 90% homology to Seq. ID No.9.

3. The process according to claim 1, wherein said selective dehydrogenation at the 1-position in the steroid skeleton forms betamethasone, clobetasone, clocortolone, $\Delta^1$-11β, 17α-dihydroxy-6α,9α-difluoro-16α-methylprogesterone, deflazacort, dexamethasone, diflocortolone, fluocinolone acetonide, fluocortolone, hydroxy acid or prednisolone and derivatives thereof.

4. The process according to claim 1, wherein said promoter or terminator is a constitutive promoters that is p(veg), a promoter of bacteriophages Φ29 or SPO1, an inducible promoters that is p(aprE) or p(sacB) from *Bacillus subtilis*, a hybrid promoter that is a ladI-controlled SPO1-promoter, a terminator of *Eseherichia coli* that is t(rrnB) or of *Bacillus subtilis* that is t(senS) or t(senN).

5. The process of claim 1, wherein said terminator is the terminator of the 3-Keto steroid-$\Delta^1$-dehydrogenase gene from *Bacillus sphaericus* comprising SEQ ID NO: 10.

6. The process of claim 1, wherein said host cell is *B. sphaericus.*

* * * * *

UNITED STATES PATENT AND TRADEMARK OFFICE
CERTIFICATE OF CORRECTION

PATENT NO. : 7,416,866 B2
APPLICATION NO. : 10/355238
DATED : August 26, 2008
INVENTOR(S) : Tilman Spellig It is certified that error appears in the above-identified patent and that said Letters Patent is hereby corrected as shown below:

Title page, Item (75), Inventor, reads "Tillman Spelling" should read -- Tilman Spellig --

Title Page, Item (12), reads "Spelling" should read -- Spellig --

Column 76, line 54, reads "a constitutive promoters" should read -- a constitutive promoter --

Column 76, line 57, reads "ladI-controlled" should read -- lacI-controlled --

Column 76, line 58, reads "Eseherichia coli" should read -- Escherichia coli --

Signed and Sealed this

Third Day of March, 2009

JOHN DOLL
*Acting Director of the United States Patent and Trademark Office*